(12) United States Patent
Frederick et al.

(10) Patent No.: US 12,163,139 B2
(45) Date of Patent: *Dec. 10, 2024

(54) TOBACCO PLANTS HAVING INCREASED NITROGEN EFFICIENCY AND METHODS OF USING SUCH PLANTS

(71) Applicant: ALTRIA CLIENT SERVICES LLC, Richmond, VA (US)

(72) Inventors: Jesse Frederick, Richmond, VA (US); Chengalrayan Kudithipudi, Midlothian, VA (US); Dongmei Xu, Glen Allen, VA (US)

(73) Assignee: Altria Client Services LLC, Richmond, VA (US)

(*) Notice: Subject to any disclaimer, the term of this patent is extended or adjusted under 35 U.S.C. 154(b) by 178 days.

This patent is subject to a terminal disclaimer.

(21) Appl. No.: 17/587,441

(22) Filed: Jan. 28, 2022

(65) Prior Publication Data

US 2022/0142228 A1    May 12, 2022

Related U.S. Application Data

(63) Continuation of application No. 15/727,418, filed on Oct. 6, 2017, now Pat. No. 11,266,174.

(60) Provisional application No. 62/405,747, filed on Oct. 7, 2016.

(51) Int. Cl.
*C12N 15/82* (2006.01)
*A24B 3/12* (2006.01)
*A24B 15/20* (2006.01)
*C12N 9/88* (2006.01)
*C12N 15/10* (2006.01)
*C12N 15/66* (2006.01)
*A61K 38/00* (2006.01)

(52) U.S. Cl.
CPC ............ *C12N 15/8261* (2013.01); *A24B 3/12* (2013.01); *A24B 15/20* (2013.01); *C12N 9/88* (2013.01); *C12N 15/102* (2013.01); *C12N 15/66* (2013.01); *C12N 15/8243* (2013.01); *C12N 15/825* (2013.01); *C12N 15/8269* (2013.01); *C12Y 401/01015* (2013.01); *A61K 38/00* (2013.01); *Y02A 40/146* (2018.01)

(58) Field of Classification Search
None
See application file for complete search history.

(56) References Cited

U.S. PATENT DOCUMENTS

| | | |
|---|---|---|
| 4,516,590 A | 5/1985 | Teng |
| 4,528,993 A | 7/1985 | Sensabaugh et al. |
| 4,660,577 A | 4/1987 | Sensabaugh et al. |
| 4,683,195 A | 7/1987 | Mullis et al. |
| 4,683,202 A | 7/1987 | Mullis |
| 4,732,856 A | 3/1988 | Federoff |
| 4,761,373 A | 8/1988 | Anderson et al. |
| 4,769,061 A | 9/1988 | Comai |
| 4,800,159 A | 1/1989 | Mullis et al. |
| 4,810,648 A | 3/1989 | Stalker |
| 4,848,373 A | 7/1989 | Lenkey |
| 4,940,835 A | 7/1990 | Shah et al. |
| 4,945,050 A | 7/1990 | Sanford et al. |
| 4,965,188 A | 10/1990 | Mullis et al. |
| 4,975,374 A | 12/1990 | Goodman et al. |
| 4,987,907 A | 1/1991 | Townend |
| 5,004,863 A | 4/1991 | Umbeck |
| 5,013,658 A | 5/1991 | Dooner et al. |
| 5,013,659 A | 5/1991 | Bedbrook et al. |
| 5,104,310 A | 4/1992 | Saltin |
| 5,141,131 A | 8/1992 | Miller, Jr. et al. |
| 5,149,645 A | 8/1992 | Hoekema et al. |
| 5,159,135 A | 10/1992 | Umbeck |
| 5,162,602 A | 11/1992 | Somers et al. |
| 5,164,180 A | 11/1992 | Payne et al. |
| 5,177,010 A | 1/1993 | Goldman et al. |
| 5,231,019 A | 7/1993 | Paszkowski et al. |
| 5,276,268 A | 1/1994 | Strauch et al. |
| 5,316,931 A | 5/1994 | Donson et al. |
| 5,372,149 A | 12/1994 | Roth et al. |
| 5,463,174 A | 10/1995 | Moloney et al. |
| 5,464,763 A | 11/1995 | Schilperoort et al. |
| 5,469,976 A | 11/1995 | Burchell |
| 5,545,565 A | 8/1996 | Greeve et al. |
| 5,561,236 A | 10/1996 | Leemans et al. |
| 5,563,055 A | 10/1996 | Townsend et al. |
| 5,589,367 A | 12/1996 | Donson et al. |
| 5,659,026 A | 8/1997 | Baszczynski et al. |

(Continued)

FOREIGN PATENT DOCUMENTS

| | | |
|---|---|---|
| EP | 024 2 246 | 10/1987 |
| WO | WO 02/38736 | 5/2002 |

(Continued)

OTHER PUBLICATIONS

Allen et al., "microRNA-Directed Phasing During Trans-Acting siRNA Biogenesis in Plants," *Cell*, 121:207-221 (2005).

Altschul et al., "Basic Local Alignment Search Tool," *J. Mol. Biol.*, 215:403-410 (1990).

Altschul et al., "Gapped BLAST and PSI-BLAST: a New Generation of Protein Database Search Programs," *Nucleic Acids Res.*, 25:3389-3402 (1997).

(Continued)

*Primary Examiner* — Cynthia E Collins
(74) *Attorney, Agent, or Firm* — Arnold & Porter Kaye Scholer LLP

(57) ABSTRACT

This disclosure provides a number of sequences involved in nitrogen utilization, methods of using such sequences, tobacco plants carrying modifications to such sequences, tobacco plants transgenic for such sequences, and tobacco products made from such plants.

16 Claims, 8 Drawing Sheets

Specification includes a Sequence Listing.

(56) References Cited

U.S. PATENT DOCUMENTS

| | | | |
|---|---|---|---|
| 5,767,366 | A | 6/1998 | Sathasivan et al. |
| 5,789,156 | A | 8/1998 | Bujard et al. |
| 5,814,618 | A | 9/1998 | Bujard et al. |
| 5,866,785 | A | 2/1999 | Donson et al. |
| 5,879,903 | A | 3/1999 | Strauch et al. |
| 5,879,918 | A | 3/1999 | Tomes et al. |
| 5,886,244 | A | 3/1999 | Tomes et al. |
| 5,889,190 | A | 3/1999 | Donson et al. |
| 5,889,191 | A | 3/1999 | Turpen |
| 5,928,937 | A | 7/1999 | Kakefuda et al. |
| 5,932,782 | A | 8/1999 | Bidney |
| 5,981,840 | A | 11/1999 | Zhao et al. |
| 6,072,050 | A | 6/2000 | Bowen et al. |
| 6,084,155 | A | 7/2000 | Volrath et al. |
| 6,166,302 | A | 12/2000 | Merlo et al. |
| 6,451,732 | B1 | 9/2002 | Beckett et al. |
| 6,451,735 | B1 | 9/2002 | Ottaway et al. |
| 6,727,411 | B2 * | 4/2004 | Kisaka ............... C12N 15/8251 800/300 |
| 11,266,174 | B2 * | 3/2022 | Frederick ............... C12N 15/66 |
| 2001/0016956 | A1 | 8/2001 | Ward et al. |
| 2003/0101487 | A1 | 5/2003 | Kisaka et al. |
| 2003/0110530 | A1 | 6/2003 | Shelp et al. |
| 2004/0118422 | A1 | 6/2004 | Lundin et al. |
| 2005/0178398 | A1 | 8/2005 | Breslin et al. |
| 2005/0244521 | A1 | 11/2005 | Strickland et al. |
| 2006/0191548 | A1 | 8/2006 | Strickland et al. |
| 2012/0024301 | A1 | 2/2012 | Carroll et al. |
| 2012/0031414 | A1 | 2/2012 | Atchley et al. |
| 2012/0031416 | A1 | 2/2012 | Atchley et al. |
| 2012/0199148 | A1 | 8/2012 | Xu et al. |
| 2015/0173319 | A1 | 6/2015 | Frederick et al. |

FOREIGN PATENT DOCUMENTS

| | | |
|---|---|---|
| WO | WO 2004/041006 A1 | 5/2004 |
| WO | WO 2007/092704 A2 | 8/2007 |
| WO | WO 2009/054735 | 4/2009 |
| WO | WO 2009/105612 | 8/2009 |
| WO | WO 2011/025514 A1 | 3/2011 |

OTHER PUBLICATIONS

Anderson et al., "Cell-specific expression of the promoters of two nonlegume hemoglobin genes in a transgenic legume, Lotus corniculatus," Plant Physiol. 113(1):45-57 (1997).

Bartel, "MicroRNAs: Genomics, Biogenesis, Mechanism, and Function," *Cell*, 116:281-297 (2004).

Bindler et al., "A High Density Genetic Map of Tobacco (*Nicotiana tabacum* L.) Obtained from Large Scale Microsatellite Marker Development," *Theor. Appl. Genet*, 123:219-230 (2011).

Bingguang et al., "SNP-based Genetic Linkage Map of Tobacco (*Nicotiana tabacum* L.) Using Next-Generation RAD Sequencing," *J. of Biol. Res-Thessaloniki*, 22:11 (2015).

Biswas et al., "The Development of DNA Based Methods for the Reliable and Efficient Identification of *Nicotiana tabacum* in Tobacco and Its Derived Products," *International Journal of Analytical Chemistry*, pp. 1-6 (Aug. 2016).

Brauer and Shelp, "Nitrogen use efficiency: re-consideration of the bioengineering approuach," 88(2):103-110 (2010).

Brown et al., "Using RNAi to investigate orthologous homeotic gene function during development of distantly related insects," *Evolution & Development*, 1(1):11-15 (1999).

Canevascini et al., "Tissue-Specific Expression and Promoter Analysis of the Tobacco Itp1 Gene," *Plant Physiol.*, 112(2):513-524 (1996).

Chenna et al., "Multiple sequence alignment with the clustal series of programs," Nucleic Acids Research, 31(13):3497-3500 (2003).

Christensen et al., "Maize Polyubiquitin Genes: Structure, Thermal of Expression and Transcript Splicing, and Promoter Activity Following Transfer to Protoplasts by Electroporation," *Plant Mol. Biol.*, 18:675-689 (1992).

Christensen et al., "Sequence Analysis and Transcriptional Regulation by Heat Shock of Polyubiquitin Transcripts from Maize," *Plant Mol. Biol.*, 12:619-632 (1989).

Christou et al., "Stable Transformation of Soybean Callus by DNA-Coated Gold Particles," *Plant Physiol.*, 87:671-674 (1988).

Crossway et al., "Micromanipulation Techniques in Plant Biotechnology," *Biotechniques*, 4:320-334 (1986).

Davis et al., "Tobacco, Production, Chemistry and Technology," eds., Blackwell Publishing, Oxford, Chapters 4B and 4C, pp. 70-103 (1999).

Dayhoff et al., "22 A model of evolutionary change in proteins," Atlas of protein sequence and structure, 5(3):345-352 (1978).

De Pater et al., "A 22-bp fragment of the pea lectin promoter containing essential TGAC-like motifs confers seed-specific gene expression," Plant Cell 5(8):877-886 (1993).

De Wet et al., "Exogenous Gene Transfer in Maize (*Zea mays*) Using DNA-treated Pollen," The Experimental Manipulation of Ovule Tissues, pp. 197-209 (1985).

D'Halluin et al., "Transgenic Maize Plants by Tissue Electroporation," *Plant Cell*, 4:1495-1505 (1992).

Doferus et al., "Differential interactions of promoter elements in stress responses of the *Arabidopsis* ADH gene," Plant Physiol, 105(41):1075-1087 (1994).

Edwards et al., "A Reference Genome for *Nicotiana tabacum* Enables Map-based Cloning of Homeologous Loci Implicated in Nitrogen Utilization Efficiency," BMC Genomics, 18:448 (2017).

Eyal et al., "Pollen specificity elements reside in 30 bp of the proximal promoters of two pollen-expressed genes," Plant Cell, 7(3):373-384 (1995).

Fedoroff et al., "Cloning of the bronze Locus in Maize by a Simple and Generalizable Procedure Using the Transposable Controlling Element *Activator (Ac)*," *Proc. Natl. Acad. Sci.*, 81:3825-3829 (1984).

Finer et al., "Transformation of Soybean Via Particle Bombardment of Embryogenic Suspension Culture Tissue," *In Vitro Cell Dev. Biol.*, 27P:175-182 (1991).

Fischhoff et al., "Insect tolerant transgenic tomato plants," Nature Biotechnology, 5:807-813 (1987).

Gao et al., "CRISPI\VCas9-mediated targeted mutagenesis in *Nicotiana tabacum*," Plant Mol Biol, 87199-110 (2014).

Gatz et al., "Regulation of a Modified CaMV 35S Promoter by the Tn 10-encoded Tet repressor in Transgenic Tobacco," *Mol. Gen. Genet.*, 227:229-237 (1991).

GenBank Accession No. XM_009613937, Nicotiana tomentosiformis kirola-like (LOC104105589), pp. 2 (2016).

Goldman et al., "Female Sterile Tobacco Plants are Produced by Stigma-Specific Cell Ablation," *EMBO Journal*, 13:2976-2984 (1994).

Griffiths-Jones et al., "Rfam: an RNA Family Database," *Nucleic Acids Res.*, 31:439-441 (2003).

Guevara-Garcia et al., "Tissue-Specific and Wound-Inducible Pattern of Expression of the Mannopine Synthase Promoter is Determined by the Interaction Between Positive and Negative cis-regulatory Elements," *Plant J.*, 4(3):495-505 (1993).

Guo et al., "Protein tolerance to random amino acid change," Proc. Natl. Acad. Sci. USA, 101:9205-9210 (2004).

Gut et al., "A common structural basis for PH and calmodulin-mediated regulation in plant glutamate decarboxylase," Journal of Molecular Biology, 392(2):334-351 (2009).

Ha et al., "Cis-acting regulatory elements controlling temporal and organ-specific activity of nopaline synthase promoter," Nucleic Acids Research, 17(1):215-223 (1989).

Hansen et al., "Wound-inducible and Organ-Specific Expression of ORF13 from *Agrobacterium rhizogenes* 8196 T-DNA in Transgenic Tobacco Plants," *Molecular General Genetics*, 254(3):337-343 (1997).

Hildering et al, "The Use of Induced Mutations in Plant Breeding," Pergamon Press, pp. 317-320 (1965).

Hill et al, "Functional analysis of conserved histidines in ADP-glucose pyrophosphorlyase from *Escherichia coli*," Biochem Biophys Res Commun, 244(2): 573-577 (1998).

Hoekema et al, "A Binary Plant Vector Strategy Based on Separation of vir- and T-region of the *Agrobacterium tumefaciens* Ti-plasmid," Nature, 303: 179-180 (1983).

(56) References Cited

OTHER PUBLICATIONS

Hormoz, "Amino acid composition of proteins reduces deleterious impact of mutations," *Scientific Reports*, 3:2919 (2013).
Horsch et al, "A simple and general method for transferring genes into plants," Science, 227:1229-1231 (1985).
Hortensteiner and Krautler, "Chlorophyll breakdown in higher plants," Biochimica et Biophysica Acta, 1807:977-988 (2011).
International Search Report and Written Opinion in International Application PCT/US2018/049156 dated Jan. 28, 2019.
International Search Report and Written Opinion in International Application No. PCT/US2017/055635, dated Jan. 26, 2018, 16 pages.
Kaeppler et al., "Silicon Carbide Fiber-mediated DNA Delivery into Plant Cells," *Plant Cell Reports*, 9:415-418 (1990).
Kaeppler et al, "Silicon Carbide Fiber-mediated Stable Transformation of Plant Cells," *Theor. Appl. Genet.*, 84:560-566 (1992).
Kim et al, "A 20 nucleotide upstream element is essential for the nopaline sythenase (nos) promoter activity," Plant Mol Biol, 24(1):105-117 (1994).
Kouranov et al., "Analysis of the Interactions of Preproteins with the Import Machinery over the Course of Protein Import into Chloroplasts," *Journal of Cell Biology*, 139(7):1677-1685 (1997).
Kouranov et al., "Tic20 and Tic22 Are New Components of the Protein Import Apparatus at the Chloroplast Inner Envelope Membrane," *Journal of Cell Biology*, 143(4):991-1002 (1998).
Kumar et al., "Comparative phylogenetic analysis and transcriptional profiling of MADS-box gene family identified DAM and FLC-like genes in apple (Malus X domestica)," Scientific Reports, 6:20695 (2016).
Ladha et al. "Efficiency of Fertilizer Nitrogen in Cereal Production Retrospects and Prospects," *Advances in Agronomy*, 87:85-156 (2005).
Lam, "8 Analysis of Tissue-Specific Elements in the CaMV 35S Promoter," *Results Probl. Cell Differ.*, 20:181-196 (1994).
Last et al., "pEmu: an Improved Promoter for Gene Expression in Cereal Cells," *Theor. Appl. Genet.*, 81:581-588 (1991).
Lewis et al., "Three nicotine demethylase genes mediate nornicotine biosynthesis in *Nicotiana tabacum* L.: functional characterization of the CYP82E10 gene," Phytochemistry, 71(17-18):1988-1998 (2010).
Li et al, "A fast neutron deletion mutagenesis-based reverse genetic system for plants," The Plant Journal, 27 (3):235-242 (2001).
Li et al., "Modularly assembled designer TAL effector nucleases for targeted gene knockout and gene replacement in eukaryotes," Nucleic Acids Research, 39(14):6315-6325 (2011).
Lin-Hui et al., "OvereXpression of *Arabidopsis* NLP7 Improves Plant Growth Under Both Nitrogen-limiting and -sufficient Conditions by Enhancing Nitrogen and Carbon Assimilation," *Scientific Reports*, 6:27795, 1-13 (2016).
Matsuoka et al., "Tissue-Specific Light-Regulated Expression Directed by the Promoter of a $C_4$ Gene, Maize Pyruvate, Orthophosphate Dikinase, in a $C_3$ Plant, Rice," *Proc. Natl. Acad. Sci. USA*, 90(20):9586-9590 (1993).
Matsuyarna et al., "Characterization of glutamate decarboxylase mediating y-amino butyric acid increase in the early germination stage of soybean," Journal of Bioscience and Bioengineering 107 (5):538-543 (2009).
Mayo et al., "Genetic transformation of tobacco NT1 cells with Agrobacterium tumefaciencs," Nature Prototcols 1(3):1105-1111 (2006).
McCabe et al., "Stable Transformation of Soybean (Glycine Max) by Particle Acceleration," *Biotechnology*, 6:923-926 (1988).
McCallum et al., "Targeting Induced Local Lesions IN Genomes (TILLING) for Plant Functional Genomics," *Plant Physiol.*, 123:439-442 (2000).
McNellis et al., "Glucocorticoid-Inducible Expression of a Bacterial Avirulence Gene in Transgenic *Arabidopsis* Induces Hypersensitive Cell Death," *Plant J.* 14(2):247-257 (1998).
Odell et al., "Identification of DNA Sequences Required for Activity of the Cauliflower Mosaic Virus 35S Promoter," *Nature*, 313:810-812 (1985).

Orozco et al., "Localization of Light-Inducible and Tissue-Specific Regions of the Spinach Ribulose Bisphosphate Carboxylase/Oxygenase (subisco) Activase Promoter in Transgenic Tobacco Plants," *Plant Mol. Biol.*, 23(6):1129-1138 (1993).
Parizotto et al., "In vivo Investigation of the Transcription, Processing, Endonucleolytic Activity, and Functional Relevance of the Spatial Distribution of a Plant miRNA," *Genes Dev.*, 18:2237-2242 (2004).
Paszkowski et al., "Direct Gene Transfer to Plants," *EMBO J.*, 3(12):2717-2722 (1984).
Poehlman, "Breeding Field Crops," Van Nostrand Reinhold, New York (3.sup.rd ed.), (1987).
Porta et al., "Use of Viral Replicons for the Expression of Genes in Plants," *Molecular Biotechnology*, 5:209-221 (1996).
Reynolds et al., "Rational siRNA Design for RNA Interference," *Nature Biotechnol*, 22:326-330 (2004).
Riggs et al., "Stable Transformation of Tobacco by Electroporation: Evidence for Plasmid Concatenation," *Proc. Natl. Acad. Sci. USA*, 83:5602-5606 (1986).
Rigola et al., "High-Throughput Detection of Induced Mutations and Natural Variation Using KeyPointTM Technology," *PLoS One*, 4:e4761 (2009).
Rinehart et al., "Tissue-Specific and Developmental Regulation of Cotton Gene FbL2A," *Plant Physiol.*, 112(3):1331-1341 (1996).
Root et al., "Genome-scale loss-of-function screening with a lentiviral RNAi library," *Nature Methods*, 3(9):715-719 (2006).
Ruiter et al., "Spontaneous mutation frequency in plants obscures the effect of chimeraplasty," Plant Mol. Biol, 53(5):675-689 (2003).
Russell et al., "Tissue-Specific Expression in Transgenic Maize of Four Endosperm Promoters from Maize and Rice," *Transgenic Res.*, 6(2):157-168 (1997).
Schena et al., "A Steroid-Inducible Gene Expression System for Plant Cells," *Proc. Natl. Acad. Sci. USA*, 88:10421-10425 (1991).
Shen et al., "Modular nature of abscisic acid (ABA) response complexes: composite promoter units that are necessary and sufficient for ABA induction of gene expression in barley," Plant Cell, 8(7):1107-1119 (1996).
Shillito et al., "Direct Gene Transfer to Protoplasts of Dicotyledonous and Monocotyledonous Plants by a Number of Methods, Including Electroporation," *Meth. Enzymol.*, 153:313-336 (1987).
Singh et al., "Cytological Characterization of Transgenic Soybean," *Theor. Appl. Genet*, 96:319-324 (1998).
Tanaka et al., "Studies on Biological Effects of Ion Beams on Lethality, Molecular Nature of Mutation, Mutation Rate, and Spectrum of Mutation Phenotype for Mutation Breeding in Higher Plants," *J. Radiat. Res.*, 51:223-233 (2010).
Thompson et al., "CLUSTAL W: Improving the Sensitivity of Progressive Multiple Sequence Alignment through Sequence Weighting, Position-Specific Gap Penalties and Weight Matrix Choice," *Nucl. Acids Res.*, 22:4673-4680 (1994).
Tomes et al., "16 Direct DNA Transfer into Intact Plant Cells Via Microprojectile Bombardment," *Plant Cell, Tissue, and Organ Culture Fundamental Methods*, pp. 197-198 (1995).
USPTO Patent Trial and Appeal Board Decision on Motions (37 C.F.R. § 41.125(a)) Patent Interference No. 106,048, filed Feb. 15, 2017.
Vaeck et al., "Transgenic plants protected from insect attack," Nature, 328:33-37 (1987).
Van Camp et al., "Tissue-Specific Activity of Two Manganese Superoxide Dismutase Promoters in Transgenic Tobacco," *Plant Physiol.*, 112(2):525-535 (1996).
Velten et al., "Isolation of a Dual Plant Promoter Fragment from the Ti Plasmid of *Agrobacterium tumefaciens*," *EMBO J.*, 3:2723-2730 (1984).
Verkerk, "Chimerism of the Tomato Plant After Seed Irradiation with Fast Neutrons," *Neth. J. Agric. Sci.*, 19:197-203 (1971).
Weising et al., "Foreign Genes in Plants: Transfer, Structure, Expression, and Applications," *Annu. Rev. Genet.*, 22:421-477 (1988).
Wemsman, et al., "Principles of cultivar development" Chapter Seventeen: Tobacco., MacMillan Publishing Company, New York, 2:669-698 (1987).
Wilke et al., "Predicting the Tolerance of Proteins to Random Amino Acid Substitution," *Biophysical Journal*, 89:3714-3720 (2005).

(56) References Cited

OTHER PUBLICATIONS

Wright et al., "High-frequency homologous recombination in plants mediated by zinc-finger nucleases," The Plant Journal, 44:693-705 (2005).
Yamamoto et al., "Light-Responsive Elements of the Tobacco PSI-D Gene are Located both Upstream and within the Transcribed Region," *Plant J.*, 12(2):255-265 (1997).
Yamamoto et al., "The Promoter of a Pine Photosynthetic Gene Allows Expression of a js-Glucuronidase Reporter Gene in Transgenic Rice Plants in a Light-Independent but Tissue-Specific Manner," *Plant Cell Physiol.*, 35(5):773-778 (1994).
Yarce et al., "Forward Genetics Screening of Medicago truncatula Tnt1 Insertion Lines,"Legume Genomics: Methods and Protocols, *Methods in Molecular Biology*, 1069:93-100 (2013).
Yevtushenko et al., "Calcium/calmodulin activation of two divergent glutamate decarboxylases from tobacco," Journal of Experimental Botany, 54(389):2001-2002, Aug. 2003.
Yoo et al., "*Arabidopsis* mesophyll protoplasts: a versatile cell system for transient gene expression analysis," Nature Protocols 2(7):1565-1572, (2007).
Yu et al., "Overexpression of *Arabidopsis* NLP7 improves plant growth under both nitrogen-limiting and sufficient conditions by enhancing nitrogen and carbon assimilation," Scientific Reports 6(1):1-13 (2016).
Zhou et al. "The plant cyclin-dependent kinase inhibitor ICK1 has distinct functional domains for in vivo kinase inhibition, protein instability and nuclear localization," Plant Journal, 35(4):476-89. (2003).
Agrawal et al., "RNA interference: biology, mechanism, and applications," *Microbiology and Molecular Biology Reviews* 67.4, pp. 657-685 (Dec. 2003), available online: 10.1128/MMBR.67.4.657-685.2003.
Boutros et al., "Genome-wide RNAi analysis of growth and viability in *Drosophila* cells," *Science*, 303:832-835 (Feb. 2004) (electronic publication).
Buckingham et al., "RNA interference: from model organisms towards therapy for neural and neuromuscular disorders," *Human Molecular Genetics*, 13(2):R275-R288 (Jul. 2004).

Caldwell et al., "A structured mutant population for forward and reverse genetics in Barley (*Hordeum vulgare* L.)," *Plant Journal*, 40:143-150 (Jun. 2004).
Dietzl et al., "A genome-wide transgenic RNAi library for conditional gene inactivation in *Drosophila*," *Nature*, 448:151-156 (Jul. 2007).
"Draft for Diplomatic Conference for the Revision of the International Convention for the Protection of New Varieties of Plants," (of Dec. 2, 1961, as revised at Geneva on Nov. 10, 1972; on Oct. 23, 1978; and on Mar. 19, 1991),54 pages, March 4-19, 1991 (Geneva, Switzerland).
GenBank Accession No. AF352732.1 "Nicotiana tabacum glutamate decarboxylase isozyme 1 mRNA, complete cds." Mar. 17, 2001, 2 pages.
Goehring et al., "Screening and large-scale expression of membrane proteins in mammalian cells for structural studies," *Nat. Protoc.*, 9:2574-2585 (Oct. 2014).
Greene et al., "Spectrum of chemically induced mutations from a large-scale reverse-genetic screen in *Arabidopsis*," *Genetics*, 164:731-740 (Jun. 2003).
Kelley et al., "The Phyre2 web portal for protein modeling, prediction and analysis," *Nature Protocols*, 10:845-585 (May 2015).
Kumar et al., "Predicting the effects of coding non-synonymous variants on protein function using the SIFT algorithm," *Nature Protocols*, 4:1073-1082 (Jun. 2009).
Lee et al., "A systematic RNAi screen identifies a critical role for mitochondria in C. elegans longevity," *Nature Genetics*, 33:40-48 (Jan. 2003).
Schwarz et al., "MutationTaster2: mutation prediction for the deep-sequencing age," *Nature Methods*, 11:361-362 (Mar. 2014).
Sessions et al., "A High-Throughput *Arabidopsis* Reverse Genetics Screen," *Plant Cell*, 14:2985-2994 (Dec. 2002).
Sim et al., "SIFT web server: predicting effects of amino acid substitutions on proteins," *Nucleic Acids Research*, 40:W452-457 (May 2012).
Wolters & MacKeigan, "From sequence to function: using RNAi to elucidate mechanisms of human disease,"*Cell Death & Differentiation*, 15:809-819 (Jan. 2008).
Extended European Search Report issued in European Patent Application No. 232177493, dated May 28, 2024; 8 pages.

* cited by examiner

TOBACCO PLANTS HAVING INCREASED NITROGEN EFFICIENCY AND METHODS OF USING SUCH PLANTS

CROSS-REFERENCE TO RELATED APPLICATIONS AND INCORPORATION OF SEQUENCE LISTING

This application is a continuation of U.S. patent application Ser. No. 15/727,418, filed Oct. 6, 2017, which claims priority to U.S. Provisional Application No. 62/405,747, filed on Oct. 7, 2016, the disclosure of which is incorporated by reference in its entirety. which is incorporated by reference in its entirety herein. A sequence listing contained in the file named "P34627US02_SL.TXT" which is 83,381 bytes (measured in MS Windows®) and created on Jan. 26, 2022 is filed electronically herewith and incorporated by reference in its entirety.

TECHNICAL FIELD

This disclosure generally relates to tobacco plants.

BACKGROUND

Burley tobacco typically requires higher amounts of nitrogen fertilizer to provide the best yields. Maryland tobacco, on the other hand, requires approximately 25% of the level of nitrogen fertilizer typically used in growing burley tobacco. Fertilizer represents a significant cost in the cultivation of tobacco. Therefore, tobacco plants that have a nitrogen efficiency similar to that of Maryland tobacco are desirable.

SUMMARY

This disclosure provides a number of sequences involved in nitrogen utilization, methods of using such sequences, tobacco plants carrying modifications to such sequences, tobacco plants transgenic for such sequences, and tobacco products made from such plants.

In one aspect, a tobacco hybrid, variety, line, or cultivar is provided that includes plants having a mutation. As disclosed herein, such a mutation can be in one or more endogenous nucleic acids having a sequence selected from the group consisting of SEQ ID NOs: 1, 2, 5, 6, 9, 10, 13, 14, 17, and 18. In some embodiments, the plants exhibit an increase in yield relative to a plant lacking the mutation. In some embodiments, the plants exhibit a decrease in the amount and/or rate of chlorophyll loss relative to a plant lacking the mutation. In still another aspect, seed produced by such a tobacco hybrid, variety, line, or cultivar, where the seed includes the mutation in one or more endogenous nucleic acids having a sequence selected from the group consisting of SEQ ID NOs: 1, 2, 5, 6, 9, 10, 13, 14, 17, and 18.

In another aspect, a method of making a tobacco plant is provided. Such a method typically includes the steps of: inducing mutagenesis in *Nicotiana tabacum* cells to produce mutagenized cells; obtaining one or more plants from the mutagenized cells; and identifying at least one of the plants that comprises a mutation in one or more endogenous nucleic acids having a sequence selected from the group consisting of SEQ ID NOs: 1, 2, 5, 6, 9, 10, 13, 14, 17, and 18. Such a method further can include identifying at least one of the plants that exhibits an increase in yield relative to a plant lacking the mutation. Such a method further can include identifying at least one of the plants that exhibits a decrease in the amount and/or rate of chlorophyll loss relative to a plant lacking the mutation.

In one embodiment, mutagenesis is induced using a chemical mutagen or ionizing radiation. Representative chemical mutagens are selected from the group consisting of nitrous acid, sodium azide, acridine orange, ethidium bromide, and ethyl methane sulfonate (EMS). Representative ionizing radiation is selected from the group consisting of x-rays, gamma rays, fast neutron irradiation, and UV irradiation. In some embodiments, mutagenesis is induced using TALEN. In some embodiments, mutagenesis is induced using CRISPR/Cas9. In some embodiments, mutagenesis is induced using zinc-finger nuclease technology.

In another aspect, a method for producing a tobacco plant is provided. Such a method typically includes the steps of: crossing at least one plant of a first tobacco line with at least one plant of a second tobacco line, the plant of the first tobacco line having a mutation in one or more endogenous nucleic acids having a sequence selected from the group consisting of SEQ ID NOs: 1, 2, 5, 6, 9, 10, 13, 14, 17, and 18; and selecting for progeny tobacco plants that have the mutation. In some embodiments, such a method can further include selecting for progeny tobacco plants that exhibit an increase in yield relative to a plant lacking the mutation. In some embodiments, such a method can further include selecting for progeny tobacco plants that exhibit a decrease in the amount and/or rate of chlorophyll loss relative to a plant lacking the mutation.

In still another aspect, a tobacco product is provided that includes cured leaf from a tobacco plant having a mutation in one or more endogenous nucleic acids having a sequence selected from the group consisting of SEQ ID NOs: 1, 2, 5, 6, 9, 10, 13, 14, 17, and 18.

In yet another aspect, a method of producing a tobacco product is provided. Such a method typically includes providing cured leaf from a tobacco plant having a mutation in one or more endogenous nucleic acids having a sequence selected from the group consisting of SEQ ID NOs: 1, 2, 5, 6, 9, 10, 13, 14, 17, and 18; and manufacturing a tobacco product using the cured leaves. In one embodiment, the mutation is selected from the group consisting of a point mutation, an insertion, a deletion, and a substitution.

In one aspect, a transgenic tobacco plant is provided that includes a plant expression vector, wherein the plant expression vector comprises a nucleic acid molecule that is at least 25 nucleotides in length and has at least 91% sequence identity to a sequence selected from the group consisting of SEQ ID NOs: 1, 2, 5, 6, 9, 10, 13, 14, 17, and 18. In some embodiments, expression of the nucleic acid molecule results in plants exhibiting an increase in yield relative to a tobacco plant not expressing the nucleic acid molecule. In some embodiments, expression of the nucleic acid molecule results in plants exhibiting a decrease in the amount and/or rate of chlorophyll loss relative to a tobacco plant not expressing the nucleic acid molecule. In another aspect, seed produced by such a transgenic tobacco plant is provided, where the seed comprises the plant expression vector.

In another aspect, a transgenic tobacco plant is provided that includes a heterologous nucleic acid molecule of at least 25 nucleotides in length, wherein the nucleic acid molecule hybridizes under stringent conditions to a nucleic acid sequence selected from the group consisting of SEQ ID NOs: 1, 2, 5, 6, 9, 10, 13, 14, 17, and 18. In one embodiment, expression of the heterologous nucleic acid molecule results in plants exhibiting an increase in yield relative to a plant not expressing the nucleic acid molecule. In one embodiment, expression of the heterologous nucleic acid molecule results in plants exhibiting a decrease in the amount and/or rate of chlorophyll loss relative to a plant not expressing the nucleic acid molecule. In still another aspect, seed produced by such a transgenic tobacco plant is provided, wherein the seed comprises the heterologous nucleic acid molecule.

In still another aspect, leaf from a transgenic tobacco plant is provided that includes a vector, wherein the vector comprises a nucleic acid molecule having at least 91% sequence identity to 25 or more contiguous nucleotides of a nucleic acid sequence selected from the group consisting of SEQ ID NOs: 1, 2, 5, 6, 9, 10, 13, 14, 17, and 18. In some embodiments, expression of the nucleic acid molecule results in the leaf exhibiting an increase in yield relative to leaf from a tobacco plant not expressing the nucleic acid molecule. In some embodiments, expression of the nucleic acid molecule results in the leaf exhibiting a decrease in the amount and/or rate of chlorophyll loss relative to leaf from a tobacco plant not expressing the nucleic acid molecule.

In another aspect, a method of making a transgenic plant is provided that includes expressing a transgene in the plant, wherein the transgene encodes a double-stranded RNA molecule that inhibits expression from a nucleic acid sequence selected from the group consisting of SEQ ID NOs: 1, 2, 5, 6, 9, 10, 13, 14, 17, and 18, wherein the double-stranded RNA molecule comprises at least 25 consecutive nucleotides having 91% or greater sequence identity to a sequence selected from the group consisting of SEQ ID NOs: 1, 2, 5, 6, 9, 10, 13, 14, 17, and 18. In some embodiments, expression of the transgene results in leaf from the plant exhibiting an increase in yield relative to leaf from a plant not expressing the transgene. In some embodiments, expression of the transgene results in leaf exhibiting a decrease in the amount and/or rate of chlorophyll loss relative to leaf from a plant not expressing the nucleic acid molecule. In some embodiments, the double-stranded RNA molecule comprises a sequence selected from the group consisting of SEQ ID NOs: 4, 8, 12, 16, and 20.

In still another aspect, a method of decreasing the amount and/or rate of chlorophyll loss in a tobacco plant is provided that includes the steps of introducing a heterologous nucleic acid molecule operably linked to a promoter into tobacco cells to produce transgenic tobacco cells, wherein the heterologous nucleic acid molecule comprises at least 25 nucleotides in length and has at least 91% sequence identity to a nucleic acid sequence selected from the group consisting of SEQ ID NOs: 1, 2, 5, 6, 9, 10, 13, 14, 17, and 18; and regenerating transgenic tobacco plants from the transgenic tobacco cells, wherein the transgenic tobacco plants exhibit a decrease in the amount and/or rate of chlorophyll loss. Such a method can further include selecting at least one of the transgenic tobacco plants that exhibits an increase in yield relative to a tobacco plant not expressing the heterologous nucleic acid molecule.

In another aspect, cured tobacco leaf from a transgenic tobacco plant is provided that includes a vector, wherein the vector comprises a nucleic acid molecule having at least 91% sequence identity to 25 or more contiguous nucleotides of a nucleic acid sequence such as SEQ ID NOs: 1, 2, 5, 6, 9, 10, 13, 14, 17, and 18. In some embodiments, the nucleic acid molecule has at least 95% sequence identity to SEQ ID NOs: 1, 2, 5, 6, 9, 10, 13, 14, 17, and 18. In some embodiments, the nucleic acid molecule has at least 99% sequence identity to SEQ ID NOs: 1, 2, 5, 6, 9, 10, 13, 14, 17, and 18. In some embodiments, the nucleic acid is in sense orientation. In some embodiments, the nucleic acid is in antisense orientation.

In still another aspect, a transgenic tobacco plant is provided that includes a plant expression vector, wherein the expression vector comprises a nucleic acid molecule having at least 95% sequence identity to a sequence selected from the group consisting of SEQ ID NOs: 1, 2, 5, 6, 9, 10, 13, 14, 17, and 18, or a fragment of any of those sequences encoding a functional polypeptide. In some embodiments, expression of the nucleic acid molecule or a functional fragment thereof results in plants exhibiting an increase in yield relative to tobacco plant not expressing the nucleic acid molecule or functional fragment thereof. In one aspect, seed produced by such a transgenic tobacco plant is provided that includes the expression vector.

In yet another aspect, a transgenic tobacco plant is provided that includes a heterologous nucleic acid molecule, wherein the nucleic acid molecule hybridizes under stringent conditions to a nucleic acid sequence selected from the group consisting of SEQ ID NOs: 1, 2, 5, 6, 9, 10, 13, 14, 17, and 18, or a fragment thereof encoding a functional polypeptide. In one embodiment, expression of the heterologous nucleic acid molecule or functional fragment thereof results in plants exhibiting an increase in yield relative to a tobacco plant not expressing the nucleic acid molecule or functional fragment thereof. In one aspect, seed produced by such a transgenic tobacco plant is provided that includes the heterologous nucleic acid molecule.

In one aspect, leaf from a transgenic tobacco plant is provided that includes a vector, wherein the vector comprises a nucleic acid molecule having at least 95% sequence identity to a nucleic acid sequence selected from the group consisting of SEQ ID NOs: 1, 2, 5, 6, 9, 10, 13, 14, 17, and 18, or a fragment thereof encoding a functional polypeptide. In one embodiment, expression of the nucleic acid molecule or functional fragment thereof results in the leaf exhibiting a decrease in the amount and/or rate of chlorophyll loss relative to leaf from a tobacco plant not expressing the nucleic acid molecule or functional fragment thereof. In one embodiment, expression of the nucleic acid molecule or functional fragment thereof results in the leaf exhibiting an increase in yield relative to leaf from a tobacco plant not expressing the nucleic acid molecule or functional fragment thereof.

In another embodiment, a method of decreasing the amount and/or rate of chlorophyll loss in a tobacco plant is provided. Such a method typically includes the steps of introducing a heterologous nucleic acid molecule operably linked to a promoter into tobacco cells to produce transgenic tobacco cells, wherein the heterologous nucleic acid molecule has at least 95% sequence identity to a nucleic acid sequence selected from the group consisting of SEQ ID NOs: 1, 2, 5, 6, 9, 10, 13, 14, 17, and 18, or a fragment thereof encoding a functional polypeptide; and regenerating transgenic tobacco plants from the transgenic tobacco cells, wherein the transgenic tobacco plants exhibit a decrease in the amount and/or rate of chlorophyll loss.

Such a method can further include selecting at least one of the transgenic tobacco plants that exhibits a decrease in the amount and/or rate of chlorophyll loss relative to a tobacco plant not expressing the heterologous nucleic acid molecule or functional fragment thereof. Representative methods for introducing the heterologous nucleic acid molecule into the tobacco cells using particle bombardment, *Agrobacterium*-mediated transformation, microinjection, polyethylene glycol-mediated transformation, liposome-mediated DNA uptake, or electroporation.

In still another aspect, cured tobacco leaf from a transgenic tobacco plant is provided that includes a vector, wherein the vector comprises a nucleic acid molecule having at least 95% sequence identity to a nucleic acid sequence selected from the group consisting of SEQ ID NOs: 1, 2, 5, 6, 9, 10, 13, 14, 17, and 18, or a fragment thereof encoding a functional polypeptide.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
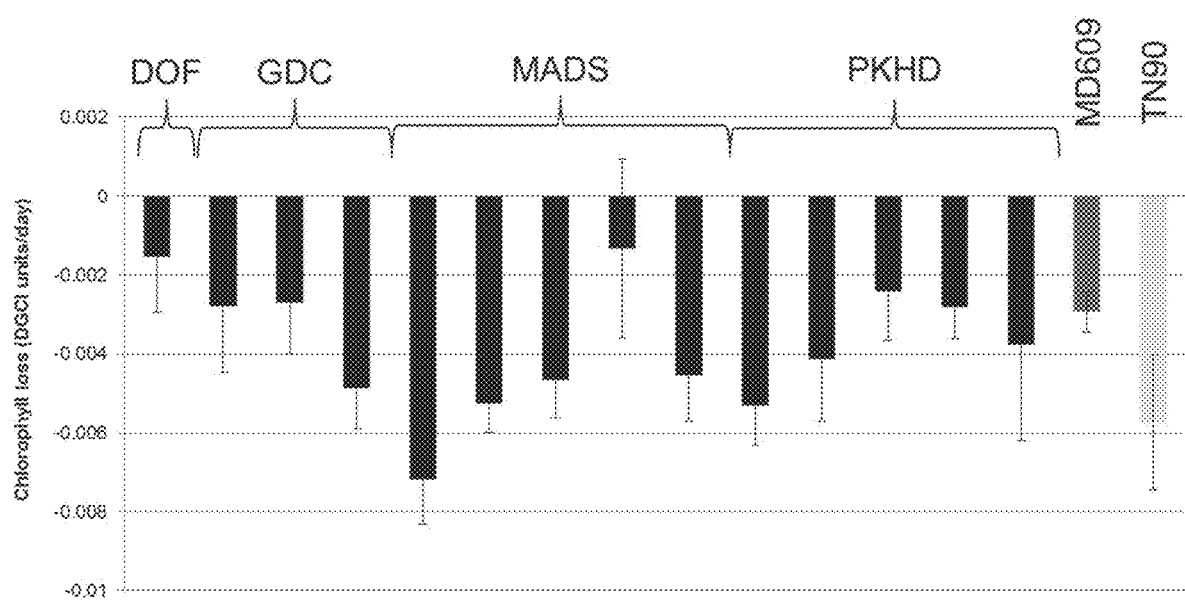
FIG. 1 is a graph showing chlorophyll loss in transgenic plants.

This disclosure provides nucleic acids from *N. tabacum* that encode polypeptides associated with nitrogen use. Such nucleic acids, SEQ ID NOs: 1, 2, 5, 6, 9, 10, 13, 14, 17, and 18, and the polypeptides encoded thereby, SEQ ID NOs: 3, 7, 11, 15, and 19, are described and characterized herein. As described herein, the level of expression of such nucleic acid sequences and/or the function of such polypeptides can be modulated in *N. tabacum* and the resulting effect on nitrogen utilization in plants can be evaluated. Modulating polypeptide function and/or genes expression can result in an increase in yield and a decrease in the amount and/or rate of chlorophyll loss in tobacco and resulting tobacco products.

Nucleic Acids and Polypeptides

Nucleic acids are provided herein (see, for example, SEQ ID NOs: 1, 2, 5, 6, 9, 10, 13, 14, 17, and 18). As used herein, nucleic acids can include DNA and RNA, and includes nucleic acids that contain one or more nucleotide analogs or backbone modifications. A nucleic acid can be single stranded or double stranded, which usually depends upon its intended use. The nucleic acids provided herein encode polypeptides (see, for example, SEQ ID NOs: 3, 7, 11, 15, and 19).

Also provided are nucleic acids and polypeptides that differ from SEQ ID NOs: 1, 2, 5, 6, 9, 10, 13, 14, 17, and 18 and SEQ ID NOs: 3, 7, 11, 15, and 19. Nucleic acids and polypeptides that differ in sequence from SEQ ID NOs: 1, 2, 5, 6, 9, 10, 13, 14, 17, and 18 and SEQ ID NOs: 3, 7, 11, 15, and 19, can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NOs: 1, 2, 5, 6, 9, 10, 13, 14, 17, and 18 and SEQ ID NOs: 3, 7, 11, 15, and 19.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NOs: 1, 2, 5, 6, 9, 10, 13, 14, 17, and 18), thereby leading to changes in the amino acid sequence of the encoded polypeptide (e.g., SEQ ID NOs: 3, 7, 11, 15, and 19). For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6× His tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame). Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are pre-hybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2× SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, CA).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Certain of the nucleic acids described herein (e.g., SEQ ID NO:1 and 2) are predicted to encode a polypeptide (e.g., SEQ ID NO:3) that belong to the "DNA-binding One Zinc Finger" (Dof) family of sequences. "Dof zinc finger" proteins are a particular class of zinc finger domain transcription factors (TFs) characterized by a conserved region of 50 amino acids with a C2-C2 finger structure, which binds specifically to 5'-T/AAAAG-3' DNA sequences. Dof proteins have been reported to participate in the regulation of gene expression in processes such as seed germination and seed storage protein synthesis in developing endosperm, light regulation of genes involved in carbohydrate metabolism, plant defense mechanisms, and auxin response.

Certain of the nucleic acids described herein (e.g., SEQ ID NOs:5 and 6) are predicted to encode a polypeptide (e.g., SEQ ID NO:7) that belong to the "protein TIC 22-like" family of sequences. The "protein TIC 22-like" family of polypeptides is involved in protein precursor import into chloroplasts. See, for example, UniProt F4J469 and Q9ZST9. See also, for example, Kouranov et al. (1998, J. Cell Biol., 143:991-1002) and Kouranov & Schnell (1997, J. Cell Biol., 139:1677-85).

Certain of the nucleic acids described herein (e.g., SEQ ID NOs:9 and 10) are predicted to encode a polypeptide (e.g., SEQ ID NO:11) that belong to the glutamate decarboxylase family of sequences. Glutamate decarboxylase (EC 4.1.1.15) catalyzes the decarboxylation of glutamate to GABA and carbon dioxide, using PLP as a co-factor. See, for example, UniProt Q42521 and Q7XJB3. See also, for example, Gut et al. (2009, J. Mol. Biol., 392:334-51) and Matsuyama et al. (2009, J. Biosci. Bioeng., 107:538-43).

Certain of the nucleic acids described herein (e.g., SEQ ID NOs:13 and 14) are predicted to encode a polypeptide (e.g., SEQ ID NO:15) that belong to the "mads-box TF 27-like" family of sequences. Mads-box transcription factors typically contain a highly conserved 58 amino acid long DNA binding MADS domain, and have been shown to be expressed in vegetative tissues, ovule, embryo, root and fruit, suggesting a diverse role in plant development. See, for example, XM_008671095 and XM_008671096. See also, for example, Kumar et al. (2016, Sci. Reports, 6:20695).

Certain of the nucleic acids described herein (e.g., SEQ ID NOs:17 and 18) are predicted to encode a polypeptide (e.g., SEQ ID NO:19) that belong to the PKHD-type hydroxylase family of sequences. The PKHD-type hydroxylase family (EC 1.14.11.-) typically possesses dioxygenase activity and binds iron ions and L-ascorbic acid. See, for example, UniProt Q3ED68.

Plants Having Increased Yield and Decreased Yellowing and Methods of Making

Tobacco hybrids, varieties, lines, or cultivars are provided that have a mutation in one or more endogenous nucleic acids described herein (e.g., SEQ ID NOs: 1, 2, 5, 6, 9, 10, 13, 14, 17, and 18). As described herein, leaf from plants having a mutation in one or more of the endogenous nucleic acids (e.g., SEQ ID NOs: 1, 2, 5, 6, 9, 10, 13, 14, 17, or 18) can exhibit an increase in yield or a decrease in the amount and/or rate of chlorophyll loss (e.g., compared to a plant that lacks the mutation). In addition, plants having a mutation in one or more of the endogenous nucleic acids (e.g., SEQ ID NOs: 1, 2, 5, 6, 9, 10, 13, 14, 17, or 18) can exhibit an increase in yield or a decrease in the amount and/or rate of chlorophyll loss (e.g., compared to a plant lacking the mutation).

It would be understood by a skilled artisan that a mutation in a nucleic acid (e.g., SEQ ID NOs: 1, 2, 5, 6, 9, 10, 13, 14, 17, or 18) may or may not be reflected in the encoded polypeptide sequence (e.g., SEQ ID NOs: 3, 7, 11, 15, or 19). For example, a mutant nucleic acid sequence can encode a mutant polypeptide sequence (e.g., truncated, functionally impaired), or a mutant nucleic acid sequence can encode a wild type polypeptide that is, for example, abnormally expressed (e.g., a reduced amount or improperly located polypeptide relative to the polypeptide encoded by the non-mutant nucleic acid sequence (e.g., a wild type nucleic acid sequence).

Methods of making a tobacco plant having a mutation are known in the art. Mutations can be random mutations or targeted mutations. For random mutagenesis, cells (e.g., *Nicotiana tabacum* cells) can be mutagenized using, for example, a chemical mutagen, ionizing radiation, or fast neutron bombardment (see, e.g., Li et al., 2001, *Plant J.*, 27:235-42). Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, *Nucleic Acids Res.*, 39(14):6315-25) or zinc-finger (see, for example, Wright et al., 2005, *The*

*Plant J.,* 44:693-705). Whether random or targeted, a mutation can be a point mutation, an insertion, a deletion, a substitution, or combinations thereof.

Conserved domains in polypeptides can be important for polypeptide function as well as cellular or subcellular location. As discussed herein, one or more nucleotides can be mutated to alter the expression and/or function of the encoded polypeptide, relative to the expression and/or function of the corresponding wild type polypeptide. It will be appreciated, for example, that a mutation in one or more highly conserved regions would likely alter polypeptide function, while a mutation outside of a conserved region would likely have little to no effect on polypeptide function. In addition, a mutation in a single nucleotide can create a stop codon, which would result in a truncated polypeptide and, depending on the extent of truncation, loss-of-function.

Preferably, a mutation in one of the nucleic acids disclosed herein results in reduced or even complete elimination of protein activity. Suitable types of mutations in a coding sequence include, without limitation, insertions of nucleotides, deletions of nucleotides, or transitions or transversions in the wild-type coding sequence. Mutations in the coding sequence can result in insertions of one or more amino acids, deletions of one or more amino acids, and/or non-conservative amino acid substitutions in the encoded polypeptide. In some cases, the coding sequence can include more than one mutation or more than one type of mutation.

Insertion or deletion of amino acids in a coding sequence, for example, can disrupt the conformation of the encoded polypeptide. Amino acid insertions or deletions also can disrupt sites important for recognition of a binding ligand or for activity of the polypeptide. It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the polypeptide in the cell, introduce a stop codon to produce a truncated polypeptide, or disrupt an active site or domain (e.g., a catalytic site or domain, a binding site or domain) within the polypeptide.

Non-conservative amino acid substitutions can replace an amino acid of one class with an amino acid of a different class. Non-conservative substitutions can make a substantial change in the charge or hydrophobicity of the polypeptide. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Transmembrane polypeptides contain particular sequences that determine where the polypeptide is localized within the cell. The target peptide sequences often are cleaved (e.g., by specific proteases that recognize a specific nucleotide motif) after the polypeptide is inserted into the membrane. By mutating the target sequence or a cleavage motif, the targeting of the polypeptide can be altered.

Following mutagenesis, $M_0$ plants are regenerated from the mutagenized cells and those plants, or a subsequent generation of that population (e.g., $M_1$, $M_2$, $M_3$, etc.), can be screened for a mutation in a sequence of interest (e.g., SEQ ID NOs: 1, 2, 5, 6, 9, 10, 13, 14, 17, and 18). Screening for plants carrying a mutation in a sequence of interest can be performed using methods routine in the art (e.g., hybridization, amplification, combinations thereof) or by evaluating the phenotype (e.g., an increase in yield or a decrease in the amount and/or rate of chlorophyll loss). Generally, the presence of a mutation in one or more of the nucleic acid sequences disclosed herein (e.g., SEQ ID NOs: 1, 2, 5, 6, 9, 10, 13, 14, 17, and 18) results in an increase in yield or a decrease in the amount and/or rate of chlorophyll loss compared to a corresponding plant (e.g., having the same varietal background) lacking the mutation.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype. Such plants may be heterozygous and exhibit a mutant phenotype due to a phenomenon such as dominant negative suppression, despite the presence of the wild type allele, or such plants may be homozygous due to independently induced mutations in both alleles.

A tobacco plant carrying a mutant allele can be used in a plant breeding program to create novel and useful cultivars, lines, varieties and hybrids. Thus, in some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Breeding is carried out using known procedures. DNA fingerprinting, SNP or similar technologies may be used in a marker-assisted selection (MAS) breeding program to transfer or breed mutant alleles into other tobaccos, as described herein. Progeny of the cross can be screened for a mutation using methods described herein, and plants having a mutation in a nucleic acid sequence disclosed herein (e.g., SEQ ID NOs: 1, 2, 5, 6, 9, 10, 13, 14, 17, and 18) can be selected. For example, plants in the $F_2$ or backcross generations can be screened using a marker developed from a sequence described herein or a fragment thereof, using one of the techniques listed herein. Progeny plants also can be screened for an increase in yield or a decrease in the amount and/or rate of chlorophyll loss, and the desired plants, compared to a corresponding plant that lacks the mutation, can be selected. Plants identified as possessing the mutant allele and/or the mutant phenotype can be backcrossed or self-pollinated to create a second population to be screened. Backcrossing or other breeding procedures can be repeated until the desired phenotype of the recurrent parent is recovered.

Successful crosses yield $F_1$ plants that are fertile and that can be backcrossed with one of the parents if desired. In some embodiments, a plant population in the $F_2$ generation is screened for the mutation or variant gene expression using standard methods (e.g., PCR with primers based upon the nucleic acid sequences disclosed herein). Selected plants are then crossed with one of the parents and the first backcross (BC$_1$) generation plants are self-pollinated to produce a BC$_1$F$_2$ population that is again screened for variant gene expression. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the mutation and exhibits variant gene expression. Breeder's seed of the selected plant can be produced using standard methods including, for example, field testing, confirmation of the null condition, and/or chemical analyses of leaf to determine chlorophyll loss.

The result of a plant breeding program using the mutant tobacco plants described herein are novel and useful cultivars, varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it confirms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Tobacco hybrids can be produced by preventing self-pollination of female parent plants (i.e., seed parents) of a first variety, permitting pollen from male parent plants of a second variety to fertilize the female parent plants, and allowing F$_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful. In embodiments in which the female parent plants are CMS, the male parent plants typically contain a fertility restorer gene to ensure that the F$_1$ hybrids are fertile. In other embodiments in which the female parents are CMS, male parents can be used that do not contain a fertility restorer. F$_1$ hybrids produced from such parents are male sterile. Male sterile hybrid seed can be interplanted with male fertile seed to provide pollen for seed-set on the resulting male sterile plants.

Varieties, lines and cultivars described herein can be used to form single-cross tobacco F$_1$ hybrids. In such embodiments, the plants of the parent varieties can be grown as substantially homogeneous adjoining populations to facilitate natural cross-pollination from the male parent plants to the female parent plants. The F$_2$ seed formed on the female parent plants is selectively harvested by conventional means. One also can grow the two parent plant varieties in bulk and harvest a blend of F$_1$ hybrid seed formed on the female parent and seed formed upon the male parent as the result of self-pollination. Alternatively, three-way crosses can be carried out wherein a single-cross F$_1$ hybrid is used as a female parent and is crossed with a different male parent. As another alternative, double-cross hybrids can be created wherein the F$_1$ progeny of two different single-crosses are themselves crossed. Self-incompatibility can be used to particular advantage to prevent self-pollination of female parents when forming a double-cross hybrid.

The tobacco plants used in the methods described herein can be a Burley type, a dark type, a flue-cured type, a Maryland type, or an Oriental type. The tobacco plants used in the methods described herein typically are from *N. tabacum*, and can be from any number of *N. tabacum* varieties. A variety can be BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

In addition to mutation, another way in which nitrogen utilization can be increased is by using inhibitory RNAs (e.g., RNAi). Therefore, transgenic tobacco plants are provided that contain a transgene encoding at least one RNAi molecule, which, when expressed, silences at least one of the endogenous nucleic acids described herein (e.g., SEQ ID NOs: 1, 2, 5, 6, 9, 10, 13, 14, 17, and 18). As described herein, leaf from such transgenic plants exhibit an increase in yield (e.g., compared to leaf from a plant lacking or not expressing the RNAi). In addition, leaf from such transgenic plants exhibit a decrease in the amount and/or rate of chlorophyll loss (e.g., compared to leaf from a plant lacking or not expressing the RNAi).

RNAi technology is known in the art and is a very effective form of post-transcriptional gene silencing. RNAi molecules typically contain a nucleotide sequence (e.g., from about 18 nucleotides in length (e.g., about 19 or 20 nucleotides in length) up to about 700 nucleotides in length) that is complementary to the target gene in both the sense and antisense orientations. The sense and antisense strands can be connected by a short "loop" sequence (e.g., about 5 nucleotides in length up to about 800 nucleotides in length) and expressed in a single transcript, or the sense and antisense strands can be delivered to and expressed in the target cells on separate vectors or constructs. A number of companies offer RNAi design and synthesis services (e.g., Life Technologies, Applied Biosystems).

The RNAi molecule typically is at least 25 nucleotides in length and has at least 91% sequence identity (e.g., at least 95%, 96%, 97%, 98% or 99% sequence identity) to one of the nucleic acid sequences disclosed herein (e.g., SEQ ID NOs: 1, 2, 5, 6, 9, 10, 13, 14, 17, and 18) or hybridizes under stringent conditions to one of the nucleic acid sequences disclosed herein (e.g., SEQ ID NOs: 1, 2, 5, 6, 9, 10, 13, 14, 17, and 18). The RNAi molecule can be expressed using a plant expression vector, and hybridization under stringent conditions is described above. Representative RNAi molecules to a number of the novel sequences described herein are provided in SEQ ID NOs: 4, 8, 12, 16, or 20.

Methods of introducing a nucleic acid (e.g., a heterologous nucleic acid) into plant cells are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols*, 2(7):1565-72)), liposome-mediated DNA uptake, or electroporation. Following transformation, the transgenic plant cells can be regenerated into transgenic tobacco plants. As described herein, expression of the transgene results in plants that exhibit an increase in yield or a decrease in the amount and/or rate of chlorophyll loss relative to a plant not expressing the transgene. The regenerated transgenic plants can be screened for an increase in yield or a decrease in the amount and/or rate of chlorophyll loss, compared to the amount in a corresponding non-transgenic plant. In addition, a regenerated transgenic plant having an increase in yield or a decrease in the amount and/or rate of chlorophyll loss can be selected for use in, for example, a breeding program as discussed herein.

It would be understood by the skilled artisan that yield, with respect to tobacco, refers to leaf dry matter, leaf number, leaf surface area, leaf thickness, and/or total dry matter. As used herein, an increase in yield refers to an increase (e.g., a statistically significant increase) in the yield of tobacco plants by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-grown tobacco plants lacking the mutation or the transgene or relative to TN90. As used herein, statistical significance refers to a p-value of less than 0.05, e.g., a p-value of less than 0.025 or a p-value of less than 0.01, using an appropriate measure of statistical significance, e.g., a one-tailed two sample t-test.

Loss of chlorophyll due to its breakdown is a regular process that occurs in leaves during senescence. See, for example, Hortensteiner & Krautler (2011, Biochim. Biophys. Acta, 1807:977-88). As used herein, a decrease in the amount and/or rate of chlorophyll loss refers to a decrease (e.g., a statistically significant decrease) in the amount and/or rate of chlorophyll loss in tobacco plants (e.g., tobacco leaf) by about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-grown tobacco lacking the mutation or the transgene or relative to TN90. As used herein, statistical significance refers to a p-value of less than 0.05, e.g., a p-value of less than 0.025 or a p-value of less than 0.01, using an appropriate measure of statistical significance, e.g., a one-tailed two sample t-test. Chlorophyll, and, therefore, the loss of chlorophyll, can be measured by using a SPAD meter, which measures the specific absorbance of chlorophyll, or by measuring the green coloration in the leaf by image analysis algorithms.

Nucleic acids that confer traits such as herbicide resistance (sometimes referred to as herbicide tolerance), insect resistance, or stress tolerance, can also be present in the tobacco plants described herein. Genes conferring resistance to an herbicide that inhibits the growing point or meristem, such as an imidazolinone or a sulfonylurea, can be suitable. Exemplary genes in this category encode mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS), which is resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides.

Genes for resistance to glyphosate also are suitable. See, for example, U.S. Pat. Nos. 4,940,835 and 4,769,061. Such genes can confer resistance to glyphosate herbicidal compositions, including, without limitation, glyphosate salts such as the trimethylsulphonium salt, the isopropylamine salt, the sodium salt, the potassium salt and the ammonium salt. See, e.g., U.S. Pat. Nos. 6,451,735 and 6,451,732. Genes for resistance to phosphono compounds such as glufosinate ammonium or phosphinothricin, and pyridinoxy or phenoxy propionic acids and cyclohexones also are suitable. See, e.g., U.S. Pat. Nos. 5,879,903; 5,276,268; and 5,561,236; and European Application No. 0 242 246.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Pat. No. 6,084,155 and US 2001/0016956.

A number of genes are available that confer resistance to insects, for example, insects in the order Lepidoptera. Exemplary genes include those that encode truncated Cry1A(b) and Cry1A(c) toxins. See, e.g., genes described in U.S. Pat. Nos. 5,545,565; 6,166,302; and 5,164,180. See also, Vaeck et al., 1997, *Nature*, 328:33-37 and Fischhoff et al., 1987, *Nature Biotechnology*, 5:807-813. Particularly useful are genes encoding toxins that exhibit insecticidal activity against *Manduca sexta* (tobacco hornworm); *Heliothis virescens* Fabricius (tobacco budworm) and/or *S. litura* Fabricius (tobacco cutworm).

In addition to mutation and RNAi, another way in which nitrogen utilization can be increased is by overexpressing one or more nucleic acid molecules. The sequences described herein can be overexpressed in plants to an increase in yield or a decrease in the amount and/or rate of chlorophyll loss. Therefore, transgenic tobacco plants, or leaf from such plants, are provided that are transformed with a nucleic acid molecule described herein (e.g., SEQ ID NOs: 1, 2, 5, 6, 9, 10, 13, 14, 17, and 18) or a functional fragment thereof under control of a promoter that is able to drive expression in plants (e.g., a plant promoter). As discussed herein, a nucleic acid molecule used in a plant expression vector can have a different sequence than a sequence described herein, which can be expressed as a percent sequence identity (e.g., relative to SEQ ID NOs: 1, 2, 5, 6, 9, 10, 13, 14, 17, and 18) or based on the conditions under which the sequence hybridizes to SEQ ID NOs: 1, 2, 5, 6, 9, 10, 13, 14, 17, and 18.

As an alternative to using a full-length sequence, a portion of the sequence can be used that encodes a polypeptide fragment having the desired functionality (referred to herein as a "functional fragment"). When used with respect to nucleic acids, it would be appreciated that it is not the nucleic acid fragment that possesses functionality but the encoded polypeptide fragment. Based on the disclosure herein, one of skill in the art can predict or readily identify the portion(s) of a polypeptide (e.g., one or more domains) that may impart the desired functionality.

Following transformation, the transgenic tobacco cells can be regenerated into transgenic tobacco plants. The regenerated tobacco plants can be screened for an increase in yield or a decrease in the amount and/or rate of chlorophyll loss, and plants having an increase in yield or a decrease in the amount and/or rate of chlorophyll loss, compared to the amount in a corresponding non-transgenic plant, can be selected and used, for example, in a breeding program as discussed herein. Expression of the nucleic acid molecule or a functional fragment thereof may result in tobacco plants that exhibit an increase in yield or a decrease in the amount and/or rate of chlorophyll loss compared to a tobacco plant that does not express the nucleic acid molecule or functional fragment thereof. Nucleic acids conferring herbicide resistance, insect resistance, or stress tolerance, can also be introduced into such tobacco plants.

Tobacco Products and Methods of Making

The methods described herein allow for tobacco plants to be produced that exhibit an increase in yield or a decrease in the amount and/or rate of chlorophyll loss. As described herein, such methods can include mutagenesis (e.g., random or targeted) or the production of transgenic plants (using, e.g., RNAi or overexpression).

Leaf from such tobacco (e.g., exhibiting an increase in yield or a decrease in the amount and/or rate of chlorophyll loss) can be cured, aged, conditioned, and/or fermented. Methods of curing tobacco are well known and include, for example, air curing, fire curing, flue curing and sun curing. Aging also is known and is typically carried out in a wooden drum (e.g., a hogshead) or cardboard cartons in compressed conditions for several years (e.g., 2 to 5 years), at a moisture content of from about 10% to about 25% (see, for example, U.S. Pat. Nos. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993, 4,660,577, 4,848,373 and 5,372,149. The tobacco also can be further processed (e.g., cut, expanded, blended, milled or comminuted), if desired, and used in a tobacco product.

Tobacco products are known in the art and include any product made or derived from tobacco that is intended for adult human consumption, including any component, part, or accessory of a tobacco product. Representative tobacco products include, without limitation, cigarettes, smokeless tobacco products, tobacco-derived nicotine products, cigarillos, non-ventilated recess filter cigarettes, vented recess filter cigarettes, cigars, snuff, e-vapor products, pipe tobacco, cigar tobacco, cigarette tobacco, chewing tobacco, leaf tobacco, shredded tobacco, and cut tobacco. Representative smokeless tobacco products include, for example, chewing tobacco, snus, pouches, films, tablets, coated dowels, rods, and the like. Representative cigarettes and other smoking articles include, for example, smoking articles that include filter elements or rod elements, where the rod element of a smokeable material can include cured tobacco within a tobacco blend. In addition to the reduced-alkaloid tobacco described herein, tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Tobacco with Decreased Nitrogen Requirements

Burley tobacco is considered to be nitrogen inefficient whereas a related type of tobacco, Maryland, is grown with much less fertilizer. This fact was utilized to determine the cause of nitrogen use efficiency in Maryland tobacco and to translate these findings to burley tobacco. Gene expression and metabolite analysis of TN90 and Maryland tobacco were also used to find metabolic pathways for possible manipulation in burley tobacco and to find molecular markers for the Maryland phenotype. These markers also can be used to compare burley tobacco with other nitrogen use efficient tobacco varieties and *Nicotiana* species for future breeding stocks.

Example 2

Analysis of Gene Expression Levels

In order to determine the genetic basis for the nitrogen utilization efficiency observed in Maryland tobacco, gene expression in roots and leaves of both Md609 and TN90 tobacco were analyzed. Briefly, seedlings of both types of tobacco were grown without added nitrogen for 4 weeks. Plants were then grown on 25% nitrogen for up to 8 weeks with samples of roots and leaves being taken at multiple time points. RNA was extracted from both the roots and leaves and sequenced on an Illumina Next-Gen sequencing platform. RNA-seq gene expression analysis was done using the previously obtained genome information from the sequencing of TN90. Gene expression analysis identified 5 genes that would be predicted to affect the nitrogen use efficiency in burley tobacco. These genes are listed, along with their expression level in TN90 and Maryland tobacco, in Tables 1, 2 and 3.

TABLE 1

Sequences

| Gene Designation | Homology | Coding Sequence (SEQ ID NO) | Gene Sequence (SEQ ID NO) | Protein Sequence (SEQ ID NO) | Overexpression/ RNAi (SEQ ID NO) |
|---|---|---|---|---|---|
| g80368_Scaffold0001709 | dof zinc finger | 1 | 2 | 3 | 4 |
| g75333_Scaffold0001539 | protein TIC 22-like | 5 | 6 | 7 | 8 |
| g1645_Scaffold0000011 | glutamate decarboxylase | 9 | 10 | 11 | 12 |
| g173910_Scaffold0007958 | mads-box TF 27-like | 13 | 14 | 15 | 16 |
| g112803_Scaffold0003083 | PKHD-type hydroxylase | 17 | 18 | 19 | 20 |

TABLE 2

Leaf Expression at 25% Fertilization Rate

| Gene Designation | Homology | TN90 Time 0 | TN90 1 wk | TN90 4 wks | TN90 8 wks | Md609 Time 0 | Md609 1 wk | Md609 4 wks | Md609 8 wks |
|---|---|---|---|---|---|---|---|---|---|
| g112803_Scaffold0003083 | PKHD-type hydroxylase | 6.45 | 10.77 | 11.10 | 7.36 | 0.00 | 0.00 | 0.00 | 0.00 |
| g1645_Scaffold0000011 | glutamate decarboxylase | 27.54 | 20.40 | 19.18 | 22.85 | 2.31 | 2.87 | 0.87 | 1.22 |
| g173910_Scaffold0007958 | mads-box TF 27-like | 20.37 | 21.44 | 20.47 | 6.45 | 50.99 | 53.41 | 72.87 | 21.19 |
| g75333_Scaffold0001539 | protein TIC 22-like | 3.21 | 5.27 | 3.53 | 2.51 | 29.60 | 109.12 | 39.51 | 35.59 |
| g80368_Scaffold0001709 | dof zinc finger | 2.04 | 2.49 | 6.20 | 1.00 | 2.89 | 0.34 | 2.74 | 1.29 |

TABLE 3

Root Expression at 25% Fertilization Rate

| Gene Designation | Homology | TN90 Time 0 | TN90 1 wk | TN90 4 wks | TN90 8 wks | Md609 Time 0 | Md609 1 wk | Md609 4 wks | Md609 8 wks |
|---|---|---|---|---|---|---|---|---|---|
| g112803_Scaffold0003083 | PKHD-type hydroxylase | 9.78 | 11.55 | 8.74 | 13.97 | 0.00 | 0.00 | 0.00 | 0.00 |
| g1645_Scaffold0000011 | glutamate decarboxylase | 37.05 | 21.74 | 24.89 | 26.26 | 2.02 | 1.10 | 0.75 | 0.29 |
| g173910_Scaffold0007958 | mads-box TF 27-like | 14.36 | 8.35 | 10.01 | 16.33 | 69.64 | 13.40 | 34.55 | 17.25 |
| g75333_Scaffold0001539 | protein TIC 22-like | 2.59 | 2.52 | 2.83 | 4.45 | 29.46 | 57.61 | 56.56 | 66.56 |
| g80368_Scaffold0001709 | dof zinc finger | 23.19 | 13.24 | 16.72 | 17.72 | 55.43 | 13.10 | 44.41 | 20.45 |

Example 3

Metabolite Profiling for Nitrogen Use Efficiency Marker Development

Metabolite analysis was done in parallel to determine the flux of nitrogen through the metabolic pathways and relate this to the gene expression data. Shotgun metabolomics using a combination of UHPLC-MS/MS and GC-MS was done by Metabolon Inc. Relative levels of 616 compounds from leaves and 771 compounds from roots were evaluated. Only a subset of these compounds could be identified with high confidence (359 compounds from leaf and 449 compounds from root). Relevant metabolites were used to validate the gene expression differences and to determine possible markers for the Maryland phenotype.

The metabolite profiles that were generated were used to develop a panel of molecular markers that could be used to define the Maryland phenotype and for further quantitative trait loci discovery. These markers mostly relate to nitrogen assimilation and storage. One set of markers was determined to be applicable to the nitrogen use efficiency of Maryland tobacco at reduced fertilization rates. A second set of markers was found to be indicative of nitrogen toxicity in Maryland tobacco at normal Burley levels of fertilization. The list of markers is shown in Table 4 with their relative values between TN90 and Maryland after nitrogen starvation conditions. Table 5 shows metabolic markers that may be indicative of nitrogen toxicity in Maryland tobacco at the normal burley fertilization rate.

TABLE 4

Metabolites Associated with Nitrogen Use
Efficiency at Low Nitrogen Levels

| Biochemical Name | MD609/TN90 |
| --- | --- |
| Spermine | 0.13 |
| Lysine | 0.26 |
| Isoleucine | 0.31 |
| Valine | 0.37 |
| Phenylalanine | 0.38 |
| Tyrosine | 0.38 |
| Spermidine | 0.43 |
| Asparagine | 0.47 |
| Histidine | 0.47 |
| Leucine | 0.48 |
| Arginine | 0.76 |

TABLE 5

Metabolites Associated with Nitrogen
Toxicity at High Nitrogen Levels

| Biochemical Name | MD609/TN90 |
| --- | --- |
| Raffinose | 33.02 |
| Glycerophosphorylcholine (GPC) | 62.74 |
| Nicotianamine | 3.25 |
| Allantoic acid | 12.74 |
| Allantoin | 1.91 |

Figure 5A:
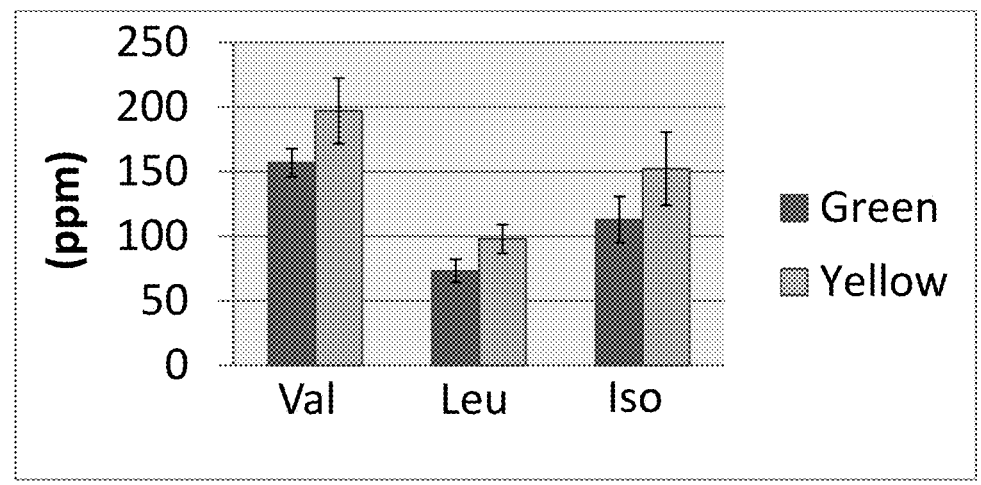
FIG. 5A is a graph showing amino acid content in segregating plants from a cross between TN90 and Maryland 609 grown under low nitrogen conditions (45 lb nitrogen/acre land).
Figure 5B:
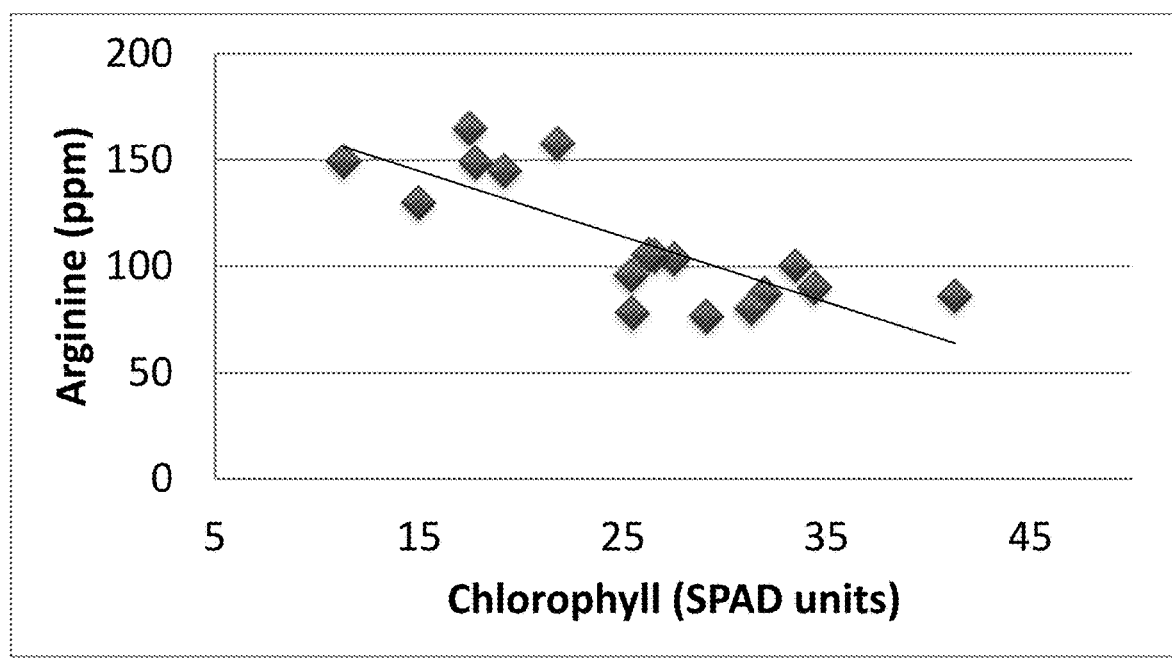
FIG. 5B is a graph showing the arginine content in plants relative to chlorophyll content.

Metabolite markers were also measured in a segregating $F_2$ population resulting from the cross between TN90 and Maryland 609. Plants were grown in the field using 45 lbs/ac of nitrogen. Phenotypic data was collected from the population four weeks after topping (at harvest) including chlorophyll content, yield, stalk diameter, and height. Amino acid content was measured from freeze dried samples and correlated to the relevant phenotypic data. Representative data is shown in FIGS. 5A and 5B.

Example 4

RNAi Line Development, Plasmid Construction and Agrobacterium Transformation

To investigate the function of the candidate genes, transgenic plants were generated expressing either the full length coding sequence of overexpression gene candidates or an RNAi sequence for downregulation of the gene candidate. An expression vector, p45-2-7 (see, for example, SEQ ID NO:57 in US 2015/0173319), was used, which has a CsVMV promoter and a NOS terminator, as well as a cassette having a kanamycin selection marker (NPT II) under direction of the actin2 promoter and a NOS terminator. The nucleic acid constructs carrying the transgenes of interest were introduced into tobacco leaf discs using an Agrobacterium transformation approach. See, for example, Mayo et al., 2006, Nat Protoc., 1(3):1105-11 and Horsch et al., 1985, Science 227:1229-1231.

Briefly, ascetical tobacco plants (Tennessee 90 (TN90)) were grown from magenta boxes, and leaves discs were cut into 15×150 mm plates. Agrobacterium tumefaciens containing the target plasmid were collected by centrifugation of 20 ml cell suspension in 50 ml centrifuge tube at 3500 rpm for 10 minutes. Supernatant was removed and Agrobacterium cell pellet was resuspended in 40 ml liquid resuspension medium. About 25 ml of the solution was transferred to each 15×100 mm Petri plates. In those 15×150 mm plates, tobacco leaves, avoiding the midrib, were cut into 0.6 cm disk. Leaf disks were placed upside down, a thin layer of MS/B5 liquid resuspension medium was added, and slices were made with a #15 razor blade. The leaf discs were poked uniformly with a fine point needle. Eight disks were placed, upside down, in each regeneration plate (15×100 mm). Agrobacterium tumefaciens suspension was added and the leaf discs were incubated for 10 minutes.

Leaf disks were transferred to co-cultivation plates (½ MS medium) and disks were placed upside down in contact with filter paper overlaid on the co-cultivation TOM medium (MS medium with 20 g sucrose/L; 1 mg/L IAA and 2.5 mg/L BAP). The plate was sealed with parafilm and labeled appropriately. Plates were incubated in dim light (60-80 mE/ms) and 18/6 photoperiods at 24° C. for three days. Leaf disks were transferred to regeneration/selection TOM K medium plates (TOM medium with 300 mg/l Kanamycin) and subculture bi-weekly to the same fresh medium in dim light at 24° C. until shoots become excisable. Shoots from leaves were removed with forceps and inserted in MS basal medium with 100 mg/L kanamycin at 24° C. and 18/6 photoperiods with light intensity of 6080 mE/ms for rooting.

When plantlets with both shoots and roots grew large enough (e.g., reach over half of a GA7 box), they were transferred to soil for acclimatization. During the transfer, the gel was washed from the root tissue with tap water. Established seedlings were transferred to the greenhouse for further analysis and to set seed.

Example 5

Random Mutagenesis and Characterization of Mutants

One gram (approximately 10,000 seeds) of Tennessee 90 tobacco (TN90) converter seed was washed in 0.1% Tween® for fifteen minutes and then soaked in 30 ml of ddH$_2$O for two hours. One hundred fifty (150) μl of 0.5% EMS (Sigma, Catalogue No. M-0880) was then mixed into the seed/ddH$_2$O solution and incubated for 8-12 hours (rotating at 30 rpm) under a hood at room temperature (RT; approximately 20° C.). The liquid then was removed from the seeds and the liquid was mixed into 1 M NaOH overnight for decontamination and disposal. The seeds were then washed twice with 100 ml ddH$_2$O for 2-4 hours. The washed seeds were then suspended in 0.1% agar:water solution.

The EMS-treated seeds in the agar solution were evenly spread onto water-soaked Carolina's Choice Tobacco Mix™ (Carolina Soil Company, Kinston, NC) in flats at ~2000 seeds/flat. The flats were then covered with plastic wrap and placed in a growth chamber. Once the seedlings emerged from the soil, the plastic wrap was punctured to allow humidity to decline gradually. The plastic wrap was completely removed after two weeks. Flats were moved to a greenhouse and fertilized with NPK fertilizer. The seedlings were plugged into a float tray and grown until transplanting size. The plants were transplanted into a field. During growth, the plants were self-pollinated to form $M_1$ seeds. At the mature stage, five capsules were harvested from each plant and individual designations were given to the set of seeds from each plant. This formed the $M_1$ population.

A composite of $M_1$ seed from each $M_0$ plant was grown, and leaves from $M_1$ plants were collected and DNA extracted. Target genes were amplified and sequenced for mutation identification.

Example 6

Screening Plants for Modulation of Nitrogen Use Efficiency

There are multiple ways for plants to exhibit increased nitrogen use efficiency. The first is nitrogen uptake, the second is nitrogen assimilation, and the third is nitrogen storage. The integration of these three pathways allows for the most efficient use of nitrogen. The regulation of these three stages can occur in response to light. Under normal field conditions, fertilizer is applied preplant with another amount applied at layby stage. This differs from greenhouse grown plants in that the plants are constantly fed nitrogen through an "Ebb and Flow" system. We have developed a two-step protocol for screening of nitrogen use efficiency. First seedlings are grown under zero nitrogen conditions for 3 weeks and the rate of chlorophyll loss and growth is measured. Selected populations are then grown with a step down fertilization protocol to mimic the depletion of nitrogen in a greenhouse setting.

Figure 2:
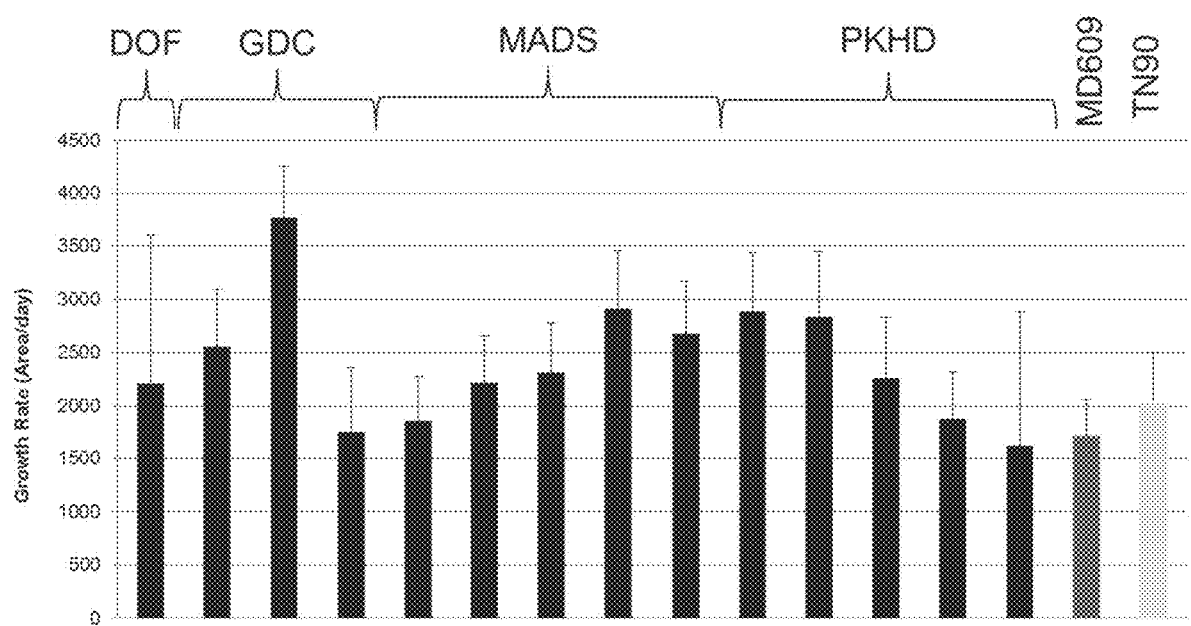
FIG. 2 is a graph showing the growth rate in transgenic plants.

Transgenic and mutant tobacco plants are grown in a greenhouse in 21 cell growth trays. Measurements of chlorophyll loss and plant growth are taken by standard RGB based imaging and image analysis. Representative data is shown in FIGS. 1 and 2. Glutamate decarboxylase RNAi (GDC-RNAi) and MADS-box RNAi expressing lines show reduced chlorophyll loss after nitrogen starvation and increased growth rate relative to burley control lines.

Figure 3:
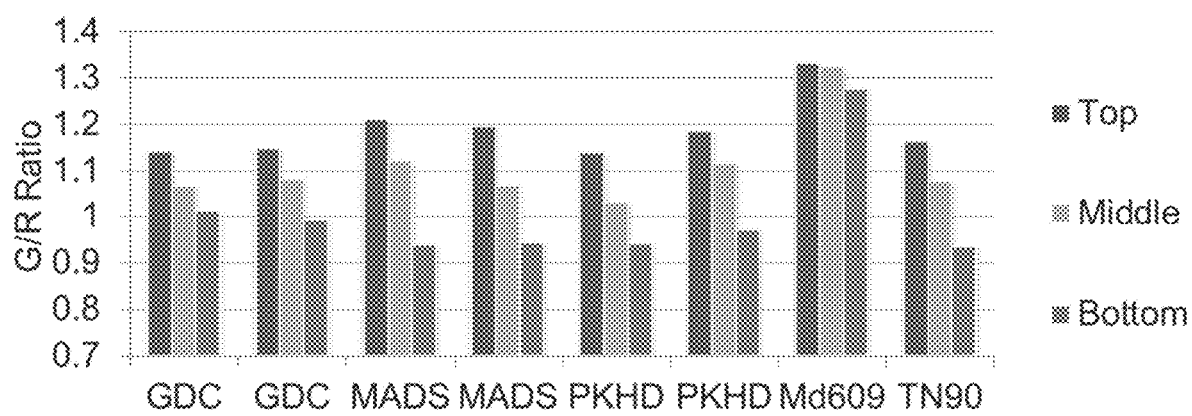
FIG. 3 is a graph showing the chlorophyll content in transgenic top, middle and bottom leaves from plants.
Figure 4:
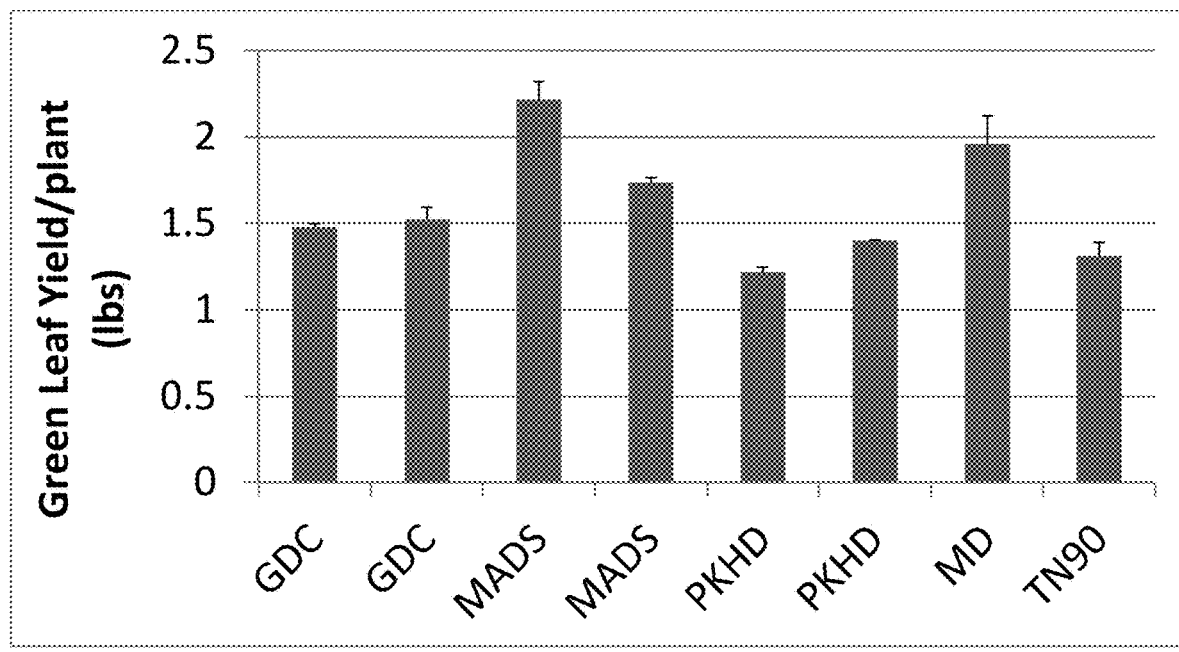
FIG. 4 is a graph showing the green leaf yield in transgenic plants.

Transgenic and mutant tobacco plants are grown in a greenhouse under field-like conditions in Carolina's Choice Tobacco Mix (Carolina Soil Co., Kinston, NC) in 10 inch pots. Fertilization was reduced over time to mimic the reduction of nitrogen over time in the field setting. Measurements of chlorophyll content, and leaf weight were taken. Only one population was used per table to reduce population effects. Representative results from these studies are shown in FIGS. 3 and 4. Reduction in gene expression of the GDC gene resulted in a 12-16% increase in yield relative to the burley control. Reduction in MADS-box gene expression resulted in a 32-69% increase in yield. The Maryland control yielded 49% higher than the burley control. The distribution of chlorophyll throughout the plant was also different. GDC RNAi plants exhibited higher levels of retained chlorophyll in the lower leaves while the upper leaves contained comparable levels of chlorophyll. This suggests a decrease in the amount of redistributed nitrogen from the lower leaves.

Example 7

Introgression of the Maryland Alleles by Breeding

An example of another way to introduce gene expression differences into burley tobacco to increase nitrogen use efficiency is by breeding. The genes of interest described above can be used as markers in a conventional breeding program to select for burley plants containing the genes from Maryland tobacco that confer nitrogen use efficiency.

Figure 6:
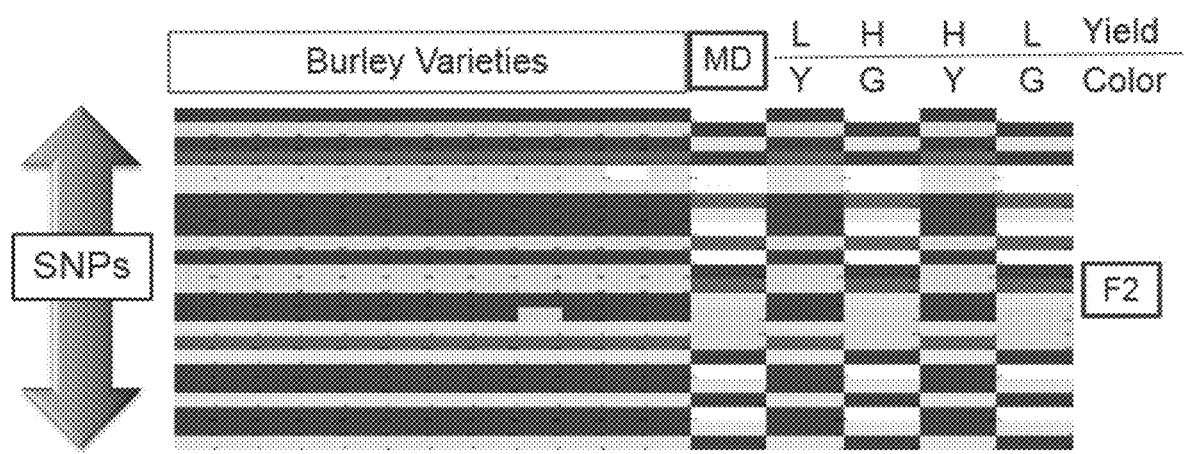
FIG. 6 is a graphical representation showing a representation of SNPs in several Burley tobacco varieties, a Maryland (MD) variety and the segregating F2 population. L, low yield; H, high yield; Y, yellow color; G, green color.
Figure 7:
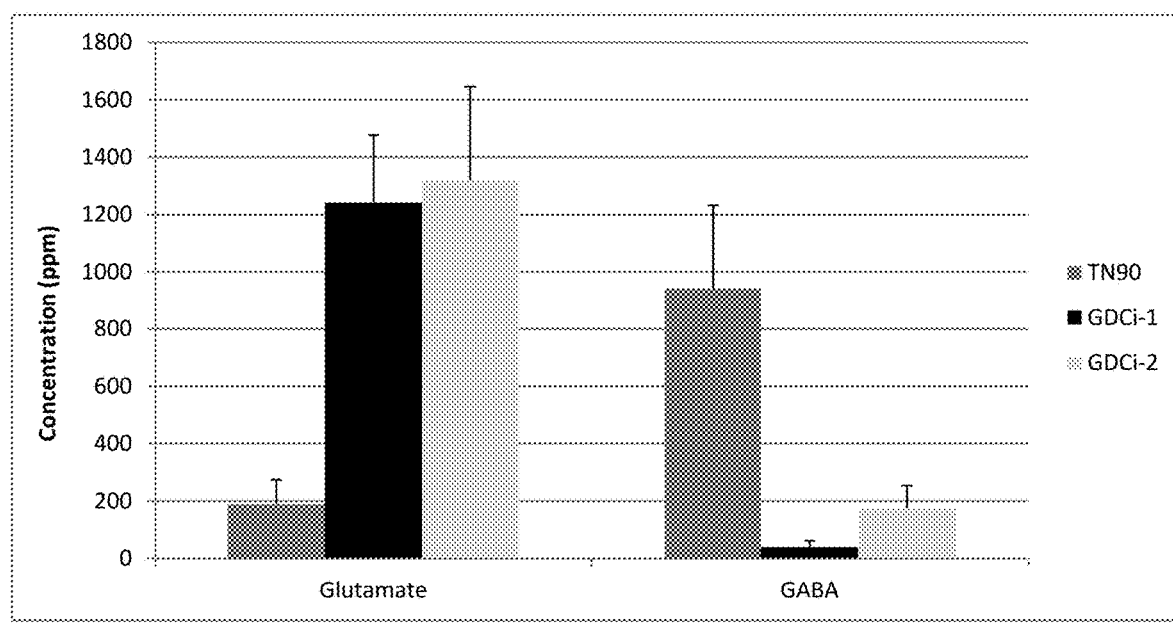
FIG. 7 is a graph showing the levels of glutamate and GABA in the roots of two GDC RNAi lines.

The Axiom Chip, containing 170,000 SNPs, was used to identify SNPs related to nitrogen utilization efficiency (NUE). FIG. 6 shows a graphical representation of the genotypes among Burley varieties and a Maryland variety and a segregating F2 population. The SNPs identified correlate with the Maryland trait of slower chlorophyll loss as the F2 plants that contain the Maryland alleles were still green at harvest. The SNPs identified can be used to track "green" plants (i.e., plants that have an amount and/or rate of chlorophyll loss similar to that of Maryland tobaccos), yield, and other characteristics of nitrogen utilization efficiency in tobacco.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A tobacco plant comprising an induced mutation in a glutamate decarboxylase gene, wherein the glutamate decarboxylase gene comprises an allele comprising a nucleic acid sequence of SEQ ID NO: 9 or 10, wherein the induced mutation comprises an introduced stop codon that results in a truncated polypeptide encoded by the glutamate decarboxylase gene, and wherein the induced mutation causes a loss-of-function of the polypeptide encoded by the glutamate decarboxylase gene.

2. The tobacco plant of claim 1, wherein the induced mutation is selected from the group consisting of a point mutation, an insertion, a deletion, and a substitution.

3. The tobacco plant of claim 1, wherein the tobacco plant exhibits an increase in yield relative to a tobacco plant lacking the induced mutation.

4. The tobacco plant of claim 1, wherein the tobacco plant exhibits decreased or slowed chlorophyll loss relative to a tobacco plant lacking the induced mutation.

5. The tobacco plant of claim 1, wherein the tobacco plant is of a type selected from the group consisting of a Burley type, a dark type, a flue-cured type, a Maryland type, and an Oriental type.

6. A tobacco seed from the tobacco plant of claim 1, wherein the tobacco seed comprises the induced mutation a glutamate decarboxylase gene.

7. Cured tobacco leaf from the tobacco plant of claim 1.

8. The cured tobacco leaf of claim 7, wherein the cured tobacco leaf is air cured, fire cured, or sun cured.

9. A method for producing a tobacco plant, the method comprising:
   (a) inducing mutagenesis in tobacco cells to produce mutagenized cells;
   (b) obtaining one or more tobacco plants from the mutagenized cells; and
   (c) identifying at least one tobacco plant obtained in step (b) that comprises an induced mutation in one or more endogenous nucleic acids comprising a nucleic acid sequence of SEQ ID NO: 9 or 10, wherein the induced mutation comprises an introduced stop codon that results in a truncated polypeptide encoded by the glutamate decarboxylase gene, and wherein the induced mutation causes a loss-of-function of the polypeptide encoded by the glutamate decarboxylase gene.

10. The method of claim 9, wherein the at least one tobacco plant identified in step (c) exhibits an increase in yield relative to a plant lacking the induced mutation.

11. The method of claim 9, wherein the at least one tobacco plant identified in step (c) exhibits a decrease in the amount and/or rate of chlorophyll loss relative to a plant lacking the induced mutation.

12. The method of claim 9, wherein the mutagenesis comprises the use of an agent selected from the group consisting of a chemical mutagen, ionizing radiation, a TALEN, a CRISPR/Cas9, and a zinc-finger nuclease.

13. The method of claim 9, wherein the induced mutation is selected from the group consisting of a point mutation, an insertion, a deletion, and a substitution.

14. A method for producing a tobacco plant, the method comprising:
   (a) crossing a plant of a first tobacco line with a plant of a second tobacco line, wherein the plant of the first tobacco line comprises an induced mutation in one or more endogenous nucleic acids comprising a nucleic acid sequence of SEQ ID NO: 9 or 10, wherein the mutation comprises an introduced stop codon that results in a truncated polypeptide encoded by the glutamate decarboxylase gene, and wherein the induced mutation causes a loss-of-function of the polypeptide encoded by the glutamate decarboxylase gene; and
   (b) selecting at least one progeny tobacco plant, wherein the at least one progeny tobacco plant comprises the mutation.

15. The method of claim 14, wherein the at least one progeny tobacco plant exhibits an increase in yield relative to a plant lacking the induced mutation.

16. The method of claim 14, wherein the at least one progeny tobacco plant exhibits a decrease in the amount and/or rate of chlorophyll loss relative to a plant lacking the induced mutation.

* * * * *

SEQUENCE LISTING

```
<160> NUMBER OF SEQ ID NOS: 20

<210> SEQ ID NO 1
<211> LENGTH: 738
<212> TYPE: DNA
<213> ORGANISM: Nicotiana tabacum

<400> SEQUENCE: 1
atgccttcag acgtaagtga acgaaaagct accaaacaac agcaaggagc tgcaccggca      60
ccggagccgg agcatcttcc atgtccacgc tgtgattcca ccaacactaa attctgctac     120
tacaacaact acaacttctc tcagccacgt cacttctgta agtcctgccg ccgttattgg     180
```

```
acacacggcg gcactcttcg tgacatcccc gttggtgggg gtagtcgcaa aaatgccaaa    240
cgctcccgta caatcactac taacaacacc agtagcagca ctagcagctg cttgtcctcc    300
acgctctctc ctcgcgacta ccatcacgcg cctactccat cacacgtttc tccattttg    360
gttcctctaa ctgccgatca tcacggcggg ccactaccct tgacgtgaa gccgaatggg     420
aacatgtgtg ggagtttcac ctcgttgttg agcaatactc aagggcctca tggtctttta   480
gcactcagtg ggttcgggct tggagttggg cctgcaattg aagatatggg ctttggtctt   540
ggaaggccca tatggccatt tcctggagta gtgtcgcata ccagtgttga tcatagtaac   600
agtaacggtg ctggagctag tatgttgggc aacacgtggc agcttgctag tggagaaggt   660
ggatttgttg gagctggagg agattgtttt aatttcccag aacttgctat ttcaacgcat   720
ggaaatggta tgaaatga                                                  738
```

<210> SEQ ID NO 2
<211> LENGTH: 738
<212> TYPE: DNA
<213> ORGANISM: Nicotiana tabacum

<400> SEQUENCE: 2

```
atgccttcag acgtaagtga acgaaaagct accaaacaac agcaaggagc tgcaccggca    60
ccggagccgg agcatcttcc atgtccacgc tgtgattcca ccaacactaa attctgctac   120
tacaacaact acaacttctc tcagccacgt cacttctgta agtcctgccg ccgttattgg   180
acacacggcg gcactcttcg tgacatcccc gttggtgggg gtagtcgcaa aaatgccaaa   240
cgctcccgta caatcactac taacaacacc agtagcagca ctagcagctg cttgtcctcc   300
acgctctctc ctcgcgacta ccatcacgcg cctactccat cacacgtttc tccattttg   360
gttcctctaa ctgccgatca tcacggcggg ccactaccct tgacgtgaa gccgaatggg    420
aacatgtgtg ggagtttcac ctcgttgttg agcaatactc aagggcctca tggtctttta  480
gcactcagtg ggttcgggct tggagttggg cctgcaattg aagatatggg ctttggtctt  540
ggaaggccca tatggccatt tcctggagta gtgtcgcata ccagtgttga tcatagtaac  600
agtaacggtg ctggagctag tatgttgggc aacacgtggc agcttgctag tggagaaggt  660
ggatttgttg gagctggagg agattgtttt aatttcccag aacttgctat ttcaacgcat  720
ggaaatggta tgaaatga                                                 738
```

<210> SEQ ID NO 3
<211> LENGTH: 245
<212> TYPE: PRT
<213> ORGANISM: Nicotiana tabacum

<400> SEQUENCE: 3

```
Met Pro Ser Asp Val Ser Glu Arg Lys Ala Thr Lys Gln Gln Gln Gly
1               5                   10                  15

Ala Ala Pro Ala Pro Glu Pro Glu His Leu Pro Cys Pro Arg Cys Asp
            20                  25                  30

Ser Thr Asn Thr Lys Phe Cys Tyr Tyr Asn Asn Tyr Asn Phe Ser Gln
        35                  40                  45

Pro Arg His Phe Cys Lys Ser Cys Arg Arg Tyr Trp Thr His Gly Gly
    50                  55                  60

Thr Leu Arg Asp Ile Pro Val Gly Gly Gly Ser Arg Lys Asn Ala Lys
65                  70                  75                  80

Arg Ser Arg Thr Ile Thr Thr Asn Asn Thr Ser Ser Ser Thr Ser Ser
```

```
            85                  90                  95
Cys Leu Ser Ser Thr Leu Ser Pro Arg Asp Tyr His His Ala Pro Thr
            100                 105                 110
Pro Ser His Val Ser Pro Phe Leu Val Pro Leu Thr Ala Asp His His
        115                 120                 125
Gly Gly Pro Leu Pro Phe Asp Val Lys Pro Asn Gly Asn Met Cys Gly
    130                 135                 140
Ser Phe Thr Ser Leu Leu Ser Asn Thr Gln Gly Pro His Gly Leu Leu
145                 150                 155                 160
Ala Leu Ser Gly Phe Gly Leu Gly Val Gly Pro Ala Ile Glu Asp Met
                165                 170                 175
Gly Phe Gly Leu Gly Arg Pro Ile Trp Pro Phe Pro Gly Val Val Ser
            180                 185                 190
His Thr Ser Val Asp His Ser Asn Ser Asn Gly Ala Gly Ala Ser Met
        195                 200                 205
Leu Gly Asn Thr Trp Gln Leu Ala Ser Gly Glu Gly Gly Phe Val Gly
    210                 215                 220
Ala Gly Gly Asp Cys Phe Asn Phe Pro Glu Leu Ala Ile Ser Thr His
225                 230                 235                 240
Gly Asn Gly Met Lys
            245

<210> SEQ ID NO 4
<211> LENGTH: 804
<212> TYPE: DNA
<213> ORGANISM: Artificial Sequence
<220> FEATURE:
<223> OTHER INFORMATION: synthetically-generated oligonucleotide

<400> SEQUENCE: 4
acggatccac aagcgagaag aaaaatgcct tcagacgtaa gtgaacgaaa agctaccaaa      60
caacagcaag gagctgcacc ggcaccggag ccggagcatc ttccatgtcc acgtgtgat     120 tccaccaaca ctaaattctg ctactacaac aactacaact tctctcagcc acgtcacttc     180
tgtaagtcct gccgccgtta ttggacacac ggcggcactc ttcgtgacat ccccgttggt     240
gggggtagtc gcaaaaatgc caaacgctcc cgtacaatca ctactaacaa caccagtagc     300
agcactagca ctgcttgtcc tccacgctct ctcctcgcga ctaccatcac gcgcctactc     360
catcacacgt ttctccattt ttggttcctc taactgccga tcatcacggc gggccactac     420
cctttgacgt gaagccgaat gggaacatgt gtgggagttt cacctcgttg ttgagcaata     480
ctcaagggcc tcatggtctt ttagcactca gtgggttcgg gcttggagtt gggcctgcaa     540
ttgaagatat gggctttggt cttggaaggc ccatatggcc atttcctgga gtagtgtcgc     600
ataccagtgt tgatcatagt acagtaacgg tgctggagct agtatgttgg caacacgtg     660 gcagcttgct agtggagaag gtggatttgt tggagctgga ggagattgtt ttaatttccc     720
agaacttgct atttcaacgc atggaaatgg tatgaaatga ttgtttaagg atggtatgaa     780
atgattgttt aaggattcta gagt                                            804

<210> SEQ ID NO 5
<211> LENGTH: 903
<212> TYPE: DNA
<213> ORGANISM: Nicotiana tabacum

<400> SEQUENCE: 5
atgttttctg ggttctccca tttcagttgt gatgcaatca acgcctgttg ggccgctcct      60
```

```
gtcctaatat cgttaaatat tgcactgaag tgtgtaaaaa agcaatcttt atctactgaa    120
gctattgaag agcggttagc tggagtacct gtttatgcac ttagcaatgc ttctgaagaa    180
ttcgtgcttg tttcgggtgt tagtactggt aaaaatcttg ggttattttg ctttagtgaa    240
gctgatgctg aagctcttcg tcagcaaatg gaatctatgg accctactat gcgaaatggc    300
tcgagggttg ttcctgttgc tcttaataag gttttccagc tcaaagttga tggagtggct    360
tttaggctga taccagaggc atctcaagta agaatgcaa tgaaggaaag ggaaaggact    420
ggaacgtctg atgagagctt ttatggtgtt ccagtgtttc agtcaaggag cttaattctg    480
aggagccaga acaagagata tcgccctgtt ttcttcagga aggaggacct agagaattca    540
ctagtaagag cttctcaaca gcaaggccga ttgaatcctg ctttgaaagg agatattcag    600
gttgctgttc tggaggatat aatacaaggc atgaaggata cttcgacgtc aaagtgggac    660
gatgttgtat ttgttcctcc gggtttcgat gtttcaacag atccttccca gaataacttt    720
gactatgcat taggtcctgt tatgcgacaa attcttatag aaaccggagc taagatttct    780
gaagtgtttg ataattgtag acaaattctg tgtgcaatta acttctctca ctcgaagtgt    840
gacgttaatc tcgatagcag tggtgatgtg tatgttattg ataagcttta cattttgagc    900
tga                                                                 903

<210> SEQ ID NO 6
<211> LENGTH: 8144
<212> TYPE: DNA
<213> ORGANISM: Nicotiana tabacum

<400> SEQUENCE: 6
atgttttctg ggttctccca tttcagttgt gatgcaatca acgttaaatt catttaattt     60
tttgtacttt ataaaactaa gttctcattt tttttaattt cacatcctca cttgtctaat    120
ttttaaaaaa ataatattca ttaaatataa tatatatata tatatattaa ggcctcttat    180
taagtgtttg tttaggcct gttgggccgc tcctgtccta atatcgttaa atattgcact    240
gaagtggtaa gttactcatg catctttaat taaatatttt gaattagaat taaaagaata    300
aaattacctt tgataataag cactttaccc caatagattt tttaagccgt atgggtaaat    360
aaaacactct taatataggt aaacaatttc cttttacct tgcctctctc tctatctttt    420
gttcccaccc acccccacac cctcaccccc tacccccac cctctcccct tttcttctag    480
acgcaaaatc tttagcagtt tttaaaacct ccaaaaccct tttcaccatt ttctctctaa    540
tttcaactaa aacagaggag aaaaaaaaac atgaatatct caaacctaa acagtcatct    600 tcttcttcag caacaccacg tcaccaccac atctacagct ccaacaaact ttcaagaatt    660
tacaaaccca tttctccaat ttccttcaaa ccacttttcc gcaactcaac acactcaatt    720
cttctcaaaa ttcacaaaac ccatgggcta aaattggtgt taataataat aatagtgtaa    780
aaaagcaatc tttatctact gaagctattg aagagcggtt agctggagta cctgtttatg    840
cacttagcaa tgcttctgaa gaattcgtgc ttgtttcggg tgttagtact ggtaaaaatc    900
ttgggttatt ttgctttagt gaagctgatg ctgaagctct tcgtcagcaa atggaatcta    960
tggaccctac tatgcgaaat ggctcgaggg ttgttcctgt tgctcttaat aaggttagct   1020
tcattaattg cttttctaca accccatttt ttgtgtaatg gatgtgctta ttgtgttatg   1080
attaacagta gtgaagccag aaaattcaat aagagtgttc aaattttgaa caacctttgt   1140
cagtgggcta tgcaaggtgt tcaaagtctt ttttattaat aacaagtaat atttgaccct   1200
```

```
atatacagaa taattttaaa gggtgttcag ttgaccactc ttggccacac atagcttcat    1260
ccgtgatgat taactatgct cgacaagtag tgttatgtcg ggtcaatgaa gtgggatgag    1320
aaccatagcg gaggcaaaag aacactaggt aattttttcct tagtggatag agttatcttg   1380
tacctttgct ggtgggagct agtagataca tgtagaatag gtgcgcgcaa gttggcacag    1440
acaccactgt cattagaaaa acttaagaaa attaaaaaat agtgttcggg gggttagtac    1500
acgactacac ggacttgttg tgtgtcgaat ataataaatg aattgtttat gtgaggaata    1560
ataatgcgag gattgttata gggtgaaaaa gaatatagag attgttatgg gttgagtact    1620
attgcaggga ttttatgca tagattgcct acttaatatt tgttcccgtt gctctcgata     1680
aggttaaatt tattggctgc gattggcccc gacatcacag tcatctgaaa aagaaaagta    1740
ataacaaata gtgtcaaata gtgttagcgg ggttagcaca tggactaatt ttgctgcgat    1800
tataatgaag gatttgttta tgtggagaac aaagacaaaa atgtagggat tgttatgcat    1860
tgagtactag tgtggggatt attatgcgta gattgcctac gtataggaat ttttgtcttt    1920 agatatttt atctatgtat tctaatacac gtttcctatt ctacattcta ttttgcacga    1980
aataatatat agattcctgc aaagcttaca agggtactgg caatgtggag tttaaactgc    2040
caatcaaatg ctacattaat atacaaagat tgttttttcct taggcagcta aacaaacatt    2100
gaatttactt tgtggaattt catgttgaga ttatatttt atgcggcaat aacgtgagcc     2160
cttataaaac gtgtgtttga cttaacatga ttattaagag aaacaagaat tatgtcttaa    2220
tcctaagttg tgattgacta tataaatccc caataatcat ttcgttccat ttggcccgtc    2280
ccatttcaat tcaatgattt gggtttctct aaaccggagg ttctttacat tctttaagtg    2340
aaatataaat ttttaaacaa actaaaaga cttgtaacaa acactaaact ggtctgtagt     2400
gtactgacat gattatctct taatcgaaaa tatgggtgtt ttgggaatca aagagcttaa    2460
aatttagagt aagaactgag aataagaatt gtttaacatt tgctgagaaa tagccatgtg    2520 tttactttt ataactagaa caatgacgta aagataatat ggtattggaa agaacaaaag     2580
caagtaggac aagcatgtct aagctagtaa ttgtcgttgt tgaatttaaa tactgattat    2640
cagaggctga tagttgtatt ctttattgcg aaagaaaaat gttattaagt ctaattgatg    2700
gtcaataatg caggttttcc agctcaaagt tgatggagtg gcttttaggc tgataccaga    2760
ggcatctcaa gtaaagaatg caatgaaggt gaatatctga tgataaagat ttctgtaatt   2820
tttattcatg aagtcaatgt tttgattttg gtttgaaatt ctctggctgc agactaagtg    2880
tgtgcttaaa tctttaagaa agctgataaa gtactcatgt actcatgtca tcatgttagt    2940
atcgtgagaa tttgaaattc ggttgcttgt cgatcttcaa gaagtgctgt ctataggtca    3000
atcagtttct tatgttctta atcaaaaaag ggcagcccgg tgcactaagc tcccgctatg    3060
cacccgaaaa aggccggacc acaagggttt attatacgca acctttatct tcatttctgt    3120
aagaggctgt ttccacggct cgaacccgtg acctcctggt cacatgacaa caactttact    3180
agttacacca aggctcccct tcgttcttaa tcaaacaaaa gattattcat tttggaggtc    3240
tccattagtc tattatagta gagtatcata gctttccagg atcaggtatt acctattctc    3300
tgcttgctga gcatagtcat gatcattgca aagtatttgc aggtattcca aagttttcga    3360
caatctaagt tctgaaatgt acttcatggc cattggtcaa gattttgaaa gttttagtat    3420
cattatctat gaaacttta cacaattgt atgttttaat tagcatatta cacactcttt     3480
tattgttcta gctctcccctt ttatgcaacc aatgtgcgag cattggttgc atacactgtc   3540
aagcataaga ttcttccagt ttcagtactt cgtactgtcg atgattttaa catcctgtcc    3600
```

```
tttgcggagt ggttttcttg ttcttactag tagcattagt acgccttgtc gtattgtttt    3660
cagtcttagg tttctattat tgtctgttgt tgctttcatt ttggtcatct tactatcttc    3720
tgttatcaat gcttcttttc catggctcct cactattgtt tctggctgtt ttcatttcat    3780
tactgttgag cttattcttc actgagccga gggtctatgg gaaacaaaat ctctatctcc    3840
acgcttcttt tccatggctc ctcactattg ttttctagctg ttttcatttc attactgttg    3900
agcttattct tcactgagcc gagggtctat gggaaacaaa atctctatct ccacgagata    3960
gggtaaggtc tgcgtacaca ctgccctccc cagaccccac tatgtgggat tacactatgt    4020
tttttgttgt tgttgctgct gctgtgtgag cacttttggt tattccaaga ttccttctct    4080
ataaatatgt tatgattgat gattcaacag gaatcctatc taaaacattg taagaccccg    4140
tcttttgttt gactaaatgc taaaaacatc cagagtaatg agatagcaca acaataagta    4200
gtagatactt ttgcttgacg ccaaatctga aaatttgtgg cacttcagat tagcattaag    4260 atgttttttct tcatcttaga gataaatata tagtaaacag aagttgcttt tgagttgaag    4320
tggatgaaaa gatagctgtt gctcagtaag tttcttttta catgtaccag ttgtggactc    4380
cagaacatag tgtcataaca tatattcggt cagtcaaatg ttaggaggcc tcatctttaa    4440
gtgatatttc tttgaggata acatttaggt ttctgcttat gccaaaaata ttttttgtgta    4500 tccaaattta gttcagcatg tttaaattat cattttgggc gccataactt ttttcctgcta    4560 taatctgaag ctgatcatat tctgctgcca ttttttttaa ctaggaaagg gaaaggactg    4620
gaacgtctga tgagagcttt tatggtgttc cagtgtttca ggtacactct ctcagctata    4680
atcttggcat cctttagcag ctagacaact gccaaagcat gatataaaaa gtcggtttag    4740
aaactgaaat gctcatctgc cttgtcattt gtgcttactg ctacgtcccc gtgtgtgagt    4800
ggaaacaaat gcttttttttt accttatcaa aaaaaatctt tgaatgacat atgagctcaa    4860
ctaggatcca gtaccttcaa gaccggaaaa gatccaatct gccttaaaact gcaattaaga    4920 gaatccctgt gtgcactaat aaatgcccga aatgattaaa ggcaaaaaga catccgcgca    4980
aaatattgcg aagcttcgac ctctgcatct gagacagcat tgcattgctc tcgtttcacc    5040
ttcttggatg atgttgcctg gttaagaaag ttcttttttgc gcttgtgtag cagcctgatg    5100
caaatttaac tttagaatca tcattaataa tgtgaccact actgaggttt taagctagat    5160
atcctcttca ttcatataag aaagagttct aatggcaaac ctatttagta tttccttata    5220
ggactcgcat gtttgtgcca atatgttttct tattttattc ctaaagatac caatctctta    5280
ttatgaaata agccgatctc ttggatgaat aagtgcgtaa catttccatg attgaatatg    5340
ttgaaggatg caaaaccatc tccacaaacc gacatatggg agagttccga tgtttcacag    5400
tttgcttaaa ttttattatt caaaagaat atcgtggcag acaggattcg gatcctagca    5460
aaagcaaaaa agttaggtga tttctttcca tttatctaaa ttttggtagg cagagttatc    5520
caattcctat acttgtgaga gaatgcaggt atccagtaga atatttgagg taattttctt    5580
ataaccgtgg gtttaggcca acttgtgcgc accttgacta attccacggg gtacctgcta    5640
tctccggggg ccaccagcac aggtacgggg taactctgtc taccaaggct cgggataaac    5700
accatgcggc agacatctga aaatcacagt caaataattt cacaacagat ttcgtaccgt    5760
taagattcat agattgtgtg aatggtgggc tgggaatttc atgccacatg acagccttct    5820
ttgctatata gccacaaaata tagcatacta gatcttgttt ttcttgtcag ttctccttct    5880
catgagtttg aaaattatag tcaaggagct taattctgag gagccagaac aagagatatc    5940
```

```
gccctgtttt cttcaggaag gttagctaac tgtctggagt tagtatccac taatgtgata    6000
tgatgctata tcgcccttcg tgtaaattta tcaacttgtg caggaggacc tagagaattc    6060
actagtaaga gcttctcaac agcaaggccg attgaatcct gctttgaaag gagatattca    6120
ggtacgtcta ttgatattta cttaccgttg tgtcttagct tcaagaatta tgaccgagaa    6180
ttttcatctg atttcacagg ttgctgttct ggaggatata atacaaggca tgaaggtgag    6240
aatcctcaac aagaaattta catgttatat cgtcgagttc ttgatccaac aaatgatgtc    6300
gggaaattat gcagaacttc tctgtcgtcc tcttactcgt tttagtttct tatatatata    6360
tatttttgct aatcaagaaa ttgccaaagc cagatagcac atggttcgaa actcagtgga    6420
taatagccgc ccctctaccc ttttccattt aaataccaag cttttgtatg caacattgtt    6480
tgaactcgtg acatgtgcct aactcacaca tcatgcgtta cgctgttatt tatgttcatc    6540
ttgcttgtta aatgcacatt gccttggtta atggccgtaa tggagtcggt gcgattaaca    6600
aagaatgaac atattttgc aggatacttc gacgtcaaag tgggacgatg ttgtatttgt    6660
tcctccgggt ttcgatgttt caacagatcc ttcccagaag taagagaacc tatgtcaagt    6720
catctcatgg tgcttggcca atcctatatt agcatttttg atatcatgtg tgtaaattgt    6780
agtaactttg actatgcatt aggtcctgtt atgcgacaaa ttcttataga aaccggagct    6840
aagatttctg aagtgtttga taattgtaga caaattctgt gtgcaattaa cttctctgta    6900
ggatgtcaaa cggtgtggtg cggttgcagg gcaaacccgc aaagatttcg ccccgcaccg    6960
catcacataa tttgttgttt tcaacccacc ctacctgccc cgcataaacc cgccccccgt    7020
ttaagttttt ttttttcttt ttttttcttt ttgatagtaa aaactaagat tcataaactt    7080
cttttttcatt ttttctgaaa tagtattaat ttaatgtaaa cccaaatcct atacaagcac    7140
ctccctaaca aaaccaaagt gacagtgtct tgccgttgtt accatatcaa gtcttggttt    7200
atctttctttt cactaattat ttgcaattta ggaatacttt tctaaattaa tgagtttcct    7260
gtttaagttt tttttttttt ttttttttg attacaattg ctataagctt ggttgtttta    7320
acatttcttt atttctgttt tgcaatgagt cttttgaaag ttgaaactcc aatccccaaa    7380
tcatcaagaa aggaaaagta caaatagctc tgagtccatt ttcttattta taaaggtgag    7440
aaaccatgta atctaataag taaaataata tatagtacaa cactagtaga ctcttagaag    7500
cagcggcaat gcaaaagttt ggatcagtat gtgtttcttg gcaaaaccag cagccatacc    7560
cgcgtcaacc cgcacctgcc ctgcaaccgc aagtttttt taaaaaacaa aattccaccc    7620
gccccgctta ggttcaaacc cgccccgccc cgtaccgctc tattgccatc cctacttctc    7680
tgagttggct tgggccaatg taaggaaacc atagctagtc caactatgct ctacgtagaa    7740
atgactctag gtagtcattt taagggatg ttatttaaaa attaaccagt gcgtcctgaa    7800
ttttagtttt tcagttcatt ttttcgggac aaaaatatcc tgaattgtcc tatagttaag    7860
gtatttaatt taaaatttca agtcaaaata agtattgact aatctctaaa tagcatccct    7920
gagaatgact atctgtacaa ttgtccctga gaatgacttg gtgtaacacg gatactgtgg    7980
ataaaatctc gagtacagat cgaaatttgt tgaataatgg gttactttat aatatttcg    8040
cttaaatatt aaacttttgt ctatgatagc actcgaagtg tgacgttaat ctcgatagca    8100
gtggtgatgt gtatgttatt gataagcttt acattttgag ctga                   8144
```

<210> SEQ ID NO 7
<211> LENGTH: 300
<212> TYPE: PRT
<213> ORGANISM: Nicotiana tabacum

<400> SEQUENCE: 7

```
Met Phe Ser Gly Phe Ser His Phe Ser Cys Asp Ala Ile Asn Ala Cys
1               5                   10                  15
Trp Ala Ala Pro Val Leu Ile Ser Leu Asn Ile Ala Leu Lys Cys Val
            20                  25                  30
Lys Lys Gln Ser Leu Ser Thr Glu Ala Ile Glu Arg Leu Ala Gly
        35                  40                  45
Val Pro Val Tyr Ala Leu Ser Asn Ala Ser Glu Glu Phe Val Leu Val
    50                  55                  60
Ser Gly Val Ser Thr Gly Lys Asn Leu Gly Leu Phe Cys Phe Ser Glu
65                  70                  75                  80
Ala Asp Ala Glu Ala Leu Arg Gln Gln Met Glu Ser Met Asp Pro Thr
                85                  90                  95
Met Arg Asn Gly Ser Arg Val Val Pro Val Ala Leu Asn Lys Val Phe
            100                 105                 110
Gln Leu Lys Val Asp Gly Val Ala Phe Arg Leu Ile Pro Glu Ala Ser
        115                 120                 125
Gln Val Lys Asn Ala Met Lys Glu Arg Glu Arg Thr Gly Thr Ser Asp
    130                 135                 140
Glu Ser Phe Tyr Gly Val Pro Val Phe Gln Ser Arg Ser Leu Ile Leu
145                 150                 155                 160
Arg Ser Gln Asn Lys Arg Tyr Arg Pro Val Phe Phe Arg Lys Glu Asp
                165                 170                 175
Leu Glu Asn Ser Leu Val Arg Ala Ser Gln Gln Gln Gly Arg Leu Asn
            180                 185                 190
Pro Ala Leu Lys Gly Asp Ile Gln Val Ala Val Leu Glu Asp Ile Ile
        195                 200                 205
Gln Gly Met Lys Asp Thr Ser Thr Ser Lys Trp Asp Asp Val Val Phe
    210                 215                 220
Val Pro Pro Gly Phe Asp Val Ser Thr Asp Pro Ser Gln Asn Asn Phe
225                 230                 235                 240
Asp Tyr Ala Leu Gly Pro Val Met Arg Gln Ile Leu Ile Glu Thr Gly
                245                 250                 255
Ala Lys Ile Ser Glu Val Phe Asp Asn Cys Arg Gln Ile Leu Cys Ala
            260                 265                 270
Ile Asn Phe Ser His Ser Lys Cys Asp Val Asn Leu Asp Ser Ser Gly
        275                 280                 285
Asp Val Tyr Val Ile Asp Lys Leu Tyr Ile Leu Ser
    290                 295                 300
```

<210> SEQ ID NO 8
<211> LENGTH: 881
<212> TYPE: DNA
<213> ORGANISM: Artificial Sequence
<220> FEATURE:
<223> OTHER INFORMATION: synthetically-generated oligonucleotide

<400> SEQUENCE: 8

```
agggatccaa aaaaaacatg aatatcttca aacctaaaca gtcatcttct tcttcagcaa      60
caccaccaca tctacagctc caacaaactt tcaagaattt acaaacccat ttctccaatt     120
tccttcaaac cacttttccg caactcaaca cactcaattc ttctcaaaat tcacaaaacc     180
catgggctaa aattggtgtt aataataata atagtgtaaa aaagcaatct ttatctactg     240
aagctattga agagcggtta gctggagtac ctgtttatgc acttagcaat gcttctgaag     300
```

```
aattcgtgct tgtttcgggt gttagtactg gtaaaaatct tgggttattt tgctttagtg    360
aagctgatgc tgaagctctt cgtcagcaaa tggaatctat ggaccctact atgcgaaatg    420
gctcgagggt tgttcctgtt gctcttaata aggttttcca gctcaaagtt gatggagtgg    480
cttttaggct gataccagag gcatctcaag taaagaatgc aatgaaggaa agggaaagga    540
ctggaacgtc tgatgagagc ttttatggtg ttccagtgtt tcagtcaagg agcttaattc    600
tgaggagcca gaacaagaga tatcgccctg ttttcttcag gaaggaggac ctagagaatt    660
cactagtaag agcttctcaa cagcaaggcc gattgaatcc tgctttgaaa ggagatattc    720
aggttgctgt tctggaggat ataatacaag gcatgaagga tacttcgacg tcaaagtggg    780
acgatgttgt atttgttcct ccgggtttcg atgtttcaac agatccttcc cagaagtaag    840
agaacctatg tcaagtcatc tcatggtgct tggtctagac t    881

<210> SEQ ID NO 9
<211> LENGTH: 1491
<212> TYPE: DNA
<213> ORGANISM: Nicotiana tabacum

<400> SEQUENCE: 9
atggttctgt ccaagacagc gtcggaaagt gacgtctcca tccactccac tttcgcttcc     60
cgatatgttc gaacttctct tcccaggttt aagatgccag agaattctat accaaaagaa    120
gcagcatatc aaatcataaa tgatgagctt atgttagatg gaaatccaag gctaaattta    180
gcatcttttg tgacaacatg gatggaacca gagtgtaata agttaatgat ggattccatt    240
aacaagaact acgttgacat ggatgaatac cctgtaacca ctgagcttca gaatcgatgt    300
gtaaatatga tagctcattt gtttaacgca ccacttggag atggagagac tgcagttgga    360
gttggaactg tttgatcctc tgaggctatt atgcttgctg gattagcctt caagagaaaa    420
tggcaaaata aaatgaaagc ccaagggaag ccctgtgaca gcccaatat tgtcactggt    480 gccaatgtcc aggtgtgttg ggagaaattt gcaaggtatt ttgaagtgga gttgaaagaa    540
gtaaaattga gtgatggata ctatgtgatg gaccctgaga agctgtgga atggtggat    600 gagaatacaa tttgtgtagc tgctatcttg ggttccactc tcaatggtga atttgaagat    660
gttaagcgct tgaatgacct cttgattgag aagaacaaag aaaccgggtg ggacactcca    720
attcatgtgg atgcagcaag tggtggattc attgcaccat tcctttatcc tgagcttgaa    780
tgggatttta gattaccatt ggtgaagagt attaatgtga gtggtcacaa atatggtctt    840
gtctatgctg gtattggttg ggccatttgg aggaataagg aagacttgcc tgatgaactt    900
attttccaca ttaattatct tggtgctgat caacctactt tcactctcaa cttctctaaa    960
ggttctagcc aagtaattgc tcaatattac caacttattc gcttgggttt tgagggttac   1020
aagaatgtta tggagaattg tcaagaaaat gcaagggtac taagagaagg acttgaaaaa   1080
agtggaagat tcaatataat ctccaaagaa attggagttc cattagtagc tttctctctt   1140
aaagacaaca gtcaacacaa tgagttcgaa atttctgaaa ctcttagaag atttggatgg   1200
attattcctg catatactat gccaccaaat gctcaacatg tcacagttct cagagttgtt   1260
attagagaag atttctcccg tacactcgcg gagcgactgg tgatagacat tgaaaaagtc   1320
ctccacgagc tagacacact tccggcgagg gtcaacgcta agctcgccgt ggccgaggcg   1380
aatggcagcg gcgtgcataa gaaaacagat agagaagtgc agctgagat tactgctgca   1440 tggaagaaat ttgttgctga taagaagaag aagactaatg gagtttgtta a            1491
```

<210> SEQ ID NO 10
<211> LENGTH: 12936
<212> TYPE: DNA
<213> ORGANISM: Nicotiana tabacum

<400> SEQUENCE: 10

| | | | | | |
|---|---|---|---|---|---|
| atggttctgt | ccaagacagc | gtcggaaagt | gacgtctcca | tccactccac | tttcgcttcc | 60 |
| cgatatgttc | gaacttctct | tcccaggtac | atataatatg | tctcaatctt | aaataagtta | 120 |
| gagttaattt | acgtcgtaaa | ttcttttatt | ccattctgct | taaagaattt | atatattttt | 180 |
| caaaaaaaat | ttgatatttt | ttgttgtttg | attgtcagaa | aaagattatt | tgaggaatat | 240 |
| agggaaaagt | cattttctt | actttaact | tcagatcatt | gtgttgatca | acatttagac | 300 |
| gttactatca | atatttaata | ctcataattt | caccagaatg | ctattaattt | gcttatatta | 360 |
| ttattaacca | ttgatctttc | acccaatcaa | acactaattt | ttttctttca | gaaaataagt | 420 |
| ccatttccg | agaaacattt | tctgaaaaat | aactttcgtc | gtactaaaca | cacccatcat | 480 |
| cgctgttgtt | actatgcttc | ttttcattta | atattgagct | gaggatcttt | ggaaatggcc | 540 |
| tctctacctt | tacgaggtag | gagtaagatc | tgcgtacaca | ctatcctcct | cacaccccac | 600 |
| ttgtggaatt | tcactacata | tgttgttgtc | gtaaactaaa | cacacccatc | atcgctgttg | 660 |
| ttactgtgct | tcttttcatt | tttcattgag | ccgagagtct | tcgaaaacag | tctctctacc | 720 |
| ttcacgaggt | accctcgtca | gatcccacct | gtgagatttt | actggatatt | gactaaactc | 780 |
| acccatcatc | acttgcgctt | tcttttccta | agattttctt | ttgtataatc | ttgaaaatgg | 840 |
| agtttctttt | tgaacttttt | tcttttgatt | ttttggattt | ttaggtttaa | gatgccagag | 900 |
| aattctatac | caaagaagc | agcatatcaa | atcataaatg | atgagcttat | gttagatgga | 960 |
| aatccaaggc | taaatttagc | atcttttgtg | acaacatgga | tggaaccaga | gtgtaataag | 1020 |
| ttaatgatgg | attccattaa | caagaactac | gttgacatgg | atgaatacc | tgtaaccact | 1080 |
| gagcttcagg | caagtctctc | tctcttttct | ggattgttgt | gacggagaca | gaatttctgc | 1140 |
| taaggggta | aaaaaaaaa | atttaaaaga | aattgtgacc | ggtagaatgt | atcaagggga | 1200 |
| tttaaaatat | aaactataat | cggattttat | tttgtattat | acagtgcaat | ttttttggtg | 1260 |
| aagagggttc | gagttccgcc | ccctaaattc | gtccttggct | gatcgtgtta | aaaatattat | 1320 |
| acacggtcaa | gtaacttata | atagaattta | acttatatac | atcaatagtg | taaaaaatat | 1380 |
| atttacaatt | aaactttgag | atcagtgatc | ttgaaaataa | aataagttta | ttacaaaaga | 1440 |
| taaaggtgat | gtgacagtgt | gtgaagaatt | tttagtgttt | gtatatatta | gtttagctca | 1500 |
| aaattataaa | taaatatata | taaaagtaat | aatttgataa | aaatgatact | ccttaattta | 1560 |
| ctgatttgta | aaagatcttt | tatactgtcg | tcaatgtgta | ttcttcttc | tcgtattctt | 1620 |
| tggtaataat | aactgataaa | atggtaatta | aaacttctaa | gctaaattac | acaaatttgt | 1680 |
| aaaagatatt | ttacaccgaa | aatatatact | agtataactt | gaatcttcat | tttcgttttc | 1740 |
| tttggtaata | atagtagaat | gccttgttgt | gacttttgcg | tcacaaaaag | aagaaaaata | 1800 |
| gtactgttag | gtttattctg | gaattattc | atctctcaat | gaaactttc | tcaaattcaa | 1860 |
| caaagtgtgt | ggaacagtaa | aatgtcccca | aaaatatcta | actttttttc | tacttttaag | 1920 |
| tgtagcgtag | gagaataaac | aatgggcaaa | taacaaattt | aagtggtact | caagcatcat | 1980 |
| aggcccacgt | cttttttttt | ttttgttcca | atacatgcaa | taatgcaaat | catgtccttg | 2040 |
| atataagtac | tataaataaa | atatcttggg | actcccataa | acttgacaca | ggggcgaagt | 2100 |
| cggaatttta | agtttatgga | tttaaaattt | caatcctttt | aagttactgc | gttctagtta | 2160 |

```
ataatttata aatattcaat cgattttta agtcaaacaa aaattttgga ccaaaactac    2220
tgaaatcgat gcatacgctc ttattccaaa cacccatcca aaaaaaaga aagacaaaaa    2280 agaaacatgc catatatata agttattagt acttcctccg tccaagtttt cttgtccact    2340
ataaaaaata gatatcaatt gttatttatc cagttcaaaa aatcaatgga taatttacta    2400 ttttataccct attttacccct tgttattaag tattagtact tatttccaat tcattttcaa    2460 tataataataa ataggagtaa tatagtaaaa ttattatgtt atttattatt ttttaagacg    2520
tgtgtcgagt caataataga caagtaaaat tggacggata gaataataaa catctattgc    2580
attttgctca tccctacca cctgtctttg ttctacttta gtaaaagatc tttcacttta    2640
ctatagcatg aaccttgcta atcttttca cggttgatag tgtaaaacaa taaaagttac    2700
acctttccct cccaccaaaa atataaaata aacattgatt aaaaactaag ggtccaacaa    2760
aaaatataaa ataaacactg attaaaacta aaggaaaaac aaacataaat gtagatccct    2820
aaatcttgga aagctttaac taaatgctcc ataatcttcg atctcgatac ttttttaatga    2880 gttttaataa atctttccgc gtctagtagc agctcctaca cattttccaa atattaaaaa    2940
caaaaagggt taggtttaga aagaggaaaa agaaagatat ggaccacctg agtgaaaact    3000
gattcggaat ttaaatttaa tcgattcaat ttttgaaatt attaacacta aacttattat    3060
actttaaata atgtgttcaa atttaatatt tattgaatat taatggtttt cacatctcaa    3120
tttaaatttt gtgacaaaaa taataaattc agttgcactc gttgctaaaa taataataaa    3180
aatgacaaag atggttggac ttgttcctcc ttttttttt tgggggcacc atagagagag    3240
ttgtacttat ttttctccat tttgagattt ttttttttaat tattatctca atatttcaga    3300
tagggacatc ctttaaaatg gacaaattgt ggggtaatgg aaaaataatg ttgtttcctt    3360
taatttgttt ttttccttat ggtttacttt accgacatat acgatggctt tgccattct    3420 tctttgggtg gtaatattag tttttttaaa gcgagtttaa attaaatatt aatagttatt    3480
tttgtaggcg attgcaagta gtttaattt aatttttaatt ttatggtact taaaaagacc    3540
ttaaaaaaga aagttgaagt ttaggatttc cattttttcct ttaaaaagga atattctaga    3600
agcattacag tcgacgtaaa aaaatattac tcccttcggt ccacaataag tgattttttg    3660
gcttttatta tggtccaaaa taagtgattt ttccagattt caagaatgaa ttaattattt    3720
gtttcctaca ttgccgttgg agtcaatagt gttggagtat ggtatgagtg tttatgtgaa    3780
gagatagtaa atgttaatat gatcaatttt attgctaatt aatattaaaa ggtgaatttc    3840
ttaatcagtg cgaaaacagt cgaaaaatcc cttattatgg accggagaga gtattaataa    3900
gcaactgttt tgtctaattt ggcagttgat ttgtttaaac tagactatga ttttgtgaag    3960
tttaaagtcg ttttcgatct gtttgaattt gtttctcaac ctagctagac gaactagtct    4020
aacaaatgtc ccataattat atttaaaaaa aaaattccag aaagtctgat ttttttgttat    4080 taaagaaaag tcaattagtg actcctggcc ccaccacgca aagagttcaa atttctgaaa    4140
atttgattag tttagttaat gcataaatta attaatgcat aaattttgac ggggggattta    4200 aactaaagtg aatgaatgac catatgccac aattttttaa gcagatattt tttcctatta    4260
ccattttatc cttcactctg tgctattact ccctctatct catattatgt gtcgtgtttt    4320
tttattacac gcctcttaag aaatattaat taggaaaggg attggactat tctacccctta    4380 tttatgtctt aagatataat ttatcttcat tgaatattta ttctatttat atttttatcttt    4440 catcttcaag aacaattatt actaagggta aaaaaggaaa aaaatatcaa ttttgtcttg    4500
```

```
aacttctaaa atgataaata atttgagaca attattttta gtaaccatga ctgttaatat    4560
gagacgaagg gtgtatagca taggactttc taccacctgt gatcttatat cccctttaca    4620
tattatgtaa actcataaat tgtttaataa cattattatt ttaatttaag ttatagcccc    4680
tttacatatt atttttattat gcatttttat ggtactaata tatcggctcc tgttgctttt    4740
tttgagccga aggtctcctg gaaacagcct ctctacccct cggggtaggg gtaaggtctg    4800
cgtacatatt accctcctca taccccacct gtgagattat accgggttgt tgttgttgtt    4860
gttatatata catcaatact gaacaaaaat tttacacctt caggccagat ttatctattg    4920
tagcaagtat attgacttat ttttatattg caaatttcac actaaaagga agcttaccta    4980
caaatattct ttgggagtat gagtgacgtg ataatgaaaa attttcacag acgatgtata    5040
taacttaaaa tcaaaaatta tatcgacaaa ctaagaatac gtttaatttg tcagaattaa    5100
ataattttaa atctttttat ttttttattt tattttgcag aatcgatgtg taaatatgat    5160
agctcatttg tttaacgcac cacttggaga tggagagact gcagttggag ttggaactgt    5220
tggatcctct gaggctatta tgcttgctgg attagccttc aagagaaaat ggcaaaataa    5280
aatgaaagcc caagggaagc cctgtgacaa gcccaatatt gtcactggtg ccaatgtcca    5340
ggtaagataa atctatattt ttagccgctc ctaaaaatta ataaccgacg aaatatatat    5400
ttgttggtat gcatgtatta tatacatatc tagtaaatgc aattagtttc agccgatcgg    5460
ttaattttgt attttggcca atgttagcct atcatggatc tttacacaaa tagccgattg    5520
aattcattat ttaattttga aatttttaca caaataagcg atatattaa ctatttactt    5580 tttctatgta tatatacatt gattatatat aattatacac ataataatgtt gttccttctg    5640 tatcctctac ttgtaaataa tgattttgga aattagaacg ttagcttata aacgtaaata    5700
taaataaaac agaaattaat tcgagcccac tgaattcaca gtgtttcctt aaggaattta    5760
gtcccctcct agtacccaag gttatggatt atttcctccc aggatagaac gaattacaca    5820
ctggtgtagc ggtacttcaa accccagtgt ttcagcgaac acaaagttcc gcagcaaatc    5880
acacttatgg atgctttgtt tgtagttaaa aataatgcag aataaggagg acagtcgaat    5940
ggaaattctg agaggaagga atgcaaagta tagccaatgt tgaattctta ctgaagagaa    6000
tatcagattg caattcgttt ttccagtgta tacgcagtgt atacagagtg tatatccagt    6060
atatacagag tgtatattta gtgtatacag agtgttttga gtgttttttc cgatgtgttc    6120
ttctttctct ccaacttatg ctctatttat agcagttatt tgagagaaat ccgcccctcc    6180
atggtgcaaa ggtgtttggc aaaggtgcaa gttcctaaac ccaaaggacc gaaacagtt    6240 gattgtgttt tcataggata tgcgactaat agtaaagcat atcgatttct ggttcataaa    6300
tcagaaaatc ccgacattca taataatacg gttatagaat cagataatgc tgagttcttt    6360
gaaaatatat atccgtataa aaaggaatgt gagtcgattg gtgaaggatc taaacgactt    6420
cgggaagaaa caaagaaaag tacatttaat caggggatc caagacgtag taaacgtcaa    6480
agaacgtcta cttcgtttgg accagattgt ggtgcaaatt ggatcaccgg ttcaactgat    6540
tcgaagtcca caagtggata tgtattcact attggtggag gagcggtatc ttggaagtcg    6600
tccaaacaaa catgtattgc ccgctctaca atggaggctg agttcatagc cttaaataaa    6660
gccggtgaag aagcttaatg gctccggaat ttcttggaag acattccatt ttggcctaaa    6720
tcgttggcac caatatgcat acattatgat agccaaacaa caattggaag ggctgggagc    6780
gttatgtata atggtaaatc tcgtcatata cggcgaagac ataaaaccgt taggcaactt    6840
ttctctagag gaattatcac aattgactat gtaaagtcaa gtgataatgt gtcggatcca    6900
```

```
cttacaaaag gcctaactag agaggtagtt gagaaatcat cgaggggaat gggactatgg    6960
ccgagaacaa gtcattgtgg cggtaactct acctagaaga ctggagatcc caagatctag    7020
gttcaaggag atcaaacaaa gtcattaatg acggttcaac attgtcaaca aatatttta    7080 gtccattctc gtgatgagac aatgttcagt accaaggata aaacattaag gcttttaat    7140 gatttctaaa tttaatacaa ggtatatcaa atagtgtatc taagggatga cacgtttagg    7200
aatcacctat gtaagtgtga agtattagcc gcttcaatga aattttgca aggccaattc    7260 cctacgcact tatgaaacca ggcggtgttc atggctgaaa cgaacacaac aatgagaacc    7320
aaagacggtt aagggattga ttgtgtgact tatggttgtc taggtataca ctaaagttcg    7380
acggttcaaa gatatcaaat ctaccgattg accgagtata tccgacataa gttcactacg    7440
gaaagttcaa agggaaacct acttatccag atgcaattaa tccttgtttg caaattacac    7500 aagttttca tgcatacttc cgtgatatag ccattcccca ttcatgtggg ggattgttga    7560 gttttgttt aagatgaaat agtcttaaaa ttagagtgaa tggaaaatgg gatttggatt    7620
tggatttgga ttcggatttg gtcaaatgat cgatcgattg attaattttt tggaccaaat    7680
ttatttgtta atagtgaata ttaacgtgat ataatccgtg tttgtaacgg atgttttcca    7740
atccgtgtat tgtattgcaa cactaagcaa taagcagcct agtgcacctc ccacaatggt    7800
gcaagtgctc ctcccaccaa gcaagtgtac attccaccat gtaagtattt actccatgat    7860
agcctactgc ttgttgcacc atggaggggg aggatttctc tcaaataact actataaata    7920
gagcataagt tggagagaaa gaagaacata tcggaaaaaa acactcgaaa cactctgtat    7980
atacttaata tacactctgt atacactgga tattcactct gtatatattg gatatacact    8040
ctgtatacac tgcgtataca ctggaaaaat aaattgcaat ctgatattct ttttagtaag    8100
aattcaacat tggctatact ttgcattcct ttctctcaga attttcatta aattccttaa    8160
gcttgttgtt ccttctgtat cctgtacttg taaataatga ttctggaaat tagaacgtta    8220
gcttataaac gtaaatataa ataaaacaca aattaattcg agcccactga attcatagtg    8280
tttccttaag gaatttaatc ccctcctagt acccaaggtt atggattatt tcctcccgaa    8340
ttacacactg gtgtagcggt acttcaaacc ccagtgtttc agcgaacaca aagttccgca    8400
gcaaatcaca cttatggatg ctttgtttgt agttaaaaat aatgcagaat aaggaggaca    8460
actcagaagt cgaatggaaa ttctgagagg aaggaataca aagtatagcc aatgttgaat    8520
tcttactgaa gagaatatca gattgcaatt cgttttcca gtgtatacgc agtgtatatg    8580
aagtgtatat ccagtatata cagagtgtat atccagtgta tatagagtgt atattaagtg    8640
tatacagagt gtttcgagtg ttttttccaa tgtgttcttc tttctctcca acttatgttc    8700
tatttatagc agttatttga gagaaatacg ccccctccat ggtgaaacaa gcactaggct    8760
atcatggagg aagcacttac atggtggaat gtacacttgc ttggtgggag gagcacttgc    8820
accattgtgg gaggtgcact aggctgctta ttgcttagtg ttgcagcaca atacacggat    8880
tggaaaacat ccgttacaaa cacggattat atcacgttaa tattcactat taacaaataa    8940
atttggtcca aaaattatc aatcgatcga tcatttgaca aaatccaaat ccaaattcca    9000
tttctcattc actctaattt taaaactatt tcatcttaaa caaaaactca acataataat    9060
acataaatta tgcatgtatt atctattcag cggttattgt taatttaaat ggtagggtgg    9120
tcggctattt gggctaattc ttctttactt ttccttagctg atatacatag attatacatt    9180
aattatacaa atttttacat ccgatgcaat cagtttaaac ggctaggtgg atggctattt    9240
```

-continued

```
agattaaaac tcctctaatt ttattaaata taaatcattt ttgttaccat aagtgtattt    9300
aatatgttgt gatagataat atatcttact ttctaggcta ctaattcaat tttttatgga    9360
ctgtcacctg tatttatctt ttatagcctg tttggccaag tttcttttttg gccaaaagtt   9420 tttttttttt ttttgccaaa agcacttttta gccaaaaatt gaggtgtttg gccaagcttt   9480
tagaaggaaa aaagtgtttt tgaggagaag cataagcagt tttggagaag cagaaaaaag   9540
tatcttctct ccaaaagcac ttttttgaga agcactttgg agaaaaatac atttagaagc    9600
agttttttaa agctgggtca aacactaatt gctgctcaaa agtgcttttc aaactaatta   9660
gccaaacaca aactgcttct caccaaaatt acgtttgaga aaagcacttt tgaaaaaaac   9720
acttctcaaa ataagctgat ttttgcagtt tggccaaacg tttaaatttt tttgcactat    9780
cgtgtagaga agttaaactc tataaaacac atggatttgt ttccaaaatt taggaattga   9840
gagtgctaat tttgtaattt taacaggtgt gttgggagaa atttgcaagg tattttgaag   9900
tggagttgaa agaagtaaaa ttgagtgatg gatactatgt gatggaccct gagaaagctg    9960
tggaaatggt ggatgagaat acaatttgtg tagctgctat cttgggttcc actctcaatg   10020
gtgaatttga agatgttaag cgcttgaatg acctcttgat tgagaagaac aaagaaaccg   10080
ggtaagtcac gatttcgtag agctttttgg ttgttaagtt atagtgtcga ccgaataata   10140 tccataatt ccgacctttc tggtcaatgg tgaatacgtg tttgttcaaa tatctttttt    10200
tttttccttc tctttgtatg aatatcacaa tagaagggga gtcttggagc aacagtaaag   10260
ttatctccgt gtgatctaca gatcacgggt tcgagctatg aaaacaacca ctaatgtctg   10320
tattaggata ggttgtctac atcacaccct ttgtggtgcg attcttcccc gaaccctgcg   10380
tgaatacgga atactttatg caccgagctg cttttttata tatgtaaata tcataatata   10440
tagttgataa tttgtaacag gtgggacact ccaattcatg tggatgcagc aagtggtgga   10500
ttcattgcac cattccttta tcctgagctt gaatgggatt ttagattacc attggtgaag   10560
agtattaatg tgagtggtca caaatatggt cttgtctatg ctggtattgg ttgggccatt   10620
tggaggaata aggaagactt gcctgatgaa cttatttttcc acattaatta tcttggtgct   10680
gatcaaccta ctttcactct caacttctct aaaggtataa ttccttcatt acaagtcctt   10740
aaatatgtgc ttaatccaag gcgaactagg atttgaggtt aatgagttat ggacttgtca   10800
tcaaatccat aactcgtcaa aatcgagttc ggatgatgcc attctctttt tctgaagggg   10860
aactttagag caacgataaa gttgtctcta tgtgacttat aggtcacggg tttgggccat   10920
gtaagatgcc gctaatgctt gcattaaggt cagttgttta tattacattc cttggggtat   10980
ggtccttccg caaaccctat gtgaatgcat gatgctttat gcaccaagct gccttttact   11040
atcataaaac atatgatgct ctaattagct agatatatat atttctaagg ctaaacattg   11100
aaaagtacca ctagagtcat atcactagcc ttacaaatct aatcattttt gctattgtaa   11160
tgcaggttct agccaagtaa ttgctcaata ttaccaactt attcgcttgg gttttgaggt   11220
aagttaagat taattttgtt attttcaatg gagctatggg caggcaattg ctatcattac   11280
ttctaagttc tattagtaca atttaatcaa ctatcaattg cataaaaata cgagtttaaa   11340
ttatatacat catcattcta actaattttt acactatcat attacttttta tgtgttatat   11400 caagtaacca gtcttaattt aaagattaca aatctcgcat tttatggtgt ctagcctatg   11460
gatatctttt gaatgacctg atgtaagaaa cttgaactct aaaaataata tcttttttcac   11520 aaacaacaca ctttaaatat actctttaca atctgaaatt tccgaaagtg aagcctcggc   11580
gtaactggta atgttgctac aatgtgacca gaaggtcacg ggttcgatcc gtaaaaacag   11640
```

-continued

```
actcttgtag aaatacaggg taaggctgcc tacaataggc tcttgtggtc cggcccttc    11700
cccgacccca cgcatatcga gagcttagta cattagattt ttttttcttc acaatctgaa    11760
acttctatgt aaaacaggg ttacaagaat gttatggaga attgtcaaga aaatgcaagg    11820
gtactaagag aaggacttga aaaaagtgga agattcaata taatctccaa agaaattgga    11880
gttccattag tagctttctc tcttaaagac aacagtcaac acaatgagtt cgaaatttct    11940
gaaactctta aagatttgg atggattatt cctgcatata ctatgccacc aaatgctcaa    12000
catgtcacag ttctcagagt tgttattaga aagatttct cccgtacact cgcggagcga    12060
ctggtaagta tcgttacgcc tcagttccaa ataagttgaa attagactat ataaatcgtt    12120
acttcttcat ttaaacgaaa agttgtgtct tacaatgaaa ggacatttca acccatgcaa    12180
aagttttaaa aaaaaagata ttcttgtctt ggcatctatt atcaaaatat cttttttctt    12240
ttcctccaaa aaacacttct tttctttcca aattatgtac ttaaaaaaaa acttgaaata    12300
tgtcatgctt tactaaccaa aactctccac tatttcatta gcacagaaat ttgaaagact    12360
tgtcacttgt tatatttact agaagaatta accctaatag cagctcagtc gaccacttaa    12420
ataaaaaata atcagtagat gaataatata tgcataatta atatacaaag gctatttgca    12480
ttcaatccct ttgtgttttt ttaatcgtac tttaaatttt agtgggcgtt tggacttaag    12540
aattgtaaaa ttccattaaa aaaaagtgaa cttttttga agtgaaaatg attttttaaaa    12600
attagagttg tgtttagata ttaatataat ttcggttgtt tttgaattt tgtgagtga    12660
tccgagtaaa aaattttaaa aacagcctgt tggagttttt caaatttcg aaaaattcta    12720
aaattttatt ttccgattca acaggtgata gacattgaaa aagtcctcca cgagctagac    12780
acacttccgg cgagggtcaa cgctaagctc gccgtggccg aggcgaatgg cagcggcgtg    12840
cataagaaaa cagatagaga agtgcagctg gagattactg ctgcatggaa gaaatttgtt    12900
gctgataaga agaagaagac taatggagtt tgttaa    12936
```

<210> SEQ ID NO 11
<211> LENGTH: 496
<212> TYPE: PRT
<213> ORGANISM: Nicotiana tabacum

<400> SEQUENCE: 11

```
Met Val Leu Ser Lys Thr Ala Ser Glu Ser Asp Val Ser Ile His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asn Lys Leu Met Met Asp Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140
```

| Met | Lys | Ala | Gln | Gly | Lys | Pro | Cys | Asp | Lys | Pro | Asn | Ile | Val | Thr | Gly |
| 145 | | | | 150 | | | | | 155 | | | | | 160 | |

Ala Asn Val Gln Val Cys Trp Glu Lys Phe Ala Arg Tyr Phe Glu Val
                    165                 170                175

Glu Leu Lys Glu Val Lys Leu Ser Asp Gly Tyr Tyr Val Met Asp Pro
        180                   185                 190

Glu Lys Ala Val Glu Met Val Asp Glu Asn Thr Ile Cys Val Ala Ala
            195                 200              205

Ile Leu Gly Ser Thr Leu Asn Gly Glu Phe Glu Asp Val Lys Arg Leu
      210               215               220

Asn Asp Leu Leu Ile Glu Lys Asn Lys Glu Thr Gly Trp Asp Thr Pro
225              230                 235            240

Ile His Val Asp Ala Ala Ser Gly Gly Phe Ile Ala Pro Phe Leu Tyr
               245                250            255

Pro Glu Leu Glu Trp Asp Phe Arg Leu Pro Leu Val Lys Ser Ile Asn
          260                 265              270

Val Ser Gly His Lys Tyr Gly Leu Val Tyr Ala Gly Ile Gly Trp Ala
        275               280              285

Ile Trp Arg Asn Lys Glu Asp Leu Pro Asp Glu Leu Ile Phe His Ile
     290               295               300

Asn Tyr Leu Gly Ala Asp Gln Pro Thr Phe Thr Leu Asn Phe Ser Lys
305            310                 315            320

Gly Ser Ser Gln Val Ile Ala Gln Tyr Tyr Gln Leu Ile Arg Leu Gly
              325               330          335

Phe Glu Gly Tyr Lys Asn Val Met Glu Asn Cys Gln Glu Asn Ala Arg
          340               345              350

Val Leu Arg Glu Gly Leu Glu Lys Ser Gly Arg Phe Asn Ile Ile Ser
        355             360              365

Lys Glu Ile Gly Val Pro Leu Val Ala Phe Ser Leu Lys Asp Asn Ser
     370             375              380

Gln His Asn Glu Phe Glu Ile Ser Glu Thr Leu Arg Arg Phe Gly Trp
385            390               395            400

Ile Ile Pro Ala Tyr Thr Met Pro Asn Ala Gln His Val Thr Val
             405               410           415

Leu Arg Val Val Ile Arg Glu Asp Phe Ser Arg Thr Leu Ala Glu Arg
          420               425             430

Leu Val Ile Asp Ile Glu Lys Val Leu His Glu Leu Asp Thr Leu Pro
        435             440              445

Ala Arg Val Asn Ala Lys Leu Ala Val Ala Glu Ala Asn Gly Ser Gly
       450            455            460

Val His Lys Lys Thr Asp Arg Glu Val Gln Leu Glu Ile Thr Ala Ala
465              470              475            480

Trp Lys Lys Phe Val Ala Asp Lys Lys Lys Thr Asn Gly Val Cys
            485             490           495

<210> SEQ ID NO 12
<211> LENGTH: 526
<212> TYPE: DNA
<213> ORGANISM: Artificial Sequence
<220> FEATURE:
<223> OTHER INFORMATION: synthetically-generated oligonucleotide

<400> SEQUENCE: 12
aattggatcc gagttgaaag aagtaaaatt gagtgatgga tactatgtga tggaccctga    60

```
gaaagctgtg gaaatggtgg atgagaatac catttgtgtt gctgctatct taggttcaac      120
actcaatggt gaatttgaag atgttaagcg tttgaatgac cttttgattg agaagaacaa      180
agaaacctaa taagatcttc aacacctaca ccattttttt aatcactact acccattgca      240
ttgaacaaac ttccaagttc ttcttagctt cagattaaga aagtacccct tcttggcttt      300
gttgatgtgg taccattgtc cattgtcttg tgtgtttccg gtttctttgt tcttctcaat      360
caaaaggtca ttcaaacgct taacatcttc aaattcacca ttgagtgttg aacctaagat      420
agcagcaaca caaatggtat tctcatccac catttccaca gctttctcag ggtccatcac      480
atagtatcca tcactcaatt ttacttcttt caactctcta gaaatt                    526

<210> SEQ ID NO 13
<211> LENGTH: 708
<212> TYPE: DNA
<213> ORGANISM: Nicotiana tabacum

<400> SEQUENCE: 13
atggggagag gaaaaattgt gattcaaagg attgacaata caacaagcag gcaagtgact       60
ttctcaaaga gaagaaatgg gctgctgaag aaggctaaag agctagcaat tctttgtgat      120
gctgaagttg gactcattat tttctccagc actggaaaac tctatgaatt ttccagcaac      180
agcatgaggg ctataattga tagatacaac gagatgaagg aggagcatca taacctcatg      240
agtcctatgt cagaggtcaa gttttggcaa agggaaatag caagtttgag gcaacaacta      300
cattacttgc aagaaaatca caggcagctt ctgggtgaag aactttctgg actcagcatc      360
aaagatctaa caaatcttga aaaccaactt gaaatgagtt tgaaaggcgt tcgaaagcaa      420
aaggagcaga ttttgactga tgaaatcaga gaactaaatc agaagggcaa tcttattcat      480
caagaaaata tagaactcta taaaaaggta aacctcattc gacaagagaa tacagaattg      540
aagaaaaagg tttctgagca aggatgtgga agtgaaccaa atgggggtgt tcaggccaca      600
catgcaatca gcaaaggata tgatgtacat gcaccaatca gtctccagct aagccagcca      660
caaacacaga gagtgtaac atcaacaagc gtcatgcagc ttgggtaa                   708

<210> SEQ ID NO 14
<211> LENGTH: 15537
<212> TYPE: DNA
<213> ORGANISM: Nicotiana tabacum

<400> SEQUENCE: 14
atggggagag gaaaaattgt gattcaaagg attgacaata caacaagcag gcaagtgact       60
ttctcaaaga gaagaaatgg gctgctgaag aaggctaaag agctagcaat tctttgtgat      120
gctgaagttg gactcattat tttctccagc actggaaaac tctatgaatt ttccagcaac      180
aggttagtta ttttttacatt tttaatttta attttaattt ggtcctaaac atagagatat      240
ataatttttg cattcttcct ttttttttttc cttttctttt gggaaaagtt tggactgaaa      300
tatgggattt tttcctgctg tagaactgcc tctatttcat atattctgta cttcttgcat      360
atcgttttat gtaatttttt tgtttaaaaa ttaccaattt ggtacctttc catttactgc      420 tatttttttat taaaaattat taccaagttg gtatctttcc agtttgtact ttgtatgtga      480
aaaaagagta gtcagatcat atcatggatt aacctttgtt actgcatcaa gattccaacg      540
tgcatattta taaatgcatg ctacgttact ttcagttgtt ttttcttttc ttttttttttt      600 ccaagtatat tgggagaaat ctaaaactag ctttgctttt ttaatccagg gattaaattt      660
gttaatcatg cacgaggtgt tttatctagc ctggcccatt ctatacaaac ctaattaatg      720
```

```
ttgaaaaaat gactcgagga acaacatgca ccaatcctaa agaaaaccta ataggagtag    780
taatatttgc aaatctgaaa tctgtccgca ctttagaatt tggtttaaag ccctgcagtg    840
ataaatatct ctattgtatt ctatttggtg caagtaagaa ataactcttt agagcacgtt    900
tggatgggaa acatgttata ccatcattaa ttattccgga attagttatc ccgagattag    960
ttatttaccc ttacaatagg gataaacaaa cactacaaat ctacaacccc gggataatta   1020
tcccaggatt aattatccca tatccctcga tattgttatt ctctcttcag tcttcacata   1080
aaccctaagg tgtcatttgg tttaatgatt agaataaagg catatgagat ttaatacaat   1140
tcgtgtcctt gatcttattg agttaatccc acatcagtga atgcaaacat tattatgctg   1200
ccaaatatat tattctacta aactaacaaa caggatgctc cttaattcta cgtatgcatc   1260
cagaaacttc tgtcactctt ttgtggccct cagataaact cacataagta gcttctcaca   1320
taattagaat actttgtact acctttctat acaaccttct ttagacgcat gcataattta   1380
cattagaact tttaatcttt tcatcaagat atacttgtga tcactttaat tatgtgtata   1440
ttttgcttcg aaattgccta aatagaattt cgtcttatgg aatatagact cacaagtgca   1500
gaatcatacg tatagtttaa tatggggctc agataactag tttaacacat gaatttgact   1560
catacactaa caatgtaaca atttataagc tgttagtgta ttttggcgag ttacctgtct   1620
tattactcct acttattatg catcatggat aattacctat aattatcttt taggtgattt   1680
gataatgtaa agtttaaatt cattatgtta gtgtgagaag ttaaactctt gacacaatta   1740
tatatttgct atgttaccag catgagggct ataattgata gatacaacga gatgaaggag   1800
gagcatcata acctcatgag tcctatgtca gaggtcaagg tatagctctt taattatatt   1860
taaatctgct tcagaattgc ctaaatagaa ttcgtttgat ggataatgg acttgcaaag    1920 gtagaatcat atgtatagtt taatttggca cacagataac tagtttaaca caggaattta   1980
actcatacat atacattggt tatatacata aacaccaccg attttttgttt tcacaagtgg   2040 ttgttaatag agaattgcga gtgtatgtaa tgtccctttt tggatgttct tgtatactag   2100
actagatgtg ttcatcgta ctcaataccct tgtgagaagg gatttaggaa aagtctgctc    2160
tcattctatg tcagagaatc taaacttcca attaaaaatc tttaagataa tggattaaat   2220
attctttgct atttaacctt ttaaatgatc ttgtatatcc attgtgggat atatatatat   2280
tgagtaactc atcaaatgtg gagcagatag gctcgaacta aatgttatag ttggaaattt   2340
tcaggttatt attcttatcc ttcaaccacg cgtgtggacc tctatgggaa acattatcta   2400
tttaattttt catttggtt agctcaaata tattctgtcg aaatctcaat caagatagt    2460 ataaggccag aatttgaaag atgattcatt ttttaaagtt ccacgtgata tctttataag   2520
ctaaatatga atgatgcaag ctttcagtca aagagattga aacagtcatt aatcaactat   2580 ggcacccta agattgacct cttttttaaa tgaacctctt accctggcct caacaatagc    2640
ttttgagaaa attgattgct aaatgatttc atattacttt atgttacaat taattgacaa   2700
gtactttgat taaacagtaa atcggcgaag gatcagatta gccacaatga catcgacaat   2760
ttttttctta acagtgctgt aacagagaag cccagaaaga gcacttatag tctccattat   2820
agaacaagag ctacaccatt ctgtttgaca atagttgatg atggcaagtt agctgtagct   2880
tcatttccct tttgaggtag gaattgtata aaaggcttgg aattgtaaaa atacaaaaat   2940
ttaaaaatgc aaattaatgg agagttgact aactcccaaa aatagattgc tatggagaga   3000
gaacagatgt gaataatagc tcttgatctt cacacatggt caaggtgcga ctagattaaa   3060
```

```
gcaaatacaa attcttcaag aacaacaaaa ggttttaag caggtttttt caagcaagct    3120
cagttgaagg ctcacagtgg agtttaggga gggtcaaaaa agttttcatg atgatcaagg    3180
tcatcctttg gcccaaacta actccatatt atgttatcag ccttttccca ttcctttatt    3240
ctcgagttca ccccgtcttt atcatggctc acggaagtct tgcaaaaagt ttcaagaccg    3300
caggatccac ctatgtgaat ttcgtgtatg cattaagaat tcagtaacag taggcattca    3360
tctgaagtgg ctgctctttc tgggcatctt gccccattca aacttttagc tatgttagcg    3420
tggtcagtgt tcttcctctg cgccaagga tggctaggaa ataccaatgg aacacctgaa    3480
ctgggacaat ccacccacca ggttttggtt ggtatatgtc agattcgtta actgactcca    3540
tggtaacttc tggtaggtat cttctcaaca tggttatgag agagattcaa cttactagaa    3600
aaacagaaca cgatattaga gagccaaaca gtcagaaaag ttaatgacat atagcaaaag    3660
ctaaaacacg aaatgtaaat cagcaaactc atagagaaag gataaacaga atctttgctg    3720
tgcaccttag tgactgggtg aggaggggga ataatcctca ctttgttgat gttctggttg    3780 ttttttgctgc cttactgct tcatttttcc tctctgcctg ctgggaatt tcatcaactt    3840 ttttttttat taaaaaaagc tacccattat aagacttcac acattcttgt ggtgcaatgc    3900
tacacttctg gaacttcca tgtgttggtt ggtactcttt tatctttttc cacttccata    3960
ctcttcttgt acatcctctc atgtatcttc ttccatggtt ctgctatctt cttgttattc    4020
tcctttgccc tcttattcct gcttattaat tgttggctga ttccctgaat agatgcctat    4080
cttgttgtcc ctttttcct tctcccccta cttcatgttc ggttcttatg cttgctcgag    4140
acaacaacct gcttcctcct aattggtcac ttcaagcatc gatagttacc attgactgtt    4200
aaccttcttc caatgcaaat atatctgact cattagttct atctatgatg tgttgtcaat    4260
tgatgttgat gagatggttt agtaaacata aggggggatg gagtccctgt tggaggtgtt    4320
tgtgttgaaa ggcctctagt atcattccct cgcgctataa tccctctccc tgttccttaa    4380
tctaggaagc tcgataaacc ttgggattaa ctccagtcaa atacttgatt cctgttcttt    4440
ccttggagca gttcgatcaa gtggaatcaa atcctacagg ctcatatgct aacactgcca    4500
ctcagttact ctataagatt tctataagca tgaagagaat tttgtgtcaa atgctgtatc    4560
tcatgacgat gtaaagaaag ttaaatggta agcttatttt gaaaaggatt ttggaatcgt    4620
gctttgatcc caaaaggtgc tgccttcctc tattagggtt aaagctttat tagcacaaat    4680
tgggacttct gttagggttt gttccggtgc caattaattc gtaattgtgg cctattgtaa    4740
cctaactaca cgctcattca gagttccaaa caagttttac tttatcaaat ccaaggatcg    4800
attcttgaat tgcaacacct acgctattat atgtcatact agtgaactac tttgatggaa    4860
cctaaacaaa tacagtaagt catctataat catctataag atactgaaaa cagaaaccca    4920
acctaaaata actaacaagg tctcttctca agttgagtg atccatagtt acctccatgt    4980
ttccactact aacctgaaaa atccatgagc tgtgtagaga attcccttaa agcctccact    5040
acactctggt tcctgtattg tctgcattac aaaatagcag gtttgaacct gtttcaggaa    5100
gtttttccta ccctccttcc caatagtaag catagtccca taagtgaaag gaagcaataa    5160
gtatcaactc ttaatcaagt ggtaaatact atcatcttaa gagttatcca gcatgataga    5220
tacttattat ccatctacat aatataccac ttatcatatt tgaatcaggt catcatctcc    5280
agagacagtt atagattctg gctgatgcag catttgttgt tccaacaagt tctatataag    5340
cagaaagcca aaccacaaga aataccatat cagatcaaac agatgcatgt tggaaattgg    5400
aatagtttat cccagacaaa tagtgcagga acaaactgat accggttctt tttcccagtt    5460
```

| | |
|---|---|
| tatgttgcac tagttttgag accaaaagtc agccatcaaa cagtcatgat gcctgaaata | 5520 |
| agggaggtca ccggagaata aggtggcgac aaaactagta atgctcaccc gttacagttt | 5580 |
| aattccactc caccatgtgc actgacaaga gaatataacc taggggaatc tgcctgcaga | 5640 |
| tgagataatt aggctaacaa gcagaaggaa tacgatggtc ttgacatgat aagccggagt | 5700 |
| ttagagtttg tttatctctg cataagcaga atccatgatc taattaatca actaaaccat | 5760 |
| aatccaaaat cagttgaggc cggctatatg ttcctatata tccattctgc tctgaaactg | 5820 |
| ggatctaatg cctctttaat ttgcatttgc agaaatgaag tgaaatccca aaaagacatc | 5880 |
| tgcaatgcta ggttgaaggt ccagatgaga cactatttta acaaattcca ttagaggata | 5940 |
| gttcgtttgt ctaacagaga atgctttaaa attgcagatc cctatatcag aggagaggat | 6000 |
| ggaggatgtc tcaaccccac ctaaatcgat ataggatcta ctctcagagg taagtaatat | 6060 |
| aaaattttca aaaggaagt cattccacaa acacaaaata taaaaactca gttggatgaa | 6120 |
| atgtctacac aagtttagcg attgaaaacc ctaccaaagg tcctacgtga cacattatga | 6180 |
| caatttgctc aacatcgcaa ctatttatag attaaattag atggaaaacc taagtttgaa | 6240 |
| ttcctatcca tggataccgt aattaaatta taaagataaa tagtcttccc catctaggga | 6300 |
| gcatagttca tggagcaaat tcatgtgata attcaacaaa tggaacctaa catatctaat | 6360 |
| aaataacctg aacctgagtg tcctggtctt ctgtctcaaa ctagcatcta ttcctggtat | 6420 |
| tgcatctcaa atatgaccaa atccttcact ggtgctaaat cctacttttg tgctctcaag | 6480 |
| ttagcatcta ttcccttcgt tagtttaccc actgtaactg acggtcacgt ccaacgagag | 6540 |
| cgtgagcatc acactattct ttcttctcat ggaggcattc tactagcaaa gaagactcct | 6600 |
| ataagtggta gcaccttgtt ggggctttgt ggtataattc tttgccgaaa gaggtctctc | 6660 |
| cagtgttgca tgtttatatc tacgaccgat ccctcaccag agctgacgga catctcaggt | 6720 |
| aaccatcctt gacttaccga catgtcaatg aggatagcaa aaaaggtatc caactgggaa | 6780 |
| gaaggcagtg agggtataag tattatcaga aatttcaaat gacaagaaag taaaagttca | 6840 |
| ggtgctccat aaaatccaaa tcatatatgt caatgaccaa gggcatgatt aatcaaaaca | 6900 |
| taccatggaa tatggattca tggttttcta aggctggagg caagcaagga cattaggaaa | 6960 |
| atcttgcaat gattcctgaa gcagtcattc cggttggaaa aaaacaccct tgaggccttg | 7020 |
| accatccgag gaggataacc tgagagtaaa tggacatgaa cacagatgaa atatattcaca | 7080 |
| tacatatcaa gttcataatc catccacagg agttctctat attcctccag gacttcaatc | 7140 |
| tcactacgaa tccgtcatta aattgtcaat ggtaaaagtt taaaaattgc atccttccag | 7200 |
| cctgaaagac aatatcaacc ccaaccaatg tatgtgctat cttcagacgt tcatcgctaa | 7260 |
| agagtttgtt tcttattgct atggaaaaac tgagacacga tacattttg ccgtacattg | 7320 |
| tttaccacta gttgatctct attatcaaac acgggtgtca agttccattt tacctgttca | 7380 |
| aaaaaagggt gtcaagtttc ctatttagaa aattgggcag ggagcctaca ggtcgaagag | 7440 |
| atgcacaatt acaatctcag agatccaact gtctaaagag ttgacgcaca atagggggtgt | 7500 |
| acaaatgaaa ccgacaaacc gcaccaacca gataatccga gtcaaaccgg aaaaaaaac | 7560 |
| cgcctatagt ttggtttgat ttggtttggt gttggaaaaa aaaatccgac catatttggt | 7620 |
| ttagttttaa ctaaaaaaaa gtcaaagcga aaccaaacca acccgacatt atatgtgtag | 7680 |
| aagtttaaaa tatattttaat gcataaaaat atttattgta gtgtagttta taaatatttc | 7740 |
| ttaaattttt tcataatttt atcttttaac gtattatttc aaacttgact tataattttt | 7800 |

```
ggatgctcca ataaatttta tagtccataa atgttagtaa ctcaaataaa tcctaaacca   7860
aaatcaaatc aatactaatg ctaataaaaa acattcaatt caattgtact atgaatgaaa   7920
atagtgttgg atatctattt ttaagcttat tcatgattta gataaaatgc ataacttatt   7980
tttcttttat agtgtttagt catgtaaata atagtatata gtcgtaattt ttaaattatg   8040
tttgttttca ttatggctta ttaataatat ttattttgtg caattttatt atctttatta   8100
ttgaatattt tagtacaatg ccataactca tccaatattt atgttatttt attgaaaaac   8160
accttatata gttctgtctt actagattaa agaaatattt ggagcaaaaa ttctatgttt   8220
tgtgctatga agactttatg aaaaaaatcc ggaaaacccg aaaatccgaa aaatccgaga   8280
aaaaacgaga ctaaaaaacc tgacttttat tggtttggtt tggtttttag atttaacaat   8340
ccgatacaat tggtttggtt tggtaattag aaaatccgaa ccaactcgac ctatgtacac   8400
ccctaacgca caacaatgca gatggagttc ggggtgctta tcgggtggat aaaattacgc   8460
ttaacggtta tcggattata aatgttgtaa tccgctaacc atccaataag ataatgggca   8520
gattggtatc gaattgacaa ttatcgggca gtttatcggc taaacaaaat aaaaaacttt   8580
tgaacaatca agtacataca agaactactg ataaggaaga cataacagat acgagctaat   8640
ctatgctaaa catgaagaaa actagcttcc tccatcttac tacagatcta cctaacttta   8700
ttgagctata atatgagcca acggtagaag ttagggattt agagcctgtt tggatgagct   8760
gatttgatgt acctgataag cattaggtgc tgaaaaacac ttttaagtct tgaaactgat   8820
ttaataaata agcagttacg cgtttggata caagtgctga aattgataat aagctgctac   8880
agtatttgat aaaaaagtgc tgataagctt tttttctgtt aaaatgactt aaataacctt   8940
ataagtattt cacctataa gggcgtaata tcttcagaat tttagattcc aaatcgatcc    9000
aaatacaaaa tattctattt gtcatttat tttaaataca actgtgcttc gataagataa    9060
ttttatgata aatataattt attttatgac aagcatataa tcataagtta taataattaa   9120
taaattgata aaagtttctc agtaaaaaat aaacctaaat aggacaaaat atttgaagag   9180
aaacaaacac tgtctttatc agcacaacac gtagaaagca acataccaaa aatttgatat   9240
gtcctcattt attatataca attcaaagat taatacacaa atcacataga tataaatatg   9300
caaaggaata gagaatttgc ttatcttaaa tagtcaatga gcattgcaga cttgaagagg   9360
cggagggagg gggttaggtt gaaatagtac tcgaggcatt gagtatcgat gcaataaca   9420 ttatcgtgt ttacacctat aagggcgtaa tatcttcaaa attttagatt ccaaatcgat   9480
ccaaatacaa aatactctat ttgtcatttt attttaaata caactatgct tagataagat   9540
aacttttatg ataaatataa tttattttat gataagcata taatcataag ttataataat   9600
taataaattg ataaaagttt cttagtaaaa aataaaccta aataggacaa atatttgaa   9660 gagaaacaaa cactgtcttt atcagcacaa cacttagaaa gcaacatacc aaaaatttga   9720
tatgtcctca tttattacat acaattcaaa gattaatata caaaccatat agatataaat   9780
atgcaaagga atagagaatt tgcttatctt aaatagtcaa tgagcgttgc agacttgaag   9840
aggcggaggg aggggtttag gttgaaatag tacttgaggc attgagtatc gatgcaagag   9900
ttttgttcta aaaagaata ttttaaagat aaaataataa aaattttggt caaacttaaa    9960
gtgcttataa gctaaaaatt tataagttgg gggttactag cttacggctt atttttttact 10020 tataagcact tggcttataa gtactttta ctttaccaaa cgcgtagata agctactttg  10080
accagcttat aagcttagcc aaacaccctc ttagccgttt aggtttcaa tagtactta   10140 tatacatagg ggaaaaatg taaatataa aattcttaac gggttaacgg tttacccgat   10200
```

```
aagaaatttg agtaatctgc cccaaatcgt taagccgtta attataaaat ctcaatctgt   10260
tcaccatcca ttaccccgat aatccgatac caataagcca ataagccatc ggtttggttg   10320
gttaacggtt ttggtttgat tttgaacagc cctagatggt gttttttggct aagagattat   10380
ttctacaacc aagctctgca ttcgtaataa atgttttttt ctccctgaag accagggtcc   10440
gcttggtaca tggattgcgc atatgatagg atatgtaact tcgtatgcat gtattctcga   10500
caagattaat taactcaatc tggtgaggac aagattatta attaggcagg tactcaatag   10560
agaatttgct tattacattc tatataattc attgctcatt attccacata gtcattccta   10620
gggcattaaa cttcatagtt acccgtgata atcacaggtc cccaatagat gattagttga   10680
ccaaagatcc caaatgtcta aggtgctgaa agaccaagaa tgcatatgta aattttgtga   10740
gaagttaatt cttaaaccat gttgagcaat tgtaacagag gtttctttct tgcttcctga   10800
agattagctg tcatttctta cacagactgc tcacctgaaa aggtttacct cccccagttt   10860
ttagctaggt acattaatct taatcttaag agactagaaa actgatcggc agataactat   10920
taatctaggc cagcaattag tataagaggc aaaaggttca ccatacaaat agaggataag   10980
cccttctttc atttcttttc ctcaatctcc tcctcttaat cctttcttcc aggtccaact   11040
tctgctttcc ccaacccacc cacccacacg tcagtccttg accgtccaca tgcacctttt   11100
tcccccaac ctttcccact atgcaatttc aaccctcacc ccttgggaac taggggtggg   11160
cattggtcgg ttcggtttgg ttttgtagaa gttcggttta gtttattcgg ttttcggttt   11220
gtgattttaa taaccaaaac caatcataa taacttcggt ttggttcggt ttattcatgt   11280
tcgattcggt ttttcggttt caagccatgg caaaaatagt atgaaacaac gaaaatagat   11340
tacttgtgag agaatagcca aaagggtaa ccaaaaacat attgagtgct tataaatatt   11400
ctccatttat ttttgttaga ctgcattaat ggtcatataa tataatgaaa ttctatatat   11460
atccaatcag tgaaataagt gaatgattag catgcgaatt cagatgatac ggaagaatga   11520
attgtgcgaa tgaggctttg tttatttttc tgtagatccc attcacccgt tactaaaatt   11580
caaatacgaa gaaggattac atcaattccg caatatccgt tggggttaaa attcttgttg   11640
tattttatat tgttcttaat tcggttataa ataattcggt tttgggttta ggctaaaaaa   11700
attcggtttt tcggtttaac cgaaaaccga accattaaaa ccgaccaccg aacttttaa   11760
aactataaac cgcaaaccga ccgaataaac cgaaaaatcg aaaccgaata aaccgaaatt   11820
ttcggttcgg ccgattttt cggttcggtt cggtcggtat tatgcccacc cctattagga   11880
acccaattat ttttgcctct ccttaacatg atccttcttc tttccttcca tgacatcatt   11940
ccctcctccc tccacccatc cctaacattt tacaaactat cgtggcatta aaagtatgaa   12000
gcatgctatg aaatttggaa aaagagcgat agatcataaa cttacggaca ccataaaagt   12060
aatgtagaac cattttgggg tagatataca acgaaggcta tatgctaaga agattcatga   12120
aaatttattg caagaggaag aatctacaca gcttagagaa agcgaatgag aagagtgcca   12180
agaaaagctt ttggtgggta atgaagaaga aaggaactca tattaaatat ataatatcat   12240
aaatgatata tgaaatagtt gtcactagtg tgagaacagt agtacgagat acaaagagtt   12300
tcccataacc atgtttttac acccagaata ggcattgagc cttgtttacc ctacttatgg   12360
atgagctaac tcacactata tagtttgagg ttacattgta catgctattt tcaaatggca   12420
ttgtgctaat tgacgaaacc atcaaggata tcaaccaaaa cttgaacttc tgatacgcac   12480
tctaaaaagt tgaagtttta ggataagtaa aagtaagaca tgcattacaa gtttagcccg   12540
```

```
cataagaaga gtgaagttga ggtcagacca aacaagattg caaggtttaa aagcaaccaa   12600
ttcatatatc taggcttgat gttcgaagag aacggcacaa tagatgggga tgttacacat   12660
ccaatcaaaa tagagtggtt taaatggaca tttgctaccg gagtattatg taatagaggg   12720
ataactacca aagtgaaatg caaattctat aaaacgattg taagaccagc aatattacat   12780
acatgggagt aaatgtaggt ctctaaaggc tccaagtatc cacaagataa gtggcgcaaa   12840
gatgaatgat caagatccaa attcagatga atgtatttac tttctataaa ctttcaagtt   12900
acgaaaaagt gctacataga taggtttgaa caaatgagaa tagatatcga ggattcatat   12960
agttgagccc gtctagtttt agattgaatc gtagttgaaa caaaactaag aacgttctac   13020
atctaatatg tggctctcat catcctaaag tacttttctt gtatggttga atttatcatg   13080
ggttgcaata atcatcaagc actacaaaga aagatcaaag caatatttac ctgatttcat   13140
ctcaggaatt atttagcctt ctaatttcat cttctaagca ctatacttat ttttctttct   13200
ttccttggtt ttggctagtt ttggcaaagg gaaatagcaa gtttgaggca acaactacat   13260
tacttgcaag aaaatcacag gtaaattgat ttgacaaggt atatctttta catgcctctt   13320
tatgccacag gatcttttat tgtacacact atagattgaa caatgtgata cctttataca   13380
ctataaattg agtaatttga taccatttaa tatattgact tgtgtgaaat ttattatagg   13440
gaatattttt tagttaaatc ttaatacgac cctcacgtgt cagttttttct ttttctagtg   13500 gatcgagtac ataagaaatc attccatgaa ggatagcgat gagactcgaa ttcaggattg   13560
taaattgtca aaactcaaaa ctacctcgcc tgagttaact gctagggagc aaacatttat   13620
atttatttat tctagttctc caagatagat tgttaagtca tttttttttt ttgcctactt   13680
tgtattctta taagtttcta tgcataaaaa agttaaaaat tttattggag ataaagtttt   13740
aagtaatatg agcacttgac aaatccaatc aacaatcaaa cccattatta cttttacttc   13800
atacacaaac aaatgccatt tgggtaatt aaccagaatt tctaaaacat catcaaaatt   13860
tcttcatcat gtttccgaaa atagttatga tattttgacc aatcacattt ttttatacaa   13920
taatctacac ctacttatcc ccagctgttg ctggtgcttt cagttgaata tgcaaggact   13980
tttaggggct cttttctagt gtttgaaaca gtttaaggtt tctcaaagct tctttttttt   14040
cttttttttt ttgagtaagg tgacaggttt ctcaaagctt cctcttatca tagtctttac   14100
acttggggcc atttaaggat tggaaaacag aacaaaaaag gaaaagatg ctgcatactg   14160 attttgtttt aaggttcatt tctcacaagc attagagtaa ttcaggtttc ttgaagcttt   14220
tagtcaaatt tatggtttag agcaaacact gggaaaacag aacaacacaa agatgccatg   14280
attatttaat ttagaggtta taagatacac tcctagcatc tcttgggcac aactgaagtt   14340
aaaagtgccc aacagaactc taaaccgagt aaaataattt tctacagctg aagttgctag   14400
cgattgattg ctagtaataa gaagaactat aacaataaat gtagacacca aaatttaact   14460
aaaaagccaa aaacctagtc aaactcaaat atcataaaat taagtcgatc aagaagaac   14520 ttgcaaaatg cccaaaaaca aaatttttaa aaaatctaag gattactaac gaaaaaagac   14580
atccaagact tgaatttgca atgttttctt ccatgttttt ctgtgaacaa ctcctggagg   14640
agggaagaat aactataaaa aatattaaga tgaacatccc cttcttttgt agcaacgtat   14700
cggagcttgt cggcatgctt aacatgcaat taaataacaa taaacgtgt atatttcaat   14760 gtctgagatc tagcttagta agctaagctg caagggaga aatattttaa ctaatcccttt   14820 tcttttatga accacaggca gcttctgggt gaagaacttt ctggactcag catcaaagat   14880
ctaacaaatc ttgaaaacca acttgaaatg agtttgaaag gcgttcgaaa gcaaaaggta   14940
```

```
aaatccacac ttttaaaatt cttttgtggt catgaaactt atgtttatat agtctacaac    15000
ttatcctgaa tgtattactt tttcttgcag gagcagattt tgactgatga atcagagaa    15060 ctaaatcaga aggttctact agaaaaacca tcagaacttc ccatattctc ttgtctttaa    15120 aattaccccgg atgattaata ttgcttctgc agggcaatct tattcatcaa gaaatatag    15180 aactctataa aaaggtaaac ctcattcgac aagagaatac agaattgaag aaaaaggtat    15240
taatttagag agtattgcct ccacttgttg tttcaagatg taccataaaa ttttgctttt    15300
acattttagt cttctaccac aagcatagat atccttgaga ccttgacctt aatctaaagg    15360
agaagttacc tatgccaggt ttctgagcaa ggatgtggaa gtgaaccaaa tgggggtgtt    15420
caggccacac atgcaatcag caaaggatat gatgtacatg caccaatcag tctccagcta    15480
agccagccac aaacacagaa gagtgtaaca tcaacaagcg tcatgcagct tgggtaa       15537
```

<210> SEQ ID NO 15
<211> LENGTH: 235
<212> TYPE: PRT
<213> ORGANISM: Nicotiana tabacum

<400> SEQUENCE: 15

```
Met Gly Arg Gly Lys Ile Val Ile Gln Arg Ile Asp Asn Thr Thr Ser
1               5                   10                  15

Arg Gln Val Thr Phe Ser Lys Arg Arg Asn Gly Leu Leu Lys Lys Ala
            20                  25                  30

Lys Glu Leu Ala Ile Leu Cys Asp Ala Glu Val Gly Leu Ile Ile Phe
        35                  40                  45

Ser Ser Thr Gly Lys Leu Tyr Glu Phe Ser Ser Asn Ser Met Arg Ala
    50                  55                  60

Ile Ile Asp Arg Tyr Asn Glu Met Lys Glu Glu His His Asn Leu Met
65                  70                  75                  80

Ser Pro Met Ser Glu Val Lys Phe Trp Gln Arg Glu Ile Ala Ser Leu
                85                  90                  95

Arg Gln Gln Leu His Tyr Leu Gln Glu Asn His Arg Gln Leu Leu Gly
            100                 105                 110

Glu Glu Leu Ser Gly Leu Ser Ile Lys Asp Leu Thr Asn Leu Glu Asn
        115                 120                 125

Gln Leu Glu Met Ser Leu Lys Gly Val Arg Lys Gln Lys Glu Gln Ile
    130                 135                 140

Leu Thr Asp Glu Ile Arg Glu Leu Asn Gln Lys Gly Asn Leu Ile His
145                 150                 155                 160

Gln Glu Asn Ile Glu Leu Tyr Lys Lys Val Asn Leu Ile Arg Gln Glu
                165                 170                 175

Asn Thr Glu Leu Lys Lys Lys Val Ser Glu Gly Cys Gly Ser Glu
            180                 185                 190

Pro Asn Gly Gly Val Gln Ala Thr His Ala Ile Ser Lys Gly Tyr Asp
        195                 200                 205

Val His Ala Pro Ile Ser Leu Gln Leu Ser Gln Pro Gln Thr Gln Lys
    210                 215                 220

Ser Val Thr Ser Thr Ser Val Met Gln Leu Gly
225                 230                 235
```

<210> SEQ ID NO 16
<211> LENGTH: 515
<212> TYPE: DNA
<213> ORGANISM: Artificial Sequence
<220> FEATURE:
<223> OTHER INFORMATION: synthetically-generated oligonucleotide

<400> SEQUENCE: 16

```
aattggatcc atggggagag gaaaaattgt gattcaaagg attgacaata caacaagcag     60
gcaagtgact ttctcaaaga gaagaaatgg gctgctgaag aaggctaaag agctagcaat    120
tctttgtgat gctgaagttg gactcattat tttctccagc actggaaaac tctatgaatt    180
ttaataagat cttcaacacc tacaccattt ttttaatcac tactacccat tgcattgaac    240
aaacttccaa gttcttctta gcttcagatt aagaaagtac cctttcttgg ctttgttgat    300
gtggtaccat tgtccattgt cttgtgtgtt tccaaaattc atagagtttt ccagtgctgg    360
agaaaataat gagtccaact tcagcatcac aaagaattgc tagctcttta gccttcttca    420
gcagcccatt tcttctcttt gagaaagtca cttgcctgct tgttgtattg tcaatccttt    480
gaatcacaat ttttcctctc cccattctag aaatt                              515
```

<210> SEQ ID NO 17
<211> LENGTH: 1194
<212> TYPE: DNA
<213> ORGANISM: Nicotiana tabacum

<400> SEQUENCE: 17

```
atgtctcaag atggctcagc agcagcaaca atggatcgga agaaggattc tcaatcaaca      60
acaaacccta cccgaaatgg taacggtaac ggtaacggcg aacagcaac aaacggcgcc     120
gtttacccgt cactcaattc tctgaggttg cgtttaaacc ctagtattga tcacaagtcg    180
gataattatg aagatcttca attggatttt agtccattgt tatttagctc gctcgaacgg    240
taccttccgc ctactctcct caattcgtca cgtgaccata agttcatta catgcgggaa     300
attctcctta agtattgtcc tgaaggtgaa cgtacacgtg tgcagaagca tagggaatac    360
cgacagaaga ttatatcaaa ctatcagcct ctacacaggg agttatatac catgcatgct    420
gcgaattttt ttgtgccatc atttcttaag gcaattagcg agaacacaga ggaaagttac    480
agaaacataa tgtcggaacc ctctcctgga gttttaacat tgaaatgct tcaaccacga    540
ttttgtgaga tgatgttggc tgaggtagaa actttgaaa ggtgggtccg cgagacaaag    600
ttcagaataa tgcgtcccaa tacaatgaac aaatttggtg ccgttcttga tgactttggc    660
ctcgaaacta tgcttgacaa gttgatgaa gatttcattc gtcccatttc aagagttttc    720
tttactgaag ttggtggatc cacacttgat agccatcacg gttttgttgt cgagtatggg    780
atggatagag atgttgactt gggttttcat gttgatgact cagaagtaac tttaaatgtg    840
tgcttgggta agcaattctc tggtggagag ctgttcttcc gtggagtgcg gtgtgagaag    900
catgtaaata ctgaaacaca acctgaggag atctttgatt actcccatgt cacggggcgt    960
gcagtgcttc atcgtggtcg ccatcggcat ggtgctagag caacaacatc ggggcagagg  1020
atcaacttgt tgttgtggtg cagaagttct gtctttagag agctaaggaa gtaccagaaa  1080
gactttccg gctggtgtgc agagtgccag cgcgagaaga aggaaaggca acgactgtcc  1140
attgctgcta ctaaattgga gctgctgaaa agagaagggg aagctgctac atag         1194
```

<210> SEQ ID NO 18
<211> LENGTH: 5548
<212> TYPE: DNA
<213> ORGANISM: Nicotiana tabacum

<400> SEQUENCE: 18

-continued

| | | | | | |
|---|---|---|---|---|---|
| atgtctcaag | atggctcagc | agcagcaaca | atggatcgga | agaaggattc | tcaatcaaca | 60 |
| acaaaccta | cccgaaatgg | taacggtaac | ggtaacggcg | aacagcaac | aaacggcgcc | 120 |
| gtttacccgt | cactcaattc | tctgaggttg | cgtttaaacc | ctagtattga | tcacaagtcg | 180 |
| gataattatg | aagatcttca | attggatttt | agtccattgt | tatttagctc | gctcgaacgg | 240 |
| taccttccgc | ctactctcct | caattcgtca | cgtgaccata | aagttcatta | catgcgggaa | 300 |
| attctcctta | agtattgtcc | tgaaggtgaa | cgtacacgtg | taagtatagc | attttcaatt | 360 |
| ttgtaaatta | cattttcaa | ttttgcgttt | gtaatttgca | tgtgattgtt | gttgttcttt | 420 |
| gtacattttg | attagtgtat | atattatgtt | agaatgtggg | tagtgaattg | agccattatt | 480 |
| aactgatgag | aagctgaaaa | gggaaaactt | agaagctgaa | cttttctgt | gctttgtatt | 540 |
| gcaattttgc | atgtacgttg | ccattaagca | atttgctgaa | aaatcaactt | tttttatgtc | 600 |
| gaattagttt | tctcaatgaa | acacctttgt | tagtattaaa | aaatagtgaa | agggtggctt | 660 |
| gtggagctct | aggtacgcag | agctgtgaat | tcagctgtaa | tagagtgctt | atatgctgtt | 720 |
| tgatgagaat | gaaaaaaaca | aaagaaaata | aaaagctaga | aaaatctggg | cttttttgatg | 780 |
| gttattgctg | aaaatctcgg | gctttgttttt | attctcatcc | attattgtcc | tgaacgtgaa | 840 |
| tttgcatttt | gcacgtggtt | tttttttttt | gtatttttta | ccgtggtatc | taggtcagct | 900 |
| tgtgcgtacc | tctattattc | caccggatac | ctgctacctc | caccggcgca | ggtactaggt | 960 |
| agctctatcc | actaagactt | aggcggatga | gaaaaaatca | tctaatatta | ttttgcctcc | 1020 |
| gctatgattt | gaacctgata | cttcgtgatt | ctcctcccac | tgaccactag | gccacaccct | 1080 |
| tgggtgcgac | atagcttgtt | tctcttttca | ataggcaaat | gatttaataa | ttcagggaga | 1140 |
| tgtgacccga | gtatagatgg | atataagaac | aaccaaaatt | ttggttaaaa | agaacatgtg | 1200 |
| atctaagtta | aacctacctg | gttaatttgt | ttataatgtg | gtggaatatt | tacaaaacat | 1260 |
| gccagtctcc | taatgaagtc | cttgtttacc | cttgaactat | taggaatgtt | gtctgctgat | 1320 |
| atagtcttct | ctgaatgtcc | tttgctttcc | aaacttttcc | ttgctatttg | tgagattgta | 1380 |
| ctctctctct | ctctctcatt | ccgaaactct | atcagtacaa | tattgtttca | tctcctctgc | 1440 |
| tttaacaggt | gcagaagcat | agggaatacc | gacagaagat | tatatcaaac | tatcaggtat | 1500 |
| ttacgttctg | cagaagggat | ttgtaggtta | atatttcagt | gatggttgta | aatgaagaca | 1560 |
| tcaatttta | tactttttgt | tgttaagtct | attaaagtaa | ggtaagaaag | tttacgtaac | 1620 |
| tttgcttgcg | ttttctctgg | agagaaatgc | ctttccattt | aaagaattat | aagcatagaa | 1680 |
| tgtaatgctc | attgatcttc | gtttagcatt | aatcttcttc | cttctatttt | tctaattagc | 1740 |
| tttcctttta | ttccagcctc | tacacaggga | gttatatacc | atgcatgctg | cgaatttttt | 1800 |
| tgtgccatca | tttcttaagg | caattagcga | gaacacagag | gaaagttaca | gaaacataat | 1860 |
| gtcggaaccc | tctcctggag | ttttaacatt | tgaaatgctt | caaccacgat | tttgtgagat | 1920 |
| gatgttggct | gaggtatcaa | ccggcttgct | gctgttattt | gcatgctaa | atctagtttt | 1980 |
| tctttgtagt | ttagcatttc | tgttttctta | tcaggttcta | ttgcttaggt | agaaaacttt | 2040 |
| gaaaggtggg | tccgcgagac | aaagttcaga | ataatgcgtc | ccaatacaat | gaacaaattt | 2100 |
| ggtgccgttc | ttgatgactt | tggcctcgaa | actatgcttg | acaagttgat | ggaagatttc | 2160 |
| attcgtccca | tttcaagagg | taagaatttt | acttttaact | gcgatgcagc | aagaaaggag | 2220 |
| agaggatctg | attgtgaaaa | ttagttggct | cttctcttag | tcttcctctt | tgatattttt | 2280 |
| gtgcagtttt | ctttactgaa | gttggtggat | ccacacttga | tagccatcac | ggttttgttg | 2340 |
| tcgagtatgg | gatggataga | gatgttgact | tgggtaaatt | tttgtatgct | tttgagtacg | 2400 |

```
ggcacacttt taccctttct ttaagtgaat tttttacctt atcaaaaaaa agttattgtt    2460
tgtttagtac ttattggggt cagctattgc tttgaagtgc ctcaaagcct ttttggctct    2520
gtgagggaca ttgtcttgca tctcaaccaa tttaattttc aggttttcat gttgatgact    2580
cagaagtaac tttaaatgtg tgcttgggta agcaattctc tggtggagag ctgttcttcc    2640
gtggagtgcg gtgtgagaag catgtaaata ctgaaacaca acctgaggta attattgttc    2700
cgttgtttga ttaactgtgc acgagaaatc tctgtttcaa taggaagcca tgtttccatt    2760
atttcatatt tatcaacaaa aaaattccat tatttcctat gtattttgt ttaaatggtt      2820 attgtgttgt cgaaactagt agcttttgc acagtgccct tactgtcaac aacctggtaa     2880
ccaagtgtat tgcaactttt tcagagaaaa tgctgactgt ttattgtgat aatttgaagt    2940
cgtgataaat gttaaacctg agtttcaaag ctggatccat gacaatcttc ttgatcacgt    3000
gccggaacgg aaaaaggcag aggactgctc ttatctcttt ttacttttac aagtcaaaat    3060
gattccattg atatccacca tacagtgtga atgaacgata agcttcaggt gaaaaaacgg    3120
aaacctccaa ctatataaag aatatgacat gtcttcttta caccagaagt acaaatgaaa    3180
caaaatgtag atttaactct ccacattgga ctctcaaccc cttcaaacat ttcttctgct    3240
ccttctccat attagccaat taaagaggca caactttcca ttattcgctt atactggcat    3300
ccaactggtg gtacctttta ttggcacctt actttgaatg cagatttgct tgctttattt    3360
ctccatagta atcagtgatg atgaatatat gctgtgttat taccaagttt atcagctcat    3420
tctcgaagtc tacatatggt ttaaatactg aagaaagaat gttgttagct ccacgttatt    3480
tgtgtgttag agtatatatc atcaaattca aaatacaact tatgcatgtc aagagcattc    3540
actatggatt tggaataatt taacaggaga tctttgatta ctcccatgtc acggggcgtg    3600
cagtgcttca tcgtggtcgc catcggcatg gtgctagagc aacaacatcg gggcagagga    3660
tcaacttgtt gttgtggtgc agaaggtatt agatgctgtt gccttgctat tttgatcgtt    3720
tccactagac aatttgcttc aaacacagtc gtgaaaattt gttattgttg gaatatcctg    3780
ttaccgctgc attacctact gtttgaagtt ttaagctgtg cttcataatt gtttgagaac    3840
agcagtggat gcagctcttt ggcaacaggt tcatctgaac ctagtatttt ttccgcggta    3900
tgtgaaaacc cgctaaattt caacaaataa aaaagggcag cccagcacac aaagcatctc    3960
gcattcacac agggtccggg gaagggccgc atcctaaggg gtgtgatgta gacagcctac    4020
actaattcca ctgctcgaac cggtgaccta taggtcatac cgagacaact ttctcgtcgc    4080
tctaaggctc tccttcttaa atttcaacaa atattagatc taaacccata cttttagaa      4140 gaacaatgag ttcagagcta agaaccttaa aggtcaaacc catctaagtt taaatccttg    4200
tctgcctctg tttaagtatg caatattgat gcttaactac ggtctccatt ttatctgcat    4260
agtcctcctt gatgcagata tttggatgtt ttccattta tttctggcat cagtgcttca     4320
agtactgaaa gtagtttatg tatatcaact ttcaatgata tgaggagaag tagtgtaaag    4380
tgacggtggg gaaggagcg aatactgtct tataatcatg aaaacatgat gctgatattc     4440
cttgaggcac ctaaatatat gtgccatgct gagttggcaa ctgaaaatgg catgagttaa    4500
cttggaatag catagtttag catgtttgta gaaacgttga ttaaatggtt acattatatc    4560
tagatctcaa cttttccct tggccattga tagtggttgg tcatacagac atctactagt      4620
tatcgtgatt tgtcaaattt tttatggata cctgattacc tggtggttat ggtatcactc    4680
attctccttt ttcacaaaat aaaagaagag ttttgataaa cagctgaatg catatcatgc    4740
```

```
tttctggaaa agcttttctc aagaattgga gatgcacata ttattgattt tcttttttcag    4800 tgatgatagg taacttcata taggataaat tcgttttgca ctaactgttt tacatggaca    4860
gtgtgcttca tggtattcct aaaccttgaa ccatgttttg ctcatgtttg gcttcaaact    4920
tatcaggatt aaaattgctg gaggtattgc taagatgcta agaaaaatct gatttataca    4980
aggcttcact tcatatgatg caaaatcttt gcttggagta tctaattgta actgcttttt    5040
caagagggga tggtccggtg ttggtaaaag tgcataacat tatacttgtt ccaactaaat    5100
aatttgtttt acttgtcaat aaaaattgta tgtaaagata tgaacttctt tgctgcaact    5160
caatcagacc agatctcaat aattcggatg tcttacttttt attcatcttc cagaatcatt    5220
gaatacctga tagttgctat ctttcccttta cagttctgtc tttagagagc taaggaagta    5280
ccagaaagac ttttccggct ggtgtgcaga gtgccagcgc gagaagaagg aaaggcaacg    5340
actgtccatt gctgctacta aattggtaag caataattgt ctcttgtaat aactttaaca    5400
aatagttgac aagctctgct tatgcattat gacattaaaa ggtgaaatat agttagagct    5460
ggttgaagta ttttttctaaa ttattttgtc atttgtcctt tatgttttcc aggagctgct    5520
gaaaagagaa ggggaagctg ctacatag                                       5548
```

```
<210> SEQ ID NO 19
<211> LENGTH: 397
<212> TYPE: PRT
<213> ORGANISM: Nicotiana tabacum

<400> SEQUENCE: 19

Met Ser Gln Asp Gly Ser Ala Ala Thr Met Asp Arg Lys Lys Asp
1               5                   10                  15

Ser Gln Ser Thr Thr Asn Pro Thr Arg Asn Gly Asn Gly Asn Asn
            20                  25                  30

Gly Gly Thr Ala Thr Asn Gly Ala Val Tyr Pro Ser Leu Asn Ser Leu
        35                  40                  45

Arg Leu Arg Leu Asn Pro Ser Ile Asp His Lys Ser Asp Asn Tyr Glu
    50                  55                  60

Asp Leu Gln Leu Asp Phe Ser Pro Leu Phe Ser Ser Leu Glu Arg
65                  70                  75                  80

Tyr Leu Pro Pro Thr Leu Leu Asn Ser Ser Arg Asp His Lys Val His
                85                  90                  95

Tyr Met Arg Glu Ile Leu Leu Lys Tyr Cys Pro Glu Gly Glu Arg Thr
            100                 105                 110

Arg Val Gln Lys His Arg Glu Tyr Arg Gln Lys Ile Ile Ser Asn Tyr
        115                 120                 125

Gln Pro Leu His Arg Glu Leu Tyr Thr Met His Ala Ala Asn Phe Phe
    130                 135                 140

Val Pro Ser Phe Leu Lys Ala Ile Ser Glu Asn Thr Glu Glu Ser Tyr
145                 150                 155                 160

Arg Asn Ile Met Ser Glu Pro Ser Pro Gly Val Leu Thr Phe Glu Met
                165                 170                 175

Leu Gln Pro Arg Phe Cys Glu Met Met Leu Ala Glu Val Asn Phe
            180                 185                 190

Glu Arg Trp Val Arg Glu Thr Lys Phe Arg Ile Met Arg Pro Asn Thr
        195                 200                 205

Met Asn Lys Phe Gly Ala Val Leu Asp Asp Phe Gly Leu Glu Thr Met
    210                 215                 220

Leu Asp Lys Leu Met Glu Asp Phe Ile Arg Pro Ile Ser Arg Val Phe
```

```
                225                 230                 235                 240
            Phe Thr Glu Val Gly Gly Ser Thr Leu Asp Ser His His Gly Phe Val
                            245                 250                 255

Val Glu Tyr Gly Met Asp Arg Asp Val Asp Leu Gly Phe His Val Asp
                            260                 265                 270

Asp Ser Glu Val Thr Leu Asn Val Cys Leu Gly Lys Gln Phe Ser Gly
                        275                 280                 285

Gly Glu Leu Phe Phe Arg Gly Val Arg Cys Glu Lys His Val Asn Thr
                        290                 295                 300

Glu Thr Gln Pro Glu Glu Ile Phe Asp Tyr Ser His Val Thr Gly Arg
            305                 310                 315                 320

Ala Val Leu His Arg Gly Arg His Arg His Gly Ala Arg Ala Thr Thr
                            325                 330                 335

Ser Gly Gln Arg Ile Asn Leu Leu Leu Trp Cys Arg Ser Ser Val Phe
                        340                 345                 350

Arg Glu Leu Arg Lys Tyr Gln Lys Asp Phe Ser Gly Trp Cys Ala Glu
                        355                 360                 365

Cys Gln Arg Glu Lys Lys Glu Arg Gln Arg Leu Ser Ile Ala Ala Thr
                        370                 375                 380

Lys Leu Glu Leu Leu Lys Arg Glu Gly Glu Ala Ala Thr
            385                 390                 395

<210> SEQ ID NO 20
<211> LENGTH: 490
<212> TYPE: DNA
<213> ORGANISM: Artificial Sequence
<220> FEATURE:
<223> OTHER INFORMATION: synthetically-generated oligonucleotide

<400> SEQUENCE: 20
aattggatcc atgtctcaag atggctcagc agcagcaaca atggatcgga agaaggattc      60
tcaatcaaca acaaacccta cccgaaatgg taacggtaac ggtaacggcg aacagcaac     120 aaacggcgcc gtttacccgt cactcaattc tctgaggttg cgtttaaact aataagatct    180
tcaacaccta caccattttt ttaatcacta ctacccattg cattgaacaa acttccaagt    240
tcttcttagc ttcagattaa gaaagtaccc tttcttggct ttgttgatgt ggtaccattg    300
tccattgtct tgtgtgtttc cgtttaaacg caacctcaga gaattgagtg acgggtaaac    360
ggcgccgttt gttgctgttc cgccgttacc gttaccgtta ccatttcggg tagggtttgt    420
tgttgattga gaatccttct tccgatccat tgttgctgct gctgagccat cttgagacat    480
tctagaaatt                                                          490
```